(12) United States Patent
Hou et al.

(10) Patent No.: US 12,139,732 B1
(45) Date of Patent: Nov. 12, 2024

(54) ENGINEERED DEAMINASES

(71) Applicant: PIONEER HI-BRED INTERNATIONAL, INC., Johnston, IA (US)

(72) Inventors: Zhenglin Hou, Ankeny, IA (US); Sandeep Kumar, Johnston, IA (US); Joshua K Young, Johnston, IA (US)

(73) Assignee: PIONEER HI-BRED INTERNATIONAL, INC, IA (US)

( * ) Notice: Subject to any disclaimer, the term of this patent is extended or adjusted under 35 U.S.C. 154(b) by 0 days.

(21) Appl. No.: 17/808,128

(22) Filed: Jun. 22, 2022

Related U.S. Application Data

(60) Provisional application No. 63/214,488, filed on Jun. 24, 2021.

(51) Int. Cl.
| | |
|---|---|
| *C12N 9/22* | (2006.01) |
| *C12N 9/78* | (2006.01) |
| *C12N 15/11* | (2006.01) |
| *C12N 15/82* | (2006.01) |

(52) U.S. Cl.
CPC .................. *C12N 9/78* (2013.01); *C12N 9/22* (2013.01); *C12N 15/11* (2013.01); *C12N 15/82* (2013.01); *C12Y 305/04002* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2018/0127780 A1* 5/2018 Liu .......................... C12N 7/00

OTHER PUBLICATIONS

Leimbach et al., Uniprot Accession No. A0A0E1M050, May 2015.*

* cited by examiner

*Primary Examiner* — Richard G Hutson

(57) ABSTRACT

Novel engineered non-natural deaminases are provided. Methods and compositions are provided for modifying the genome of a cell, including a plant cell. Genome modification through guided CRISPR polypeptides and multiple deaminases are provided. Engineered non-natural novel deaminases, including adenosine deaminases are provided. These novel deaminases have improved activity in cells including plant cells.

10 Claims, 9 Drawing Sheets

Specification includes a Sequence Listing.

FIG. 1

| SEQ ID NO: | 11 | 10 | 13 | 16 | 2 | 9 | 1 | 12 | 4 | 14 | 5 | 7 | 8 | 15 | 3 | 6 |
|---|---|---|---|---|---|---|---|---|---|---|---|---|---|---|---|---|
| 11 | 100% | 74% | 77% | 73% | 79% | 79% | 84% | 77% | 76% | 76% | 76% | 75% | 76% | 76% | 75% | 74% |
| 10 | 74% | 100% | 79% | 82% | 78% | 77% | 79% | 79% | 80% | 79% | 78% | 78% | 79% | 81% | 81% | 83% |
| 13 | 77% | 79% | 100% | 77% | 84% | 85% | 82% | 83% | 84% | 84% | 83% | 83% | 82% | 83% | 83% | 82% |
| 16 | 73% | 82% | 77% | 100% | 77% | 78% | 78% | 80% | 80% | 80% | 80% | 79% | 80% | 80% | 81% | 84% |
| 2 | 79% | 78% | 84% | 77% | 100% | 97% | 83% | 80% | 83% | 83% | 85% | 83% | 83% | 84% | 82% | 86% |
| 9 | 79% | 77% | 85% | 78% | 97% | 100% | 84% | 80% | 82% | 82% | 85% | 82% | 83% | 83% | 82% | 84% |
| 1 | 84% | 79% | 82% | 78% | 83% | 84% | 100% | 82% | 85% | 84% | 84% | 83% | 81% | 84% | 81% | 83% |
| 12 | 77% | 79% | 83% | 80% | 80% | 80% | 82% | 100% | 84% | 85% | 85% | 85% | 84% | 85% | 86% | 85% |
| 4 | 76% | 80% | 84% | 80% | 83% | 82% | 85% | 84% | 100% | 99% | 93% | 93% | 81% | 83% | 84% | 86% |
| 14 | 76% | 79% | 84% | 80% | 83% | 82% | 84% | 85% | 99% | 100% | 93% | 93% | 81% | 83% | 84% | 86% |
| 5 | 76% | 78% | 83% | 79% | 85% | 85% | 84% | 85% | 93% | 93% | 100% | 95% | 83% | 84% | 85% | 87% |
| 7 | 75% | 78% | 83% | 80% | 83% | 82% | 83% | 85% | 93% | 93% | 95% | 100% | 81% | 83% | 85% | 86% |
| 8 | 76% | 79% | 82% | 80% | 83% | 83% | 81% | 84% | 81% | 81% | 83% | 81% | 100% | 93% | 84% | 88% |
| 15 | 76% | 81% | 83% | 81% | 84% | 83% | 84% | 85% | 83% | 83% | 84% | 83% | 93% | 100% | 86% | 90% |
| 3 | 75% | 81% | 83% | 81% | 82% | 82% | 81% | 86% | 84% | 84% | 85% | 85% | 84% | 86% | 100% | 93% |
| 6 | 74% | 83% | 82% | 84% | 86% | 84% | 83% | 85% | 86% | 86% | 87% | 86% | 88% | 90% | 93% | 100% |

UMD   Novel adenosine deaminase polypeptide (SEQ ID NOs: 2-16)
ENG   Engineered novel adenosine deaminase polypeptide (SEQ ID NOs: 17-31)
\*       SEQ ID NO: 32

A U6 promoter plus 3' G bp for expression (SEQ ID NO: 89)
B Sequence encoding Cas variable targeting domain of gRNA (SEQ ID NO: 90)
C Sequence encoding Cas recognition domain of gRNA (SEQ ID NO: 91)
D U6 terminator (SEQ ID NOs: 92)

FIG. 7

| SEQ ID NO. | Sequence |
|---|---|
| 93 | DAKTGAAAGSLIDVLHHPGMNHRVEIAEGVLAESCSAMLSDFFRWRREEKKALKKARQA-D |
| 94 | DAKTGAAAGSLIDVLHHPGMNHRVEITEGILAESCSAMLSDFFRWRREEKKALRKARQE-- |
| 95 | DAKTGAAAGSLMDVLHHPGMNHRVEISEGVLAESCSAMLSDFFRWRREEKKAQKKAREQTG |
| 96 | DAKTGAAAGSLMDVLHHPGMNHRVEISEGVLAESCSAMLSDFFRWRREEKKALKKAREQTG |
| 97 | DAKTGAAAGSLMDVLHHPGMNHRVEITEGILADECAALLSDFFRMRRQEIKAQKKAQSS-- |
| 98 | DAKTGAAAGSLMDVLHHPGMNHRVEVTEGVLREQCAGMLSDFFRERREQIKALRKAQKA-E |
| 99 | DAKTGAAAGSLIDVLHHPGMNHRVEITEGVLADECSAMLSDFFRHRRQQQKALKQSLKN-- |
| 100 | DAKTGAAAGSLIDVLHHPGMNHRVEITEGVLAEECSAMLSDFFRHRRQQQKALRQAEKG-- |
| 101 | DAKTGAAAGSLIDILHHPGMNHRVEFTEGVLKDTCATLLSEFFRHRRQVKKALRQAEKD-- |
| 102 | DAKTGAAAGSLMDVLHHPGMNHRVEVTEGILRDQCASMLSDFFRERREQIKALRKAQKA-G |
| 103 | DEKTGAAAGSLMDVLGHPGMNHQVKTIGGVLAPECSGLLSDFFRMRRQQKKQQKAELKL-L |
| 104 | DAKTGAAAGSLMDVLHHPGMNHRVDVTEGVLRDECATLLSDFFRMRRQEIKALKKSAN--- |
| 105 | DAKTGAAAGSLIDVLHHPGMNHRVEITEGVLRDECAAMLSDFFRQRRLEKKALKKPTGDPT |
| 106 | DAKTGAAAGSLMDVLHHPGMNHRVEITEGVLGAECASLLSDFFRQRREQKKALKRGC---- |
| 107 | DAKTGAAAGSLMDVLHHPGMNHRVEFTEGVLGEECAALLSDFFRHRRQVKKALRQAEKS-- |
| 108 | DAKTGAVGSLMDITGHPGMNHQVIEGILATECSAMLSAFFRQRRLEKKALKEATKRAT--. |

ENGINEERED DEAMINASES

CROSS-REFERENCE TO RELATED APPLICATION

This application claims priority to U.S. Provisional Application No. 63/214,488, filed on Jun. 24, 2021, which is incorporated by reference herein in its entirety.

FIELD

The disclosure relates to the field of plant molecular biology, in particular, to compositions and methods for altering the genome of a cell.

REFERENCE TO SEQUENCE LISTING SUBMITTED ELECTRONICALLY

The official copy of the sequence listing is submitted electronically via EFS-Web as an ASCII formatted sequence listing with a file named "8858-US NP_Sequence-_Listing_ST25" created on Jun. 18, 2024 and having a size of 143 kilobytes. The sequence listing comprised in this ASCII formatted document is part of the specification and is herein incorporated by reference in its entirety.

BACKGROUND

Recombinant DNA technology has made it possible to insert DNA sequences at targeted genomic locations and/or modify specific endogenous chromosomal sequences. Site-specific integration techniques, which employ site-specific recombination systems, as well as other types of recombination technologies, have been used to generate targeted insertions of genes of interest in a variety of organism. Genome-editing techniques such as designer zinc finger nucleases (ZFNs), transcription activator-like effector nucleases (TALENs), or homing meganucleases, are available for producing targeted genome perturbations, but these systems employ designed nucleases that need to be redesigned for each target site, which renders them costly and time-consuming to prepare.

Newer technologies utilizing archaeal or bacterial adaptive immunity systems have been identified, called CRISPR (Clustered Regularly Interspaced Short Palindromic Repeats), which comprise different domains of effector proteins that encompass a variety of activities (DNA recognition, binding, and optionally cleavage).

Despite the identification and characterization of some of these systems, there remains a need for identifying novel effectors and systems, as well as demonstrating activity in eukaryotes, particularly animals and plants, to effect editing of endogenous and previously-introduced heterologous polynucleotides.

SUMMARY

Provided herein are methods and compositions for editing of genomes, such as plant genomes, to produce an organism with improved or desired characteristics.

Methods and compositions are provided for modifying the genome of a cell, particularly a plant cell, with a novel deoxyadenosine deaminase. These novel deaminases have improved activity in cells compared to other deaminases.

An engineered, non-natural deaminase comprising an amino acid sequence having at least 90% identity to a polypeptide sequence selected from the group consisting of: 1-31, 33-47, 51-65, 67-81, and 93-108 is described herein. In an embodiment, the deaminase is operably associated with a guided DNA-binding polypeptide; or a guided CRISPR-Cas polypeptide; or with a guided CRISPR-Cas polypeptide that lacks double-strand-break-inducing activity or a single strand nickase activity. In an embodiment, the CRISPR-Cas polypeptide is Type II or Type V. In an embodiment, the deaminase is an adenine deaminase. In an embodiment, the deaminase is at least 95% identical to a polypeptide sequence selected from the group consisting of: SEQ ID NOS: 1-31, 33-47, 51-65, 67-81, and 93-108.

A cell comprising the deaminases disclosed herein is provided. In an embodiment, the cell is an eukaryotic cell. In an embodiment, the cell is a plant cell.

A method of modifying a target site in the genome of a cell, the method comprising providing to the cell a deactivated CRISPR-Cas polypeptide that lacks double-strand-break-inducing activity, a guide polynucleotide, wherein the guide polynucleotide comprises a sequence that shares homology with the target in the genome of the cell, wherein the Cas polypeptide and the guide polynucleotide form a complex that recognizes and binds to the target site, and an engineered deaminase, wherein the deaminase comprises an amino acid sequence that is at least 90% identical to a sequence selected from the group consisting of SEQ ID NOS: 1-31, 33-47, and 93-108; and modifying the target site in the genome of the cell by changing one or more bases in the target site. In an embodiment, deaminase is an adenine deaminase. In an embodiment, the cell is incubated at a temperature of about 24-37 degrees Celsius for about 2-48 hours. In an embodiment, the Cas polypeptide and the guide polynucleotide are provided as a ribonucleoprotein complex. In an embodiment, the deaminase is provided as a DNA sequence that is transcribed and translated into a polypeptide. In an embodiment, the DNA sequence comprises a polynucleotide having at least 90% identity to a polynucleotide sequence selected from the group consisting of SEQ ID NOs: 51-65 and 67-81. In an embodiment, the cell is a plant cell. In an embodiment, the cell is used to obtain a progeny from the plant cell, wherein the progeny comprises the at least one base change. In an embodiment, the CRISPR-Cas polypeptide is a nickase.

A multiplexed method of modifying a plurality of target sites simultaneously in a genome of a cell, the method comprising providing to the cell a deactivated CRISPR-Cas polypeptide that lacks double-strand-break-inducing activity, a plurality of guide polynucleotides, wherein the guide polynucleotides share similarity to the plurality of target sites in the genome of the cell; and an engineered deaminase, wherein the deaminase comprises an amino acid sequence that is at least 90% identical to a sequence selected from the group consisting of SEQ ID NOs: 1-31, 33-47, and 93-108; and modifying the plurality of target sites in the genome of the cell by changing one or more bases in the target site. In an embodiment, the CRISPR-Cas polypeptide is Type II or a Type V. In an embodiment, the deaminase and the CRISPR-Cas polypeptide is operably associated by a linker. In an embodiment, the deaminase and the CRISPR-Cas polypeptide is a fusion protein. In an embodiment, the cell is a plant cell.

BRIEF DESCRIPTION OF THE DRAWINGS AND SEQUENCE LISTING

The disclosure can be more fully understood from the following detailed description and the accompanying drawings and Sequence Listing, which form a part of this application.

FIG. 1 depicts percent identities across sequences derived from a PSI-BLAST query of the tRNA tadA deaminase from *E. coli*.

FIG. 7 shows a multiple sequence alignment of the novel deaminases. Distinct C-terminal motif is underlined. Unique conserved residues are indicated with a diamond.

Figure 8:
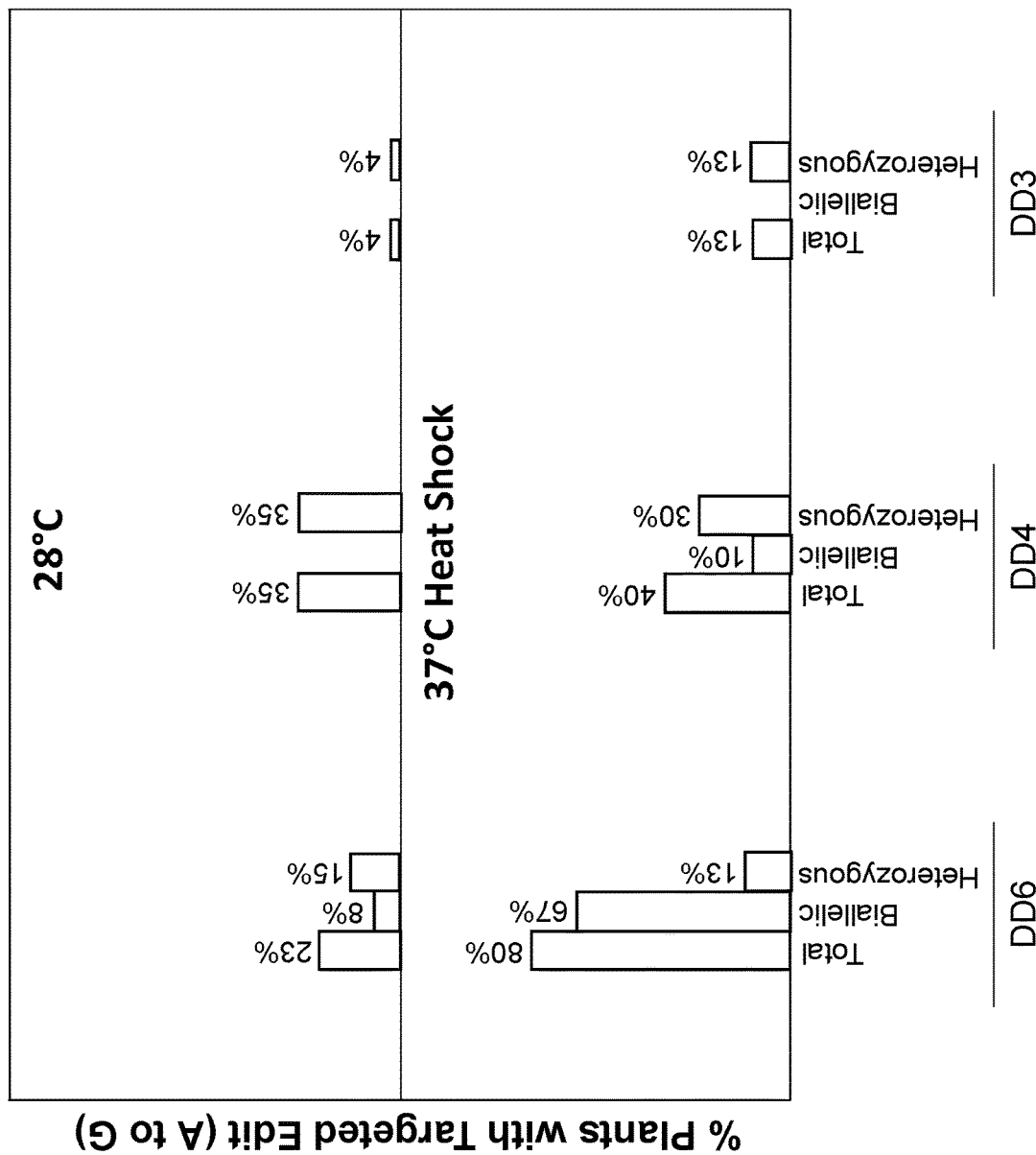

FIG. 8 depicts inplantae results at 28 degrees C. and 37 degrees C. heat shock. Plantlets containing an A to G bp conversion within the Cas9 target site were recovered in all experiments. The percentage of plants with biallelic and mono-allelic (heterozygous) editing are indicated.

Figure 9:
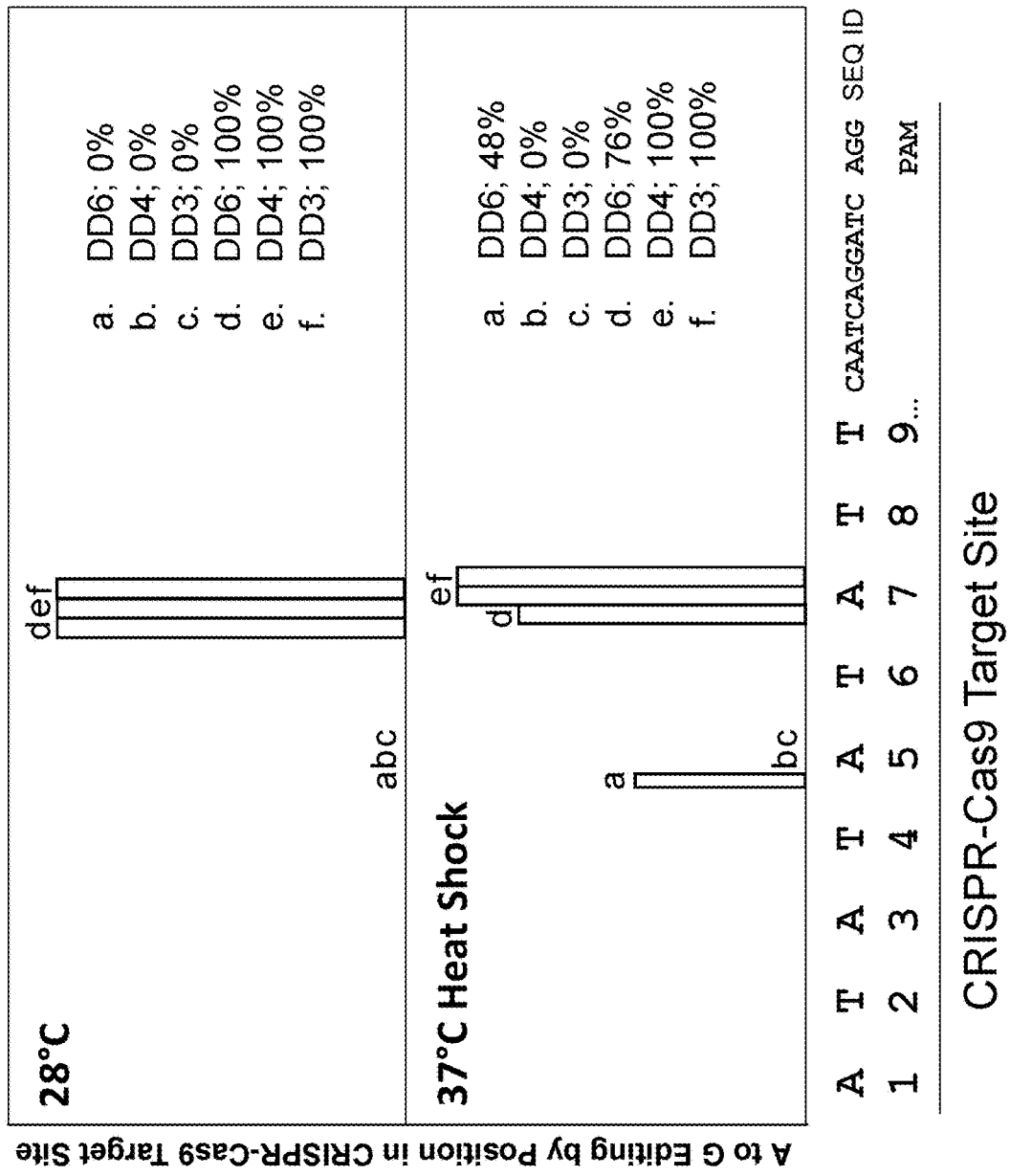

FIG. 9 shows the editing frequency at different positions within the CRISPR-Cas target site.

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

SEQ ID NO: 1 is the *E. coli* tRNA adenine deaminase PRT sequence from *Escherichia coli*.

SEQ ID NO: 2 is the Novel deaminase 1 PRT sequence from Enterobacteriaceae *bacterium* strain FGI 57.

SEQ ID NO: 3 is the Novel deaminase 2 PRT sequence from *Kluyvera georgiana*.

SEQ ID NO: 4 is the Novel deaminase 3 PRT sequence from *Klebsiella pneumoniae* (30).

SEQ ID NO: 5 is the Novel deaminase 4 PRT sequence from *Klebsiella aerogenes* (27).

SEQ ID NO: 6 is the Novel deaminase 5 PRT sequence from *Kluyvera ascorbata* ATCC 33433.

SEQ ID NO: 7 is the Novel deaminase 6 PRT sequence from *Raoultella* sp. (18).

SEQ ID NO: 8 is the Novel deaminase 7 PRT sequence from *Klebsiella* sp. RIT-PI-d.

SEQ ID NO: 9 is the Novel adenine deaminase 8 PRT sequence from Pseudocitrobacter *faecalis*.

SEQ ID NO: 10 is the Novel deaminase 9 PRT sequence from *Enterobacter cloacae* (15).

SEQ ID NO: 11 is the Novel deaminase 10 PRT sequence from *Citrobacter youngae*.

SEQ ID NO: 12 is the Novel deaminase 11 PRT sequence from Kosakonia pseudosacchari.

SEQ ID NO: 13 is the Novel deaminase 12 PRT sequence from Pluralibacter gergoviae.

SEQ ID NO: 14 is the Novel adenine deaminase 13 PRT sequence from *Klebsiella pneumoniae*.

SEQ ID NO: 15 is the Novel adenine deaminase 14 PRT sequence from Superficieibacter *electus*.

SEQ ID NO: 16 is the Novel adenine deaminase 15 PRT sequence from *Cronobacter malonaticus*.

SEQ ID NO: 17 is the Engineered novel adenine deaminase 1 PRT sequence.

SEQ ID NO: 18 is the Engineered novel adenine deaminase 2 PRT sequence.

SEQ ID NO: 19 is the Engineered novel adenine deaminase 3 PRT sequence.

SEQ ID NO: 20 is the Engineered novel adenine deaminase 4 PRT sequence.

SEQ ID NO: 21 is the Engineered novel adenine deaminase 5 PRT sequence.

SEQ ID NO: 22 is the Engineered novel adenine deaminase 6 PRT sequence.

SEQ ID NO: 23 is the Engineered novel adenine deaminase 7 PRT sequence.

SEQ ID NO: 24 is the Engineered novel adenine deaminase 8 PRT sequence.

SEQ ID NO: 25 is the Engineered novel adenine deaminase 9 PRT sequence.

SEQ ID NO: 26 is the Engineered novel adenine deaminase 10 PRT sequence.

SEQ ID NO: 27 is the Engineered novel adenine deaminase 11 PRT sequence.

SEQ ID NO: 28 is the Engineered novel adenine deaminase 12 PRT sequence.

SEQ ID NO: 29 is the Engineered novel adenine deaminase 13 PRT sequence.

SEQ ID NO: 30 is the Engineered novel adenine deaminase 14 PRT sequence.

SEQ ID NO: 31 is the Engineered novel adenine deaminase 15 PRT sequence.

SEQ ID NO: 32 is the Linker 1 PRT sequence.

SEQ ID NO: 33 is the Novel heterodimeric deoxyadenosine deaminase 1 PRT sequence.

SEQ ID NO: 34 is the Novel heterodimeric deoxyadenosine deaminase 2 PRT sequence.

SEQ ID NO: 35 is the Novel heterodimeric deoxyadenosine deaminase 3 PRT sequence.

SEQ ID NO: 36 is the Novel heterodimeric deoxyadenosine deaminase 4 PRT sequence.

SEQ ID NO: 37 is the Novel heterodimeric deoxyadenosine deaminase 5 PRT sequence.

SEQ ID NO: 38 is the Novel heterodimeric deoxyadenosine deaminase 6 PRT sequence.

SEQ ID NO: 39 is the Novel heterodimeric deoxyadenosine deaminase 7 PRT sequence.

SEQ ID NO: 40 is the Novel heterodimeric deoxyadenosine deaminase 8 PRT sequence.

SEQ ID NO: 41 is the Novel heterodimeric deoxyadenosine deaminase 9 PRT sequence.

SEQ ID NO: 42 is the Novel heterodimeric deoxyadenosine deaminase 10 PRT sequence.

SEQ ID NO: 43 is the Novel heterodimeric deoxyadenosine deaminase 11 PRT sequence.

SEQ ID NO: 44 is the Novel heterodimeric deoxyadenosine deaminase 12 PRT sequence.

SEQ ID NO: 45 is the Novel heterodimeric deoxyadenosine deaminase 13 PRT sequence.

SEQ ID NO: 46 is the Novel heterodimeric deoxyadenosine deaminase 14 PRT sequence.

SEQ ID NO: 47 is the Novel heterodimeric deoxyadenosine deaminase 15 PRT sequence.

SEQ ID NO: 48 is the Ubiquitin promoter DNA sequence.

SEQ ID NO: 49 is the Ubiquitin 5' UTR DNA sequence.

SEQ ID NO: 50 is the Ubiquitin intron 1 DNA sequence.

SEQ ID NO: 51 is the Sequence encoding novel adenine deaminase 1 DNA sequence.

SEQ ID NO: 52 is the Sequence encoding novel adenine deaminase 2 DNA sequence.

SEQ ID NO: 53 is the Sequence encoding novel adenine deaminase 3 DNA sequence.

SEQ ID NO: 54 is the Sequence encoding novel adenine deaminase 4 DNA sequence.

SEQ ID NO: 55 is the Sequence encoding novel adenine deaminase 5 DNA sequence.

SEQ ID NO: 56 is the Sequence encoding novel adenine deaminase 6 DNA sequence.

SEQ ID NO: 57 is the Sequence encoding novel adenine deaminase 7 DNA sequence.

SEQ ID NO: 58 is the Sequence encoding novel adenine deaminase 8 DNA sequence.

SEQ ID NO: 59 is the Sequence encoding novel adenine deaminase 9 DNA sequence.

SEQ ID NO: 60 is the Sequence encoding novel adenine deaminase 10 DNA sequence.

SEQ ID NO: 61 is the Sequence encoding novel adenine deaminase 11 DNA sequence.

SEQ ID NO: 62 is the Sequence encoding novel adenine deaminase 12 DNA sequence.

SEQ ID NO: 63 is the Sequence encoding novel adenine deaminase 13 DNA sequence.

SEQ ID NO: 64 is the Sequence encoding novel adenine deaminase 14 DNA sequence.

SEQ ID NO: 65 is the Sequence encoding novel adenine deaminase 15 DNA sequence.

SEQ ID NO: 66 is the Sequence encoding Linker 1 DNA sequence.

SEQ ID NO: 67 is the Sequence encoding novel engineered adenine deaminase 1 DNA sequence.

SEQ ID NO: 68 is the Sequence encoding novel engineered adenine deaminase 2 DNA sequence.

SEQ ID NO: 69 is the Sequence encoding novel engineered adenine deaminase 3 DNA sequence.

SEQ ID NO: 70 is the Sequence encoding novel engineered adenine deaminase 4 DNA sequence.

SEQ ID NO: 71 is the Sequence encoding novel engineered adenine deaminase 5 DNA sequence.

SEQ ID NO: 72 is the Sequence encoding novel engineered adenine deaminase 6 DNA sequence.

SEQ ID NO: 73 is the Sequence encoding novel engineered adenine deaminase 7 DNA sequence.

SEQ ID NO: 74 is the Sequence encoding novel engineered adenine deaminase 8 DNA sequence.

SEQ ID NO: 75 is the Sequence encoding novel engineered adenine deaminase 9 DNA sequence.

SEQ ID NO: 76 is the Sequence encoding novel engineered adenine deaminase 10 DNA sequence.

SEQ ID NO: 77 is the Sequence encoding novel engineered adenine deaminase 11 DNA sequence.

SEQ ID NO: 78 is the Sequence encoding novel engineered adenine deaminase 12 DNA sequence.

SEQ ID NO: 79 is the Sequence encoding novel engineered adenine deaminase 13 DNA sequence.

SEQ ID NO: 80 is the Sequence encoding novel engineered adenine deaminase 14 DNA sequence.

SEQ ID NO: 81 is the Sequence encoding novel engineered adenine deaminase 15 DNA sequence.

SEQ ID NO: 82 is the Variant sequence encoding Linker 1 DNA sequence.

SEQ ID NO: 83 is the Exon 1 of an optimized D10A nickase Sp Cas9 gene DNA sequence.

SEQ ID NO: 84 is the Exon 2 of an optimized D10A nickase Sp Cas9 gene DNA sequence.

SEQ ID NO: 85 is the ST-LS1 intron 2 DNA sequence from *Solanum tuberosum*.

SEQ ID NO: 86 is the Sequence encoding linker region 2 DNA sequence.

SEQ ID NO: 87 is the Sequence encoding SV40 nuclear localization signal DNA sequence.

SEQ ID NO: 88 is the UBI terminator DNA sequence from *Zea mays*.

SEQ ID NO: 89 is the U6 promoter plus 3' G bp for expression DNA sequence.

SEQ ID NO: 90 is the Sequence encoding Cas variable targeting domain of gRNA DNA sequence from *Zea mays*.

SEQ ID NO: 91 is the Sequence encoding Cas recognition domain of gRNA DNA sequence.

SEQ ID NO: 92 is the UBI terminator DNA sequence from *Zea mays*.

SEQ ID NO: 93 is the C-terminal portion of novel adenine deaminase 6 PRT sequence from *Raoultella* sp. (18).

SEQ ID NO: 94 is the C-terminal portion of novel adenine deaminase 4 PRT sequence from *Klebsiella aerogenes* (27).

SEQ ID NO: 95 is the C-terminal portion of novel adenine deaminase 3 PRT sequence from *Klebsiella pneumoniae* (30).

SEQ ID NO: 96 is the C-terminal portion of novel adenine deaminase 13 PRT sequence from *Klebsiella pneumoniae*.

SEQ ID NO: 97 is the C-terminal portion of *E. coli* tRNA adenine deaminase PRT sequence from *Escherichia coli*.

SEQ ID NO: 98 is the C-terminal portion of novel adenine deaminase 1 PRT sequence from Enterobacteriaceae *bacterium* strain FGI 57.

SEQ ID NO: 99 is the C-terminal portion of novel adenine deaminase 2 PRT sequence from *Kluyvera georgiana*.

SEQ ID NO: 100 is the C-terminal portion of novel adenine deaminase 5 PRT sequence from *Kluyvera ascorbata* ATCC 33433.

SEQ ID NO: 101 is the C-terminal portion of novel adenine deaminase 7 PRT sequence from *Klebsiella* sp. RIT-PI-d.

SEQ ID NO: 102 is the C-terminal portion of novel adenine deaminase 8 PRT sequence from Pseudocitrobacter *faecalis*.

SEQ ID NO: 103 is the C-terminal portion of novel adenine deaminase 9 PRT sequence from *Enterobacter cloacae* (15).

SEQ ID NO: 104 is the C-terminal portion of novel adenine deaminase 10 PRT sequence from *Citrobacter youngae*.

SEQ ID NO: 105 is the C-terminal portion of novel adenine deaminase 11 PRT sequence from Kosakonia pseudosacchari.

SEQ ID NO: 106 is the C-terminal portion of novel adenine deaminase 12 PRT sequence from Pluralibacter *gergoviae*.

SEQ ID NO: 107 is the C-terminal portion of novel adenine deaminase 14 PRT sequence from Superficieibacter *electus*.

SEQ ID NO: 108 is the C-terminal portion of novel adenine deaminase 15 PRT sequence from *Cronobacter malonaticus*.

SEQ ID NO: 109 is a consensus sequence representing a motif in the functional deaminases described herein.

SEQ ID NO 110: is a DNA sequence of a CRISPR-Cas9 target site.

DETAILED DESCRIPTION

DNA deaminases in conjunction with CRISPR-Cas tools offer to provide a step change in our ability to introduce precise DNA modifications into plant genomes. First, they don't require the introduction of a DNA double-strand break or repair template to precisely modify a chromosomal DNA target, ultimately, enabling multi-site editing approaches. Next, the frequencies of desirable base conversion far exceed those offered by homology directed repair approaches in plants.

Here, we have engineered novel deoxyadenosine deaminases that function to convert A-T bps to G-C bps at plant CRISPR-Cas chromosomal DNA target sites. Additionally, we find that this activity is temperature sensitive being non-functional at 28° C. and functional at 37° C. Altogether, this result suggests that the observed base editing is temperature regulatable potentially off-setting undesirable transcriptome modifications that have been associated with other deaminases.

Terms used in the claims and specification are defined as set forth below unless otherwise specified. It must be noted that, as used in the specification and the appended claims, the singular forms "a," "an" and "the" include plural referents unless the context clearly dictates otherwise.

As used herein, "nucleic acid" generally means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

A "deaminase" is an enzyme that catalyzes a deamination reaction. For example, deamination of adenine with an adenine deaminase results in the formation of hypoxanthine. Hypoxanthine selectively base pairs with cytosine instead of thymine. This results in a post-replicative transition mutation, such that the original A-T base pair transforms into a G-C base pair. In another example, cytosine deamination results in the formation of uracil, which would normally be repaired by cellular repair mechanisms back to cytosine but can be prevented introduction of a uracil glycosylase inhibitor, such that DNA repair or replication transforms the original G-C base pair into an A-T base pair.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

"Open reading frame" is abbreviated ORF.

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have structural similarity such that they are capable of acting as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

As used herein, "homologous recombination" (HR) includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any percentage from 50% to 100%. These identities can be determined using any of the programs described herein.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment. Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

A "centimorgan" (cM) or "map unit" is the distance between two polynucleotide sequences, linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Generally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. Isolated polynucleotides may be purified from a cell in which they naturally occur. Conventional nucleic acid purification methods known to skilled artisans may be used to obtain isolated polynucleotides. The term also embraces recombinant polynucleotides and chemically synthesized polynucleotides.

The term "fragment" refers to a contiguous set of nucleotides or amino acids. In one embodiment, a fragment is 2, 3, 4, 5, 6, 7 8, 9, 10, 11, 12, 13, 14, 15, 16, 17, 18, 19, 20, or greater than 20 contiguous nucleotides. In one embodiment, a fragment is 2, 3, 4, 5, 6, 7 8, 9, 10, 11, 12, 13, 14, 15, 16, 17, 18, 19, 20, or greater than 20 contiguous amino acids. A fragment may or may not exhibit the function of a sequence sharing some percent identity over the length of said fragment.

The terms "fragment that is functionally equivalent" and "functionally equivalent fragment" are used interchangeably herein. These terms refer to a portion or subsequence of an isolated nucleic acid fragment or polypeptide that displays the same activity or function as the longer sequence from which it derives. In one example, the fragment retains the ability to alter gene expression or produce a certain phenotype whether or not the fragment encodes an active protein. For example, the fragment can be used in the design of genes to produce the desired phenotype in a modified plant. Genes can be designed for use in suppression by linking a nucleic acid fragment, whether or not it encodes an active enzyme, in the sense or antisense orientation relative to a plant promoter sequence.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in its natural endogenous location with its own regulatory sequences.

By the term "endogenous" it is meant a sequence or other molecule that naturally occurs in a cell or organism. In one aspect, an endogenous polynucleotide is normally found in the genome of a cell; that is, not heterologous.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a gene (referred to as the target gene), including a native gene, that was made by altering a target sequence within the target gene using any method known to one skilled in the art, including a method involving a guided Cas endonuclease system as disclosed herein.

The terms "knock-out", "gene knock-out" and "genetic knock-out" are used interchangeably herein. A knock-out represents a DNA sequence of a cell that has been rendered partially or completely inoperative by targeting with a Cas protein; for example, a DNA sequence prior to knock-out could have encoded an amino acid sequence, or could have had a regulatory function (e.g., promoter).

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

By "domain" it is meant a contiguous stretch of nucleotides (that can be RNA, DNA, and/or RNA-DNA-combination sequence) or amino acids.

The term "conserved domain" or "motif" means a set of polynucleotides or amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

A "codon-modified gene" or "codon-preferred gene" or "codon-optimized gene" is a gene having its frequency of codon usage designed to mimic the frequency of preferred codon usage of the host cell.

An "optimized" polynucleotide is a sequence that has been optimized for improved expression in a particular heterologous host cell.

An "optimized nucleotide sequence" is a nucleotide sequence that has been optimized for expression in a particular organism. A plant-optimized nucleotide sequence includes a codon-optimized gene. A plant-optimized nucleotide sequence can be synthesized by modifying a nucleotide sequence encoding a protein such as, for example, a Cas endonuclease as disclosed herein, using one or more plant-preferred codons for improved expression. See, for example, Campbell and Gowri (1990) *Plant Physiol.* 92:1-11 for a discussion of host-preferred codon usage.

A "promoter" is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

Promoters that cause a gene to be expressed in most cell types at most times are commonly referred to as "constitutive promoters". The term "inducible promoter" refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase.

The term "genome" refers to the entire complement of genetic material (genes and non-coding sequences) that is present in each cell of an organism, or virus or organelle; and/or a complete set of chromosomes inherited as a (haploid) unit from one parent.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Generally, "host" refers to an organism or cell into which a heterologous component (polynucleotide, polypeptide, other molecule, cell) has been introduced. As used herein, a "host cell" refers to an in vivo or in vitro eukaryotic cell, prokaryotic cell (e.g., bacterial or archaeal cell), or cell from a multicellular organism (e.g., a cell line) cultured as a unicellular entity, into which a heterologous polynucleotide or polypeptide has been introduced. In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector comprising a gene and having elements in addition to the gene that facilitates transformation of a particular host cell. "Expression cassette" refers to a specific vector comprising a gene and having elements in addition to the gene that allow for expression of that gene in a host. In one aspect, a "Donor DNA cassette" comprises a heterologous polynucleotide to be inserted at the double-strand break site created by a double-strand-break inducing agent (e.g., a Cas endonuclease and guide RNA complex), that is operably linked to a noncoding expression regulatory element. In some aspects, the Donor DNA cassette further comprises polynucleotide sequences that are homologous to the target site, that flank the polynucleotide of interest operably linked to a noncoding expression regulatory element.

The terms "recombinant DNA molecule", "recombinant DNA construct", "expression construct", "construct", and "recombinant construct" are used interchangeably herein. A recombinant DNA construct comprises an artificial combination of nucleic acid sequences, e.g., regulatory and coding sequences that are not all found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to introduce the vector into the host cells as is well known to those skilled in the art.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from *Zea mays* would be heterologous if inserted into the genome of an *Oryza sativa* plant, or of a different variety or cultivar of *Zea mays*; or a polynucleotide obtained from a *bacterium* was introduced into a cell of a plant), or sequence (e.g., a polynucleotide sequence obtained from *Zea mays*, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, one or more regulatory region(s) and/or a polynucleotide provided herein may be entirely synthetic. In one aspect, a discrete component of a poly-gRNA molecule is heterologous to at least one other component, i.e., do not occur together in nature.

The term "expression", as used herein, refers to the production of a functional end-product (e.g., an mRNA, guide RNA, or a protein) in either precursor or mature form.

A "mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

"CRISPR" (clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, *Science* 327:167-170; WO2007025097, published 1 Mar. 2007). A CRISPR locus can include of a CRISPR array, comprising short direct repeats (CRISPR repeats) separated by short variable DNA sequences (called spacers), which can be flanked by diverse Cas (CRISPR-associated) genes.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes, but is not limited to, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence. A Cas endonuclease described herein comprises one or more nuclease domains. The endonucleases of the disclosure may include those having one or more RuvC nuclease domains. A Cas protein is further defined as a functional fragment or functional variant of a native Cas protein, or a protein that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native Cas protein, and retains at least partial activity.

A "Cas endonuclease" may comprise domains that enable it to function as a double-strand-break-inducing agent. A "Cas endonuclease" may also comprise one or more modifications or mutations that abolish or reduce its ability to cleave a double-strand polynucleotide (dCas). In some aspects, the Cas endonuclease molecule may retain the ability to nick a single-strand polynucleotide (for example, a D10A mutation in a Cas9 endonuclease molecule) (nCas9).

A "functional fragment", "fragment that is functionally equivalent" and "functionally equivalent fragment" of a Cas endonuclease are used interchangeably herein, and refer to a portion or subsequence of the Cas endonuclease of the present disclosure in which the ability to recognize, bind to, and optionally unwind, nick or cleave (introduce a single or double-strand break in) the target site is retained. The portion or subsequence of the Cas endonuclease can comprise a complete or partial (functional) peptide of any one of its domains such as for example, but not limiting to a complete of functional part of a Cas3 HD domain, a complete of functional part of a Cas3 Helicase domain, complete of functional part of a Cascade protein (such as but not limiting to a Cas5, Cas5d, Cas7 and Cas8b1).

The terms "functional variant", "variant that is functionally equivalent" and "functionally equivalent variant" of a Cas endonuclease or Cas effector protein are used interchangeably herein, and refer to a variant of the Cas effector protein disclosed herein in which the ability to recognize, bind to, and optionally unwind, nick or cleave all or part of a target sequence is retained.

A Cas endonuclease may also include a multifunctional Cas endonuclease. The term "multifunctional Cas endonuclease" and "multifunctional Cas endonuclease polypeptide" are used interchangeably herein and includes reference to a single polypeptide that has Cas endonuclease functionality (comprising at least one protein domain that can act as a Cas endonuclease) and at least one other functionality, such as but not limited to, the functionality to form a cascade (comprises at least a second protein domain that can form a cascade with other proteins). In one aspect, the multifunctional Cas endonuclease comprises at least one additional protein domain relative (either internally, upstream (5'), downstream (3'), or both internally 5' and 3', or any combination thereof) to those domains typical of a Cas endonuclease.

As used herein, the term "guide polynucleotide", relates to a polynucleotide sequence that can form a complex with a Cas endonuclease, including the Cas endonuclease described herein, and enables the Cas endonuclease to recognize, optionally bind to, and optionally cleave a DNA target site. The guide polynucleotide sequence can be a RNA sequence, a DNA sequence, or a combination thereof (a RNA-DNA combination sequence).

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, optionally bind to, and optionally nick or cleave (introduce a single or double-strand break) the DNA target site.

The term "variable targeting domain" or "VT domain" is used interchangeably herein and includes a nucleotide sequence that can hybridize (is complementary) to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a (trans-acting) tracrNucleotide mate sequence followed by a tracrNucleotide sequence. The CER domain can be composed of a DNA sequence, a RNA sequence, a modified DNA sequence, a modified RNA sequence (see for example US20150059010A1, published 26 Feb. 2015), or any combination thereof.

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "Polynucleotide-guided endonuclease", "PGEN" are used interchangeably herein and refer to at least one guide polynucleotide and at least one Cas endonuclease, that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s) and suitable polynucleotide component(s) of any of the known CRISPR systems (Horvath and Barrangou, 2010, *Science* 327:167-170; Makarova et al. 2015, *Nature Reviews Microbiology* Vol. 13:1-15; Zetsche et al., 2015, Cell 163, 1-13; Shmakov et al., 2015, *Molecular Cell* 60, 1-13).

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

The terms "target site", "target sequence", "target site sequence, "target DNA", "target locus", "genomic target site", "genomic target sequence", "genomic target locus", "target polynucleotide", and "protospacer", are used interchangeably herein and refer to a polynucleotide sequence such as, but not limited to, a nucleotide sequence on a chromosome, episome, a locus, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

As used herein, "donor DNA" is a DNA construct that comprises a polynucleotide of interest to be inserted into the target site of a Cas endonuclease.

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The term "plant" generically includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant cells comprise a plant cell wall, and as such are distinct, with different biochemical characteristics, from protoplasts that lack a cell wall.

A "plant element" or "plant part" is intended to reference either a whole plant or a plant component, which may comprise differentiated and/or undifferentiated tissues, for example but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue), plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. The term "plant organ" refers to plant tissue or a group of tissues that constitute a morphologically and functionally distinct part of a plant. As used herein, a "plant element" is synonymous to a "portion" or "part" of a plant, and refers to any part of the plant, and can include distinct tissues and/or organs, and may be used interchangeably with the term "tissue" throughout. Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keiki, or bud. The plant element may be in plant or in a plant organ, tissue culture, or cell culture.

"Progeny" comprises any subsequent generation of a plant.

The term "monocotyledonous" or "monocot" refers to the subclass of angiosperm plants also known as "monocotyledoneae", whose seeds typically comprise only one embryonic leaf, or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants also knows as "dicotyledoneae", whose seeds typically comprise two embryonic leaves, or cotyledons. The term includes references to whole plants, plant elements, plant organs (e.g., leaves, stems, roots, etc.), seeds, plant cells, and progeny of the same.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

The term "isoline" is a comparative term, and references organisms that are genetically identical, but differ in treatment. In one example, two genetically identical maize plant embryos may be separated into two different groups, one receiving a treatment (such as the introduction of a CRISPR-Cas effector endonuclease) and one control that does not receive such treatment. Any phenotypic differences between the two groups may thus be attributed solely to the treatment and not to any inherency of the plant's endogenous genetic makeup.

A "population" of plants refers to a plurality of individual plants that share temporal and spatial location, and may further share one or more characteristic(s), such as a common genotype.

"Introducing" is intended to mean presenting a subject molecule to a target, such as a cell or organism, a polynucleotide or polypeptide or polynucleotide-protein complex, in such a manner that the subject gains access to the target, such as the interior of a cell of the organism or to the cell itself, or in the case of a target polynucleotide, presented to the polynucleotide in such a way that the subject has capability of physical or chemical contact with the polynucleotide.

A "polynucleotide of interest" includes any nucleotide sequence that

In some aspects, a "polynucleotide of interest" encodes a protein or polypeptide that is "of interest" for a particular purpose, e.g., a selectable marker. In some aspects a trait or polynucleotide "of interest" is one that improves a desirable phenotype of a plant, particularly a crop plant, i.e., a trait of agronomic interest. Polynucleotides of interest: include, but are not limited to, polynucleotides encoding important traits for agronomics, herbicide-resistance, insecticidal resistance, disease resistance, nematode resistance, herbicide resistance, microbial resistance, fungal resistance, viral resistance, fertility or sterility, grain characteristics, commercial products, phenotypic marker, or any other trait of agronomic or commercial importance. A polynucleotide of interest may additionally be utilized in either the sense or anti-sense orientation. Further, more than one polynucleotide of interest may be utilized together, or "stacked", to provide additional benefit. In some aspects, a "polynucleotide of interest" may encode a gene expression regulatory element, for example a promoter, intron, terminator, 5'UTR, 3'UTR, or other noncoding sequence. In some aspects, a "polynucleotide of interest" may comprise a DNA sequence that encodes for an RNA molecule, for example a functional RNA, siRNA, miRNA, or a guide RNA that is capable of interacting with a Cas endonuclease to bind to a target polynucleotide sequence.

A "complex trait locus" includes a genomic locus that has multiple transgenes genetically linked to each other.

The compositions and methods herein may provide for an improved "agronomic trait" or "trait of agronomic importance" or "trait of agronomic interest" to a plant, which may include, but be not limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

"Agronomic trait potential" is intended to mean a capability of a plant element for exhibiting a phenotype, preferably an improved agronomic trait, at some point during its life cycle, or conveying said phenotype to another plant element with which it is associated in the same plant.

The terms "decreased," "fewer," "slower" and "increased" "faster" "enhanced" "greater" as used herein refers to a decrease or increase in a characteristic of the modified plant element or resulting plant compared to an unmodified plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400%) or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

As used herein, the term "before", in reference to a sequence position, refers to an occurrence of one sequence upstream, or 5', to another sequence.

The meaning of abbreviations is as follows: "sec" means second(s), "min" means minute(s), "h" means hour(s), "d" means day(s), "microliters" means microliter(s), "mL" means milliliter(s), "L" means liter(s), "uM" means micromolar, "mM" means millimolar, "M" means molar, "mmol" means millimole(s), "umole" mean micromole(s), "g" means gram(s), "micrograms" or "ug" means microgram(s), "ng" means nanogram(s), "U" means unit(s), "bp" means base pair(s) and "kb" means kilobase(s).

Cas Endonucleases
Cas Endonucleases and Effectors

Endonucleases are enzymes that cleave the phosphodiester bond within a polynucleotide chain. Examples of endonucleases include restriction endonucleases, meganucleases, TAL effector nucleases (TALENs), zinc finger nucleases, and Cas (CRISPR-associated) effector endonucleases.

Cas endonucleases, either as single effector proteins or in an effector complex with other components, unwind the DNA duplex at the target sequence and optionally cleave at least one DNA strand, as mediated by recognition of the target sequence by a polynucleotide (such as, but not limited to, a crRNA or guide RNA) that is in complex with the Cas endonuclease. Such recognition and cutting of a target sequence by a Cas endonuclease typically occurs if the correct protospacer-adjacent motif (PAM) is located at or adjacent to the 3' end of the DNA target sequence. Alternatively, a Cas endonuclease herein may lack DNA cleavage or nicking activity, but can still specifically bind to a DNA target sequence when complexed with a suitable RNA component. (See also U.S. Patent Application US20150082478 published 19 Mar. 2015 and US20150059010 published 26 Feb. 2015).

Cas endonucleases that have been described include, but are not limited to, for example: Cas3 (a feature of Class 1 type I systems), Cas9 (a feature of Class 2 type II systems) and Cas12 (Cpf1) (a feature of Class 2 type V systems).

Cas9 (formerly referred to as Cas5, Csn1, or Csx12) is a Cas endonuclease that forms a complex with a crNucleotide and a tracrNucleotide, or with a single guide polynucleotide, for specifically recognizing and cleaving all or part of a DNA target sequence. The canonical Cas9 recognizes a 3' GC-rich PAM sequence on the target dsDNA, typically comprising an NGG motif. The Cas endonucleases described herein may recognize additional PAM sequences and used to modify target sites with different recognition sequence specificity.

A Cas9 protein comprises a RuvC nuclease with an HNH (H—N—H) nuclease adjacent to the RuvC-II domain. The RuvC nuclease and HNH nuclease each can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al., 2013, *Cell* 157:1262-1278). Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA (Makarova et al. 2015, *Nature Reviews Microbiology* Vol. 13:1-15).

Cas endonucleases and effector proteins can be used for targeted genome editing (via simplex and multiplex double-strand breaks and nicks) and targeted genome regulation (via tethering of epigenetic effector domains to either the Cas protein or sgRNA. A Cas endonuclease can also be engineered to function as an RNA-guided recombinase, and via RNA tethers could serve as a scaffold for the assembly of multiprotein and nucleic acid complexes (Mali et al., 2013, *Nature Methods* Vol. 10: 957-963).

A Cas9 endonuclease, effector protein, or functional fragment thereof, for use in the disclosed methods, can be isolated from a native source, or from a recombinant source where the genetically modified host cell is modified to express the nucleic acid sequence encoding the protein. Alternatively, the Cas endonuclease protein can be produced using cell free protein expression systems, or be synthetically produced. Cas endonucleases may be isolated and introduced into a heterologous cell, or may be modified from its native form to exhibit a different type or magnitude of activity than what it would exhibit in its native source. Such modifications include, but are not limited to, fragments, variants, substitutions, deletions, and insertions.

Fragments and variants of Cas endonucleases can be obtained via methods such as site-directed mutagenesis and synthetic construction. Methods for measuring endonuclease activity are well known in the art such as, but not limiting to, WO2013166113 published 7 Nov. 2013, WO2016186953 published 24 Nov. 2016, and WO2016186946 published 24 Nov. 2016.

The Cas endonuclease can comprise a modified form of the Cas polypeptide. The modified form of the Cas polypeptide can include an amino acid change (e.g., deletion, insertion, or substitution) that reduces the naturally-occurring nuclease activity of the Cas protein. For example, in some instances, the modified form of the Cas protein has less than 50%, less than 40%, less than 30%, less than 20%, less than 10%, less than 5%, or less than 1% of the nuclease activity of the corresponding wild-type Cas polypeptide (US20140068797 published 6 Mar. 2014). In some cases, the modified form of the Cas polypeptide has no substantial nuclease activity and is referred to as catalytically "inactivated Cas" or "deactivated Cas (dCas)." An inactivated Cas/deactivated Cas includes a deactivated Cas endonuclease (dCas). A catalytically inactive Cas endonuclease can be fused to a heterologous sequence to induce or modify activity.

A Cas endonuclease can be part of a fusion protein comprising one or more heterologous protein domains (e.g., 1, 2, 3, or more domains in addition to the Cas protein. Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas can also be fused to a FokI nuclease to generate double-strand breaks (Guilinger et al. *Nature Biotechnology*, volume 32, number 6, June 2014). In some aspects, the Cas endonuclease is a fusion protein further comprising a nuclease domain, a transcriptional activator domain, a transcriptional repressor domain, an epigenetic modification domain, a cleavage domain, a nuclear localization signal, a cell-penetrating domain, a translocation domain, a marker, or a transgene that is heterologous to the target polynucleotide sequence or to the cell from which said target polynucleotide sequence is obtained or derived. In some aspects, the nuclease fusion protein comprises Clo51 or Fok1.

The Cas endonucleases described herein can be expressed and purified by methods known in the art, for example as described in WO/2016/186953 published 24 Nov. 2016.

In some aspects, one or more Cas endonuclease is a Cas9 endonuclease. Some exemplary Cas9 endonucleases are described, for example, in WO/2019/165168 published 29 Aug. 2019.

A Cas endonuclease can comprise a heterologous nuclear localization sequence (NLS). A heterologous NLS amino acid sequence herein may be of sufficient strength to drive accumulation of a Cas protein in a detectable amount in the nucleus of a yeast cell herein, for example.

In some aspects of the methods disclosed herein, the Cas endonuclease is a Cas-alpha endonuclease, such as Cas12f, or an artificial variant thereof. Some exemplary Cas-alpha endonucleases are described in, for example, U.S. Ser. No. 10/934,536 and WO2022082179.

A Cas-alpha endonuclease is a functional RNA-guided, PAM-dependent dsDNA cleavage protein of fewer than 800 amino acids, comprising: a C-terminal RuvC catalytic domain split into three subdomains and further comprising bridge-helix and one or more Zinc finger motif(s); and an N-terminal Rec subunit with a helical bundle, WED wedge-like (or "Oligonucleotide Binding Domain", OBD) domain, and, optionally, a Zinc finger motif.

Cas-alpha endonucleases comprise one or more Zinc Finger (ZFN) coordination motif(s) that may form a Zinc binding domain. Zinc Finger-like motifs can aid in target and non-target strand separation and loading of the guide RNA into the DNA target. Cas-alpha endonucleases comprising one or more Zinc Finger motifs can provide additional stability to a ribonucleoprotein complex on a target polynucleotide. Cas-alpha endonucleases comprise C4 or C3H zinc binding domains.

A Cas-alpha endonuclease can function as a double-strand-break-inducing agent, a single-strand-break inducing agent, or as a nickase. In some aspects, a catalytically inactive Cas-alpha endonuclease can be used to target or recruit to a target DNA sequence but not induce cleavage. In some aspects, a catalytically inactive Cas-alpha protein can be combined with a base editing molecule, such as a cytidine deaminase or an adenine deaminase.

A Cas-alpha endonuclease, effector protein, or functional fragment thereof, can be used in the disclosed methods for targeted genome editing.

Protospacer Adjacent Motif (PAM)

A "protospacer adjacent motif" (PAM) herein refers to a short nucleotide sequence adjacent to a target sequence (protospacer) that can be recognized (targeted) by a guide polynucleotide/Cas endonuclease system. In some aspects, the Cas endonuclease may not successfully recognize a target DNA sequence if the target DNA sequence is not adjacent to, or near, a PAM sequence. In some aspects, the PAM precedes the target sequence (e.g., Cas12a). In some aspects, the PAM follows the target sequence (e.g. *S. pyogenes* Cas9). The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

A "randomized PAM" and "randomized protospacer adjacent motif" are used interchangeably herein, and refer to a random DNA sequence adjacent to a target sequence (protospacer) that is recognized (targeted) by a guide polynucleotide/Cas endonuclease system. The randomized PAM sequence can be of any length but is typically 1, 2, 3, 4, 5, 6, 7, 8, 9, 10, 11, 12, 13, 14, 15, 16, 17, 18, 19 or 20 nucleotides long. A randomized nucleotide includes anyone of the nucleotides A, C, G or T.

Many Cas endonucleases have been described to date that can recognize specific PAM sequences (WO2016186953 published 24 Nov. 2016, WO2016186946 published 24 Nov. 2016, and Zetsche B et al. 2015. Cell 163, 1013) and cleave the target DNA at a specific position. It is understood that based on the methods and embodiments described herein utilizing a novel guided Cas system one skilled in the art can now tailor these methods such that they can utilize any guided endonuclease system.

Guide Polynucleotides

The guide polynucleotide enables target recognition, binding, and optionally cleavage by the Cas endonuclease, and can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (US20150082478 published 19 Mar. 2015 and US20150059010 published 26 Feb. 2015). A guide polynucleotide may be engineered or synthetic.

The guide polynucleotide includes a chimeric non-naturally occurring guide RNA comprising regions that are not found together in nature (i.e., they are heterologous with respect to each other). For example, a chimeric non-naturally occurring guide RNA comprising a first nucleotide sequence domain (referred to as Variable Targeting domain or VT domain) that can hybridize to a nucleotide sequence in a target DNA, linked to a second nucleotide sequence that can recognize the Cas endonuclease, such that the first and second nucleotide sequence are not found linked together in nature.

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences.

In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides.

The tracrRNA (trans-activating CRISPR RNA) comprises, in the 5'-to-3' direction, (i) an "anti-repeat" sequence that anneals with the repeat region of CRISPR type II crRNA and (ii) a stem loop-comprising portion (Deltcheva et al., *Nature* 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) into the target site. (US20150082478 published 19 Mar. 2015 and US20150059010 published 26 Feb. 2015). In some embodiments, the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides.

In one embodiment, the RNA that guides the RNA/Cas endonuclease complex is a duplexed RNA comprising a duplex crRNA-tracrRNA.

In one aspect, the guide polynucleotide is a guide polynucleotide capable of forming a PGEN as described herein, wherein said guide polynucleotide comprises a first nucleotide sequence domain that is complementary to a nucleotide sequence in a target DNA, and a second nucleotide sequence domain that interacts with said Cas endonuclease polypeptide.

In one aspect, the guide polynucleotide is a guide polynucleotide described herein, wherein the first nucleotide sequence and the second nucleotide sequence domain is selected from the group consisting of a DNA sequence, a RNA sequence, and a combination thereof.

In one aspect, the guide polynucleotide is a guide polynucleotide described herein, wherein the first nucleotide sequence and the second nucleotide sequence domain is selected from the group consisting of RNA backbone modifications that enhance stability, DNA backbone modifications that enhance stability, and a combination thereof (see Kanasty et al., 2013, Common RNA-backbone modifications, *Nature Materials* 12:976-977; US20150082478 published 19 Mar. 2015 and US20150059010 published 26 Feb. 2015)

The guide RNA includes a dual molecule comprising a chimeric non-naturally occurring crRNA linked to at least one tracrRNA. A chimeric non-naturally occurring crRNA includes a crRNA that comprises regions that are not found together in nature (i.e., they are heterologous with each other. For example, a crRNA comprising a first nucleotide sequence domain (referred to as Variable Targeting domain or VT domain) that can hybridize to a nucleotide sequence in a target DNA, linked to a second nucleotide sequence (also referred to as a tracr mate sequence) such that the first and second sequence are not found linked together in nature.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide.

The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) the target site. (US20150082478 published 19 Mar. 2015 and US20150059010 published 26 Feb. 2015).

A chimeric non-naturally occurring single guide RNA (sgRNA) includes a sgRNA that comprises regions that are not found together in nature (i.e., they are heterologous with each other. For example, a sgRNA comprising a first nucleotide sequence domain (referred to as Variable Targeting domain or VT domain) that can hybridize to a nucleotide sequence in a target DNA linked to a second nucleotide sequence (also referred to as a tracr mate sequence) that are not found linked together in nature.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide (also referred to as "loop") can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

The guide polynucleotide can be produced by any method known in the art, including chemically synthesizing guide polynucleotides (such as but not limiting to Hendel et al. 2015, *Nature Biotechnology* 33, 985-989), in vitro generated guide polynucleotides, and/or self-splicing guide RNAs (such as but not limited to Xie et al. 2015, *PNAS* 112:3570-3575).

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161). This strategy has been successfully applied in cells of several different species including maize and soybean (US 20150082478, published on Mar. 19, 2015). Methods for expressing RNA components that do not have a 5' cap have been described (WO 2016/025131, published on Feb. 18, 2016).

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas9 system that can form a complex with a type II Cas9 endonuclease, wherein said guide RNA/Cas9 endonuclease complex can direct the Cas9 endonuclease to a DNA target site, enabling the Cas9 endonuclease to recognize, bind to, and optionally nick or cleave (introduce a single or double strand break) the DNA target site.

Single guide RNAs targeting a target site in the genome of an organism can be designed by changing the Variable Targeting Domain (VT) of any of the guide polynucleotides described herein, with any random nucleotide that can hybridize to any desired target sequence.

In some embodiments, a subject nucleic acid (e.g., a guide polynucleotide, a nucleic acid comprising a nucleotide sequence encoding a guide polynucleotide; a nucleic acid encoding Cas9 endonuclease of the present disclosure; a crRNA or a nucleotide encoding a crRNA, a tracrRNA or a nucleotide encoding a tracrRNA, a nucleotide encoding a VT domain, a nucleotide encoding a CER domain, etc.) comprises a modification or sequence that provides for an additional desirable feature (e.g., modified or regulated stability; subcellular targeting; tracking, e.g., a fluorescent label; a binding site for a protein or protein complex; etc.). Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

Functional variants of a guide polynucleotide of the present disclosure can comprise a modified guide polynucleotide wherein the modification comprises adding, removing, or otherwise altering loops and/or hairpins in the single guide RNA.

Functional variants of a guide polynucleotide of the present disclosure can comprise a modified guide polynucleotide wherein the modification comprises one or more modified nucleotides in the nucleotide sequence, wherein the one or more modified nucleotides comprises at least one non-naturally-occurring nucleotide, nucleotide mimetic (as described in US application US2014/0068797, published Mar. 6, 2014), or analog thereof, or wherein the one or more modified nucleotides are selected from the group consisting of 2'-0-methylanalogs, 2'-fluoro analogs 2-aminopurine, 5-bromo-uridine, pseudouridine, and 7-methylguanosine.

In one aspect, the functional variant of the guide RNA can form a guide RNA/Cas9 endonuclease complex that can recognize, bind to, and optionally nick or cleave a target sequence.

Guide Polynucleotide/Cas Endonuclease Complexes

A guide polynucleotide/Cas endonuclease complex described herein is capable of recognizing, binding to, and optionally nicking, unwinding, or cleaving all or part of a target sequence.

A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas protein disclosed herein), or a variant thereof retaining some or all activity in each endonuclease domain of the Cas protein, is a suitable example of a Cas endonuclease that can cleave both strands of a DNA target sequence.

A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas nickase may comprise (i) a mutant, dysfunctional RuvC domain and (ii) a functional HNH domain (e.g., wild type HNH domain). As another example, a Cas nickase may comprise (i) a functional RuvC domain (e.g., wild type RuvC domain) and (ii) a mutant, dysfunctional HNH domain. Non-limiting examples of Cas nickases suitable for use herein are disclosed in US20140189896 published on 3 Jul. 2014. A pair of Cas nickases can be used to increase the specificity of DNA targeting. In general, this can be done by providing two Cas nickases that, by virtue of being associated with RNA components with different guide sequences, target and nick nearby DNA sequences on opposite strands in the region for desired targeting. Such nearby cleavage of each DNA strand creates a double-strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least 5, between 5 and 10, at least 10, between 10 and 15, at least 15, between 15 and 20, at least 20, between 20 and 30, at least 30, between 30 and 40, at least 40, between 40 and 50, at least 50, between 50 and 60, at least 60, between 60 and 70, at least 70, between 70 and 80, at least 80, between 80 and 90, at least 90, between 90 and 100, or 100 or greater (or any number between 5 and 100) bases apart from each other, for example. One or two Cas nickase proteins herein can be used in a Cas nickase pair. For example, a Cas nickase with a mutant RuvC domain, but functioning HNH domain (i.e., Cas HNH+/RuvC−), can be used (e.g., *Streptococcus pyogenes* Cas HNH+/RuvC−). Each Cas nickase (e.g., Cas HNH+/RuvC−) can be directed to specific DNA sites nearby each other (up to 100 base pairs apart) by using suitable RNA components herein with guide RNA sequences targeting each nickase to each specific DNA site.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas protein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein).

In one embodiment of the disclosure, the guide polynucleotide/Cas endonuclease complex is a guide polynucleotide/Cas endonuclease complex (PGEN) comprising at least one guide polynucleotide and at least one Cas endonuclease polypeptide. In some aspects, the Cas endonuclease polypeptide comprises at least one protein subunit of another Cas protein, or a functional fragment thereof, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.

In some aspects, the PGEN is a ribonucleoprotein complex (RNP), wherein the Cas endonuclease is provided as a protein and the guide polynucleotide is provided as a ribonucleotide.

In one embodiment of the disclosure, the guide polynucleotide/Cas effector complex is a guide polynucleotide/Cas endonuclease complex (PGEN) comprising at least one guide polynucleotide and a Cas endonuclease, wherein said guide polynucleotide/Cas endonuclease complex is capable of recognizing, binding to, and optionally nicking, unwinding, or cleaving all or part of a target sequence.

The PGEN can be a guide polynucleotide/Cas endonuclease complex, wherein said Cas endonuclease further comprises one copy or multiple copies of at least one protein subunit, or a functional fragment thereof, of an additional Cas protein.

In one aspect, the guide polynucleotide/Cas endonuclease complex (PGEN) described herein is a PGEN, wherein said Cas endonuclease is covalently or non-covalently linked to at least one Cas protein subunit, or functional fragment thereof. The PGEN can be a guide polynucleotide/Cas endonuclease complex, wherein said Cas endonuclease polypeptide is covalently or non-covalently linked or assembled to one copy or multiple copies of at least one protein subunit, or a functional fragment thereof, of a Cas protein selected from the group consisting of a Cas1 protein subunit, a Cas2 protein subunit, a Cas4 protein subunit, and any combination thereof, in some aspects effectively forming a cleavage ready Cascade. The PGEN can be a guide polynucleotide/Cas endonuclease complex, wherein said Cas endonuclease is covalently or non-covalently linked or assembled to at least two different protein subunits of a Cas protein selected from the group consisting of a Cas1, a Cas2, and Cas4. The PGEN can be a guide polynucleotide/Cas endonuclease complex, wherein said Cas endonuclease is covalently or non-covalently linked to at least three different protein subunits, or functional fragments thereof, of a Cas protein selected from the group consisting of a Cas1, a Cas2, and Cas4, and any combination thereof.

Any component of the guide polynucleotide/Cas endonuclease complex, the guide polynucleotide/Cas endonuclease complex itself, as well as the polynucleotide modification template(s) and/or donor DNA(s), can be introduced into a heterologous cell or organism by any method known in the art.

Some uses for guide RNA/Cas9 endonuclease systems include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods and compositions are provided herein for the chemical modification or alteration of one or more nucleobases of a target polynucleotide, to change the base(s) from one type to another, for example from a Cytosine to a Thymine or an Adenine to a Guanine, using an RNA-guided Cas endonuclease that has been modified to lack double- or single-strand cleaving activity.

Base Editing

One or more nucleobases of a target polynucleotide can be chemically altered, in some cases to change the base from one type to another, for example from a Cytosine to a Thymine, or an Adenine to a Guanine. In some aspects, a plurality of bases, for example 2 or more, 5 or more, 10 or more, 20 or more, 30 or more, 40 or more, 50 or more, 60 or more, 70 or more, 80 or more 90 or more, 100 or more, or even greater than 100, 200 or more, up to thousands of bases may be modified or altered, to produce a plant with a plurality of modified bases.

Any base editing complex, such as a base editing agent associated with an RNA-guided protein, may be used to target and bind to a desired locus in the genome of an organism and chemically modify one or more components of a target polynucleotide.

Site-specific base conversions can be achieved to engineer one or more nucleotide changes to create one or more edits into the genome. These include for example, a site-specific base edit mediated by an C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. A catalytically "dead" or inactive Cas9 (dCas9), for example a catalytically inactive "dead" version of a Cas endonuclease disclosed herein, fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA. Any molecule that effects a change in a nucleobase is a "base editing agent".

For many traits of interest, the creation of single double-strand breaks and the subsequent repair via HDR or NHEJ is not ideal for quantitative traits. An observed phenotype includes both genotype effects and environmental effects. The genotype effects further comprise additive effects, dominance effects, and epistatic effects. The probability of no effect per any single edit can be greater than zero, and any single phenotypic effect can be small, depending on the method used and site selected. Double-stranded break repair can additionally be "noisy" and have low repeatability.

One approach to ameliorate the probability of no effect per edit or small phenotypic effect outcome is to multiplex genome modification, such that a plurality of target sites are modified. Methods to modify a genomic sequence that do not introduce double-strand breaks would allow for single base substitutions. Combining these approaches, multiplexed base editing is beneficial for creating large numbers of genotype edits that can produce observable phenotype modifications. In some cases, dozens or hundreds or thousands of sites can be edited within one or a few generations of an organism.

A multiplexed approach to base editing in an organism, has the potential to create a plurality of significant phenotypic variations in one or a few generations, with a positive directional bias to the effects. In some aspects, the organism is a plant. A plant or a population of plants with a plurality of edits can be cross-bred to produce progeny plants, some of which will comprise multiple pluralities of edits from the parental lines. In this way, accelerated breeding of desired traits can be accomplished in parallel in one or a few generations, replacing time-consuming traditional sequential crossing and breeding across multiple generations.

A base editing deaminase, such as a cytidine deaminase or an adenine deaminase, may be fused to an RNA-guided endonuclease that can be deactivated ("dCas", such as a deactivated Cas9) or partially active ("nCas", such as a Cas9 nickase) so that it does not cleave a target site to which it is guided. The dCas forms a functional complex with a guide polynucleotide that shares homology with a polynucleotide sequence at the target site, and is further complexed with the deaminase molecule. The guided Cas endonuclease recognizes and binds to a double-stranded target sequence, opening the double-strand to expose individual bases. In the case of a cytidine deaminase, the deaminase deaminates the cytosine base and creates a uracil. Uracil glycosylase inhibitor (UGI) is provided to prevent the conversion of U back to C. DNA replication or repair mechanisms then convert the Uracil to a thymine (U to T), and subsequent repair of the opposing base (formerly G in the original G-C pair) to an Adenine, creating a T-A pair. For example, see Komor et al. Nature Volume 533, Pages 420-424, 19 May 2016.

In some aspects of the disclosure, a cell or cells can be incubated with the an engineered deaminase described herein at a temperature of about 23° C. to about 37° C., alternatively about 24° C. to about 37° C., alternatively about 25° C. to about 37° C., alternatively about 26° C. to about 37° C., alternatively about 27° C. to about 37° C., alternatively about 28° C. to about 37° C., alternatively about 29° C. to about 37° C., alternatively about 30° C. to about 37° C., alternatively about 31° C. to about 37° C., alternatively about 32° C. to about 37° C., alternatively about 33° C. to about 37° C., alternatively about 34° C. to about 37° C., alternatively about 35° C. to about 37° C., alternatively about 36° C. to about 37° C., alternatively about 37° C.

In some aspects of the disclosure, a cell or cells can be incubated with an engineered deaminase described herein for a duration of about 2 hours to about 48 hours, alternatively about 5 hours to about 48 hours, alternatively about 10 hours to about 48 hours, alternatively about 15 hours to about 48 hours, alternatively about 20 hours to about 48 hours, alternatively about 25 hours to about 48 hours, alternatively about 30 hours to about 48 hours, alternatively about 35 hours to about 48 hours, alternatively about 40 hours to about 48 hours, alternatively about 45 hours to about 48 hours, alternatively about 48 hours.

Evaluation and Selection of Target Sites

The length of the DNA sequence at the target site can vary, and includes, for example, target sites that are at least 12, 13, 14, 15, 16, 17, 18, 19, 20, 21, 22, 23, 24, 25, 26, 27, 28, 29, 30, or more than 30 nucleotides in length. It is further possible that the target site can be palindromic, that is, the sequence on one strand reads the same in the opposite direction on the complementary strand.

Any cell genome can be evaluated for potential target sites for multiplexed base editing. In one non-limiting example, an elite inbred line of a particular plant is selected, wherein the elite inbred line displays one or more desirable phenotypes. However, the elite inbred line may further comprise some alleles that can be optimized. Candidate editing sites are selected via one of several methods that identifies such optimizable alleles, that may be neutral or deleterious in the original genome but positive, beneficial, or desirable after editing, such as with a deaminase base editor.

Any approach or combination of approaches may be used to find candidate sites in a genome for multiple site editing, for example but not limited to: evolutionary conservation, computational functional prediction, or candidate QTNs identified from experimentation or the literature. Because single edit effects are likely to be small, multiplexing of the edits is an important feature. In some cases, individual phenotypes affected may not be obvious, but fitness association would likely impact yield components of a plant.

In one approach, calculations of evolutionary conservation of individual nucleotides are performed and evaluated, such as Genomic Evolutionary Rate Profiling (GERP), which is a method for producing position-specific estimates of evolutionary constraint using maximum likelihood evolutionary rate estimation. Several "constrained elements" where multiple positions combine to give a signal that is indicative of a putative functional element are identified; this track shows the position-specific scores only, not the element predictions. Constraint intensity at each individual alignment position is quantified in terms of a "rejected substitutions" (RS) score, defined as the number of substitutions expected under neutrality minus the number of substitutions "observed" at the position.

Genomic sites for potential editing are scored independently. Positive scores represent a substitution deficit (i.e., fewer substitutions than the average neutral site) and thus indicate that a site may be under evolutionary constraint. Negative scores indicate that a site is probably evolving neutrally; negative scores should not be interpreted as evidence of accelerated rates of evolution because of too many strong confounders, such as alignment uncertainty or rate variance. Positive scores scale with the level of constraint, such that the greater the score, the greater the level of evolutionary constraint inferred to be acting on that site.

Potential sites for selection for editing, including base editing, are made of alleles at evolutionarily conserved loci that display nucleotide positions that are different than the consensus across multiple genomes. In plants, incomplete dominance of deleterious alleles contributes to trait variation and heterosis in maize.

In another method, candidate edits can be selected based on attention-based predictor network algorithms. Sites with a mutation increasing expression levels of a gene are more conserved, while sites with a mutation decreasing expression levels of a gene are less conserved. For example, conserved sites with a particular allele that has predicted regulatory effects could be one target for base editing.

Identification of candidate alleles for editing can be, for example but not limited to, non-conserved bases in a particular cell line at a conserved (polymorphic) site, bases producing nonsense codons, and/or predicted rare nonsynonymous high impact substitutions.

Recombinant Constructs for Transformation of Cells

The disclosed guide polynucleotides, Cas endonucleases, deaminases, and guide various molecular systems disclosed herein, and any one combination thereof, optionally further comprising one or more polynucleotide(s) or polypeptide(s) of interest, can be introduced into a cell. Cells include, but are not limited to, human, non-human, animal, bacterial, fungal, insect, yeast, non-conventional yeast, and plant cells as well as plants and seeds produced by the methods described herein.

Standard recombinant DNA and molecular cloning techniques used herein are well known in the art and are described more fully in Sambrook et al., *Molecular Cloning. A Laboratory Manual; Cold Spring Harbor Laboratory*: Cold Spring Harbor, NY (1989). Transformation methods are well known to those skilled in the art and are described infra.

Vectors and constructs include circular plasmids, and linear polynucleotides, comprising a polynucleotide of interest and optionally other components including linkers, adapters, regulatory or analysis. In some examples a recognition site and/or target site can be comprised within an intron, coding sequence, 5' UTRs, 3' UTRs, and/or regulatory regions.

Components for Expression and Utilization of CRISPR-Cas Systems in Prokaryotic and Eukaryotic Cells The invention further provides expression constructs for expressing in a prokaryotic or eukaryotic cell/organism a guide RNA/Cas system that is capable of recognizing, binding to, and optionally nicking, unwinding, or cleaving all or part of a target sequence.

In one embodiment, the expression constructs of the disclosure comprise a promoter operably linked to a nucleotide sequence encoding a Cas gene (or optimized sequence, including a Cas endonuclease gene described herein) and a promoter operably linked to a guide RNA of the present disclosure. The promoter is capable of driving expression of an operably linked nucleotide sequence in a prokaryotic or eukaryotic cell/organism.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

Expression Elements

Any polynucleotide encoding a Cas endonuclease, guide RNA, or other CRISPR system component disclosed herein may be functionally linked to a heterologous expression element, to facilitate transcription or regulation in a host cell. Such expression elements include but are not limited to: promoter, leader, intron, and terminator. Expression elements may be "minimal"—meaning a shorter sequence derived from a native source, that still functions as an expression regulator or modifier. Alternatively, an expression element may be "optimized"-meaning that its polynucleotide sequence has been altered from its native state in order to function with a more desirable characteristic in a particular host cell. Alternatively, an expression element may be "synthetic"—meaning that it is designed in silico and synthesized for use in a host cell. Synthetic expression elements may be entirely synthetic, or partially synthetic (comprising a fragment of a naturally-occurring polynucleotide sequence).

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). This strategy has been successfully applied in cells of several different species including maize and soybean (US20150082478 published 19 Mar. 2015). Methods for expressing RNA components that do not have a 5' cap have been described (WO2016/025131 published 18 Feb. 2016).

Optimization of Sequences for Expression in Plants

Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

Polynucleotides of Interest

Polynucleotides of interest may be endogenous to the organism being edited, or maybe provided as heterologous molecules to the organism.

General categories of polynucleotides of interest include, for example, genes of interest involved in information, such as zinc fingers, those involved in communication, such as kinases, and those involved in housekeeping, such as heat shock proteins. More specific polynucleotides of interest include, but are not limited to, genes involved in crop yield, grain quality, crop nutrient content, starch and carbohydrate quality and quantity as well as those affecting kernel size, sucrose loading, protein quality and quantity, nitrogen fixation and/or utilization, fatty acid and oil composition, genes encoding proteins conferring resistance to abiotic stress (such as drought, nitrogen, temperature, salinity, toxic metals or trace elements, or those conferring resistance to molecules such as pesticides or herbicides), genes encoding proteins conferring resistance to biotic stress (such as attacks by fungi, viruses, bacteria, insects, or nematodes, and development of diseases associated with these organisms).

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch.

Polynucleotide sequences of interest may encode proteins involved in providing disease or pest resistance. By "disease resistance" or "pest resistance" is intended that the plants avoid the harmful symptoms that are the outcome of the plant-pathogen interactions.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS, also referred to as acetohydroxyacid synthase, AHAS), in particular the sulfonylurea (UK: sulphonylurea) type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and 9,187,762. The bar gene encodes resistance to the herbicide basta, the nptII gene encodes resistance to the antibiotics kanamycin and geneticin, and the ALS-gene mutants encode resistance to the herbicide chlorsulfuron.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that comprises it, often under particular conditions. These markers can encode an activity, such as, but not limited to, production of RNA, peptide, or protein, or can provide a binding site for RNA, peptides, proteins, inorganic and organic compounds or compositions and the like.

Introduction of CRISPR-Cas System Components into a Cell

The methods and compositions described herein do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a nucleic acid, protein or polynucleotide-protein complex (PGEN, RGEN) to the cell.

Methods for introducing polynucleotides or polypeptides or a polynucleotide-protein complex into cells or organisms are known in the art including, but not limited to, microinjection, electroporation, stable transformation methods, transient transformation methods, ballistic particle acceleration (particle bombardment), whiskers mediated transformation, *Agrobacterium*-mediated transformation, direct gene transfer, viral-mediated introduction, transfection, transduction, cell-penetrating peptides, mesoporous silica nanoparticle (MSN)-mediated direct protein delivery, topical applications, sexual crossing, sexual breeding, and any combination thereof.

For example, the guide polynucleotide (guide RNA, crNucleotide+tracrNucleotide, guide DNA and/or guide RNA-DNA molecule) can be introduced into a cell directly (transiently) as a single stranded or double stranded polynucleotide molecule. The guide RNA (or crRNA+tracrRNA) can also be introduced into a cell indirectly by introducing a recombinant DNA molecule comprising a heterologous nucleic acid fragment encoding the guide RNA (or crRNA+tracrRNA), operably linked to a specific promoter that is capable of transcribing the guide RNA (crRNA+tracrRNA molecules) in said cell. The specific promoter can be, but is not limited to, a RNA polymerase III promoter, which allow for transcription of RNA with precisely defined, unmodified, 5'- and 3'-ends (Ma et al., 2014, *Mol. Ther. Nucleic Acids* 3:e161; DiCarlo et al., 2013, *Nucleic Acids Res.* 41: 4336-4343; WO2015026887, published 26 Feb. 2015). Any promoter capable of transcribing the guide RNA in a cell can be used and includes a heat shock/heat inducible promoter operably linked to a nucleotide sequence encoding the guide RNA.

The Cas endonuclease, such as the Cas endonuclease described herein, can be introduced into a cell by directly introducing the Cas polypeptide itself (referred to as direct delivery of Cas endonuclease), the mRNA encoding the Cas protein, and/or the guide polynucleotide/Cas endonuclease complex itself, using any method known in the art. The Cas endonuclease can also be introduced into a cell indirectly by introducing a recombinant DNA molecule that encodes the Cas endonuclease. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in WO2016073433 published 12 May 2016. Any promoter capable of expressing the Cas endonuclease in a cell can be used and includes a heat shock/heat inducible promoter operably linked to a nucleotide sequence encoding the Cas endonuclease.

Direct delivery of a polynucleotide modification template into plant cells can be achieved through particle mediated delivery, and any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in eukaryotic cells, such as plant cells.

Direct delivery of any one of the guided Cas system components can be accompanied by direct delivery (co-delivery) of other mRNAs that can promote the enrichment and/or visualization of cells receiving the guide polynucleotide/Cas endonuclease complex components. For example, direct co-delivery of the guide polynucleotide/Cas endonuclease components (and/or guide polynucleotide/Cas endonuclease complex itself) together with mRNA encoding phenotypic markers (such as but not limiting to transcriptional activators such as CRC (Bruce et al. 2000 *The Plant Cell* 12:65-79) can enable the selection and enrichment of cells without the use of an exogenous selectable marker by restoring function to a non-functional gene product as described in WO2017070032 published 27 Apr. 2017.

Introducing a guide RNA/Cas endonuclease complex described herein, into a cell includes introducing the individual components of said complex either separately or combined into the cell, and either directly (direct delivery as RNA for the guide and protein for the Cas endonuclease and Cas protein subunits, or functional fragments thereof) or via recombination constructs expressing the components (guide RNA, Cas endonuclease, Cas protein subunits, or functional fragments thereof). Introducing a guide RNA/Cas endonuclease complex (RGEN) into a cell includes introducing the guide RNA/Cas endonuclease complex as a ribonucleotide-protein into the cell. The ribonucleotide-protein can be assembled prior to being introduced into the cell as described herein. The components comprising the guide RNA/Cas endonuclease ribonucleotide protein (at least one Cas endonuclease, at least one guide RNA, at least one Cas protein subunits) can be assembled in vitro or assembled by any means known in the art prior to being introduced into a cell (targeted for genome modification as described herein).

Plant cells differ from human and animal cells in that plant cells comprise a plant cell wall which may act as a barrier to the direct delivery of the RGEN ribonucleoproteins and/or of the direct delivery of the RGEN components.

Direct delivery of the RGEN ribonucleoproteins into plant cells can be achieved through particle mediated delivery (particle bombardment. Based on the experiments described herein, a skilled artesian can now envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RGEN ribonucleoproteins into plant cells.

Direct delivery of the RGEN ribonucleoprotein, allows for genome editing at a target site in the genome of a cell which can be followed by rapid degradation of the complex, and only a transient presence of the complex in the cell. This transient presence of the RGEN complex may lead to reduced off-target effects. In contrast, delivery of RGEN components (guide RNA, Cas endonuclease) via plasmid DNA sequences can result in constant expression of RGENs from these plasmids which can intensify off target effects (Cradick, T. J. et al. (2013) *Nucleic Acids Res* 41:9584-9592; Fu, Y et al. (2014) *Nat. Biotechnol.* 31:822-826).

Direct delivery can be achieved by combining any one component of the guide RNA/Cas endonuclease complex (RGEN) (such as at least one guide RNA, at least one Cas protein, and at least one Cas protein), with a particle delivery matrix comprising a microparticle (such as but not limited to of a gold particle, tungsten particle, and silicon carbide whisker particle) (see also WO2017070032 published 27 Apr. 2017).

In one aspect, the guide polynucleotide/Cas endonuclease complex is a complex wherein the guide RNA and Cas endonuclease protein forming the guide RNA/Cas endonuclease complex are introduced into the cell as RNA and protein, respectively.

In one aspect, the guide polynucleotide/Cas endonuclease complex is a complex wherein the guide RNA and Cas endonuclease protein and the at least one protein subunit of a Cas protein forming the guide RNA/Cas endonuclease complex are introduced into the cell as RNA and proteins, respectively.

In one aspect, the guide polynucleotide/Cas endonuclease complex is a complex wherein the guide RNA and Cas endonuclease protein and the at least one protein subunit of a Cascade forming the guide RNA/Cas endonuclease complex (cleavage ready cascade) are preassembled in vitro and introduced into the cell as a ribonucleotide-protein complex.

Protocols for introducing polynucleotides, polypeptides or polynucleotide-protein complexes (PGEN, RGEN) into eukaryotic cells, such as plants or plant cells are known.

Alternatively, polynucleotides may be introduced into plant or plant cells by contacting cells or organisms with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

The polynucleotide or recombinant DNA construct can be provided to or introduced into a prokaryotic and eukaryotic cell or organism using a variety of transient transformation methods. Such transient transformation methods include, but are not limited to, the introduction of the polynucleotide construct directly into the plant.

Nucleic acids and proteins can be provided to a cell by any method including methods using molecules to facilitate the uptake of anyone or all components of a guided Cas system (protein and/or nucleic acids), such as cell-penetrating peptides and nanocarriers. See also US20110035836 published 10 Feb. 2011, and EP2821486A1 published 7 Jan. 2015.

Other methods of introducing polynucleotides into a prokaryotic and eukaryotic cell or organism or plant part can be used, including plastid transformation methods, and the methods for introducing polynucleotides into tissues from seedlings or mature seeds.

Stable transformation is intended to mean that the nucleotide construct introduced into an organism integrates into a genome of the organism and is capable of being inherited by the progeny thereof. Transient transformation is intended to mean that a polynucleotide is introduced into the organism and does not integrate into a genome of the organism or a polypeptide is introduced into an organism. Transient transformation indicates that the introduced composition is only temporarily expressed or present in the organism.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The presently disclosed polynucleotides and polypeptides can be introduced into a cell. Cells include, but are not limited to, human, non-human, animal, mammalian, bacterial, protist, fungal, insect, yeast, non-conventional yeast, and plant cells, as well as plants and seeds produced by the methods described herein. In some aspects, the cell of the organism is a reproductive cell, a somatic cell, a meiotic cell, a mitotic cell, a stem cell, or a pluripotent stem cell.

Cells and Plants

The presently disclosed polynucleotides and polypeptides can be introduced into a plant cell. Plant cells include, well as plants and seeds produced by the methods described herein. Any plant can be used with the compositions and methods described herein, including monocot and dicot plants, and plant elements.

The novel Cas endonucleases disclosed may be used to edit the genome of a plant cell in various ways. In one aspect, it may be desirable to delete one or more nucleotides. In another aspect, it may be desirable to insert one or more nucleotides. In one aspect, it may be desirable to replace one or more nucleotides. In another aspect, it may be desirable to modify one or more nucleotides via a covalent or non-covalent interaction with another atom or molecule. In some aspects, the cell is diploid. In some aspects, the cell is haploid.

Genome modification via a Cas endonuclease may be used to effect a genotypic and/or phenotypic change on the target organism. Such a change is preferably related to an improved trait of interest or an agronomically-important characteristic, the correction of an endogenous defect, or the expression of some type of expression marker. In some aspects, the trait of interest or agronomically-important characteristic is related to the overall health, fitness, or fertility of the plant, the yield of a plant product, the ecological fitness of the plant, or the environmental stability of the plant. In some aspects, the trait of interest or agronomically-important characteristic is selected from the group consisting of: agronomics, herbicide resistance, insecticide resistance, disease resistance, nematode resistance, microbial resistance, fungal resistance, viral resistance, fertility or sterility, grain characteristics, commercial product production. In some aspects, the trait of interest or agronomically-important characteristic is selected from the group consisting of: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered starch content, altered carbohydrate content, altered sugar content, altered fiber content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum* species, for example *Triticum aestivum, Triticum monococcum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses.

Examples of dicot plants that can be used include, but are not limited to, soybean (*Glycine max*), *Brassica* species (for example but not limited to: oilseed rape or Canola) (*Brassica napus, B. campestris, Brassica rapa, Brassica juncea*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum, Gossypium barbadense*), and peanut (*Arachis hypogaea*), tomato (*Solanum lycopersicum*), potato (*Solanum tuberosum*).

Additional plants that can be used include safflower (*Carthamus tinctorius*), sweet potato (*Ipomoea batatus*), cassava (*Manihot esculenta*), coffee (*Coffea* spp.), coconut (*Cocos nucifera*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), vegetables, ornamentals, and conifers.

Vegetables that can be used include tomatoes (*Lycopersicon esculentum*), lettuce (e.g., *Lactuca saliva*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be used include pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*).

In certain embodiments of the disclosure, a fertile plant is a plant that produces viable male and female gametes and is self-fertile. Such a self-fertile plant can produce a progeny plant without the contribution from any other plant of a gamete and the genetic material comprised therein. Other embodiments of the disclosure can involve the use of a plant that is not self-fertile because the plant does not produce male gametes, or female gametes, or both, that are viable or otherwise capable of fertilization.

The present disclosure finds use in the breeding of plants comprising one or more edited alleles created by the methods or compositions disclosed herein. In some aspects, the edited alleles influence the phenotypic expression of one or more traits, such as plant health, growth, or yield. In some aspects, two plants may be crossed via sexual reproduction to create progeny plant(s) that comprise some or all of the edits from both parental plants.

Cells and Animals

The presently disclosed polynucleotides and polypeptides can be introduced into an animal cell. Animal cells can include, but are not limited to: an organism of a phylum including chordates, arthropods, mollusks, annelids, cnidarians, or echinoderms; or an organism of a class including mammals, insects, birds, amphibians, reptiles, or fishes. In some aspects, the animal is human, mouse, *C. elegans*, rat, fruit fly (*Drosophila* spp.), zebrafish, chicken, dog, cat, guinea pig, hamster, chicken, Japanese ricefish, sea lamprey, pufferfish, tree frog (e.g., *Xenopus* spp.), monkey, or chimpanzee. Particular cell types that are contemplated include haploid cells, diploid cells, reproductive cells, neurons, muscle cells, endocrine or exocrine cells, epithelial cells, muscle cells, tumor cells, embryonic cells, hematopoietic cells, bone cells, germ cells, somatic cells, stem cells, pluripotent stem cells, induced pluripotent stem cells, progenitor cells, meiotic cells, and mitotic cells. In some aspects, a plurality of cells from an organism may be used.

The novel Cas endonucleases disclosed may be used to edit the genome of an animal cell in various ways. In one aspect, it may be desirable to delete one or more nucleotides. In another aspect, it may be desirable to insert one or more nucleotides. In one aspect, it may be desirable to replace one or more nucleotides. In another aspect, it may be desirable to modify one or more nucleotides via a covalent or non-covalent interaction with another atom or molecule.

Genome modification via a Cas endonuclease may be used to effect a genotypic and/or phenotypic change on the target organism. Such a change is preferably related to an improved phenotype of interest or a physiologically-important characteristic, the correction of an endogenous defect, or the expression of some type of expression marker. In some aspects, the phenotype of interest or physiologically-important characteristic is related to the overall health, fitness, or fertility of the animal, the ecological fitness of the animal, or the relationship or interaction of the animal with other organisms in its environment. In some aspects, the phenotype of interest or physiologically-important characteristic is selected from the group consisting of: improved general health, disease reversal, disease modification, disease stabilization, disease prevention, treatment of parasitic infections, treatment of viral infections, treatment of retroviral infections, treatment of bacterial infections, treatment of neurological disorders (for example but not limited to: multiple sclerosis), correction of endogenous genetic defects (for example but not limited to: metabolic disorders, Achondroplasia, Alpha-1 Antitrypsin Deficiency, Antiphospholipid Syndrome, Autism, Autosomal Dominant Polycystic Kidney Disease, Barth syndrome, Breast cancer, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis Imperfecta, Parkinson's disease, Phenylketonuria, Poland Anomaly, *Porphyria*, Progeria, Prostate Cancer, Retinitis Pigmentosa, Severe Combined Immunodeficiency (SCID), Sickle cell disease, Skin Cancer, Spinal Muscular Atrophy, Tay-Sachs, Thalassemia, Trimethylaminuria, Turner Syndrome, Velocardiofacial Syndrome, WAGR Syndrome, and Wilson Disease), treatment of innate immune disorders (for example but not limited to: immunoglobulin subclass deficiencies), treatment of acquired immune disorders (for example but not limited to: AIDS and other HIV-related disorders), treatment of cancer, as well as treatment of diseases, including rare or "orphan" conditions, that have eluded effective treatment options with other methods.

Cells that have been genetically modified using the compositions or methods disclosed herein may be transplanted to a subject for purposes such as gene therapy, e.g., to treat a disease, or as an antiviral, antipathogenic, or anticancer therapeutic, for the production of genetically modified organisms in agriculture, or for biological research.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific embodiments of some aspects of the invention. The examples are offered for illustrative purposes only, and are not intended to limit the scope of the invention in any way.

Although maize was used for exemplary purposes, the methods described herein may be utilized for any organism, such as any plant, such as any monocot or dicot.

Example 1: Identification of Novel tRNA Adenine Deaminases

In this example, bioinformatic methods for identifying novel adenosine deaminases are described.

Figure 2:
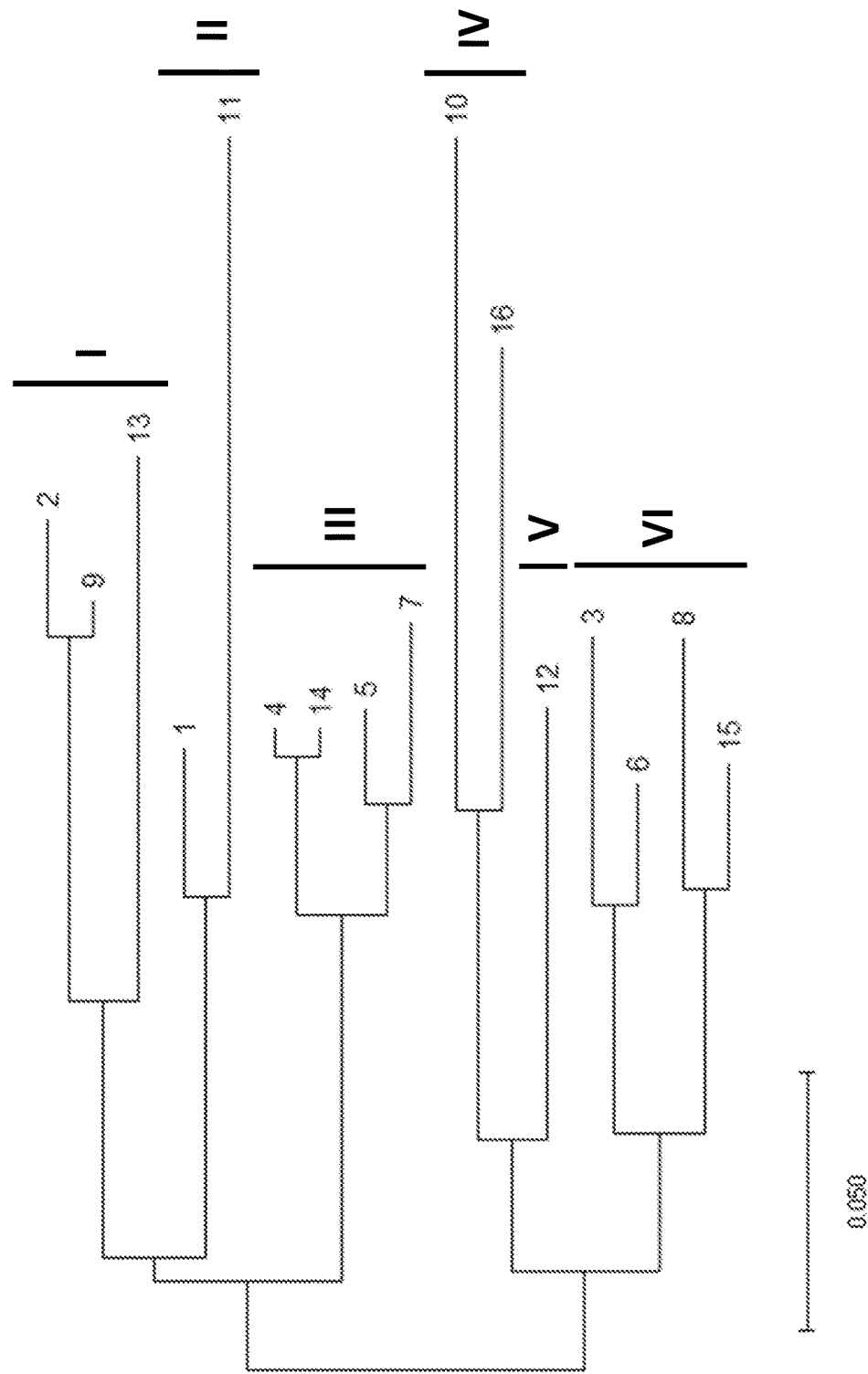
FIG. 2 depicts the phylogenetic relationship among deaminase sequences. Arabic numbers represent SEQ ID numbers, and Roman numerals indicate phylogenetic clades.

In one approach, the prokaryotic tRNA tadA deaminase from *Escherichia coli* (Wolf, J. et al. (2002) *EMBO J.* 21: 3841-3851) (SEQ ID NO:1) was used as a query in PSI-BLAST (Altschul, S. F. et al. (1997) *Nucleic Acids Res.* 25:3389-3402). The resulting deaminases were aligned using Clustal Omega (Sievers, F. et al. (2011) *Molecular Systems Biology.* 7:539) and 15 selected (SEQ ID NO: 2-16) to be within 78-85% amino acid identity of the *E. coli* deaminase (SEQ ID NO: 1) (FIG. 1). The phylogenetic relationship of the deaminases was also evaluated using MEGA7 (Kumar, S. et al. (2016) *Mol. Biol. Evol.* 33, 1870-1874) employing Neighbor-Joining (Saitou, N. et al. (1987) *Mol. Biol. Evol.* 4:406-425) and Poisson correction (Zuckerkandl, E. et al. (1965) *Evol. Genes Proteins.* 97:97-166) methods (FIG. 2).

Example 2: Engineering Novel Deoxyadenosine Deaminases

In this example, methods to engineer novel adenosine deaminases to modify a DNA substrate are described.

Figure 3:
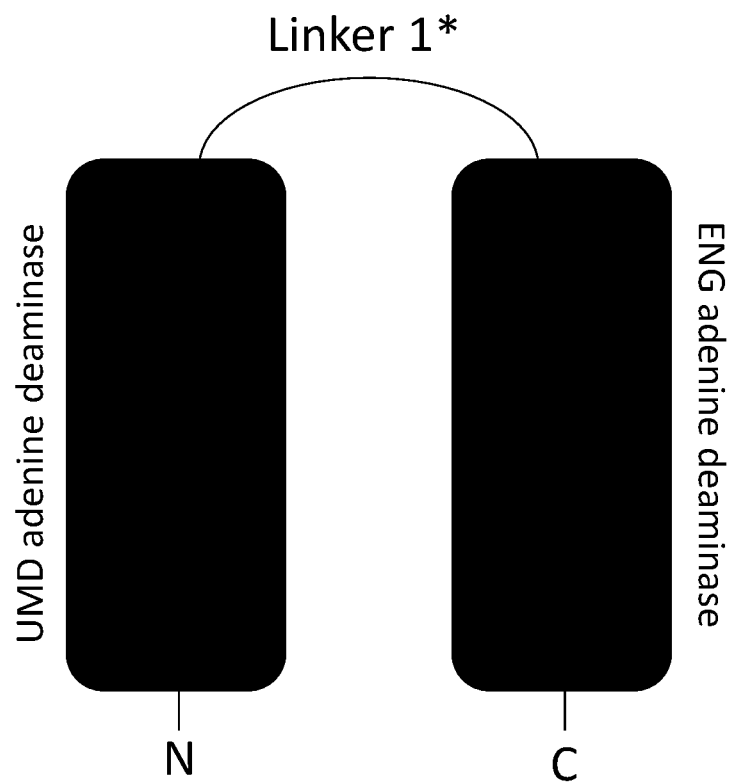
FIG. 3 depicts an engineered heterodimer, comprising both unmodified (UMD) and engineered (ENG) subunits.

Prokaryotic tadA deaminases function to modify the adenosine ribonucleotide to inosine in the anti-codon of tRNAs (Wolf, J. et al. (2002) *EMBO J.* 21: 3841-3851). To convert the adenosine deaminases described herein into an enzyme capable of converting deoxyadenosine to inosine, they were engineered as heterodimers, altogether, comprising both unmodified (UMD) (SEQ ID NOs: 2-16) and engineered (ENG) (SEQ ID NOs: 17-31) subunits (FIG. 3). The ENG subunit was generated by introducing 14 amino acid substitutions to modify the active site to accept deoxyadenosine substrate and fused to the UMD subunit with a linker to generate the final heterodimer (FIG. 3). The resulting heterodimeric deoxyadenosine deaminases (DD) are listed in Table 1.

TABLE 1

Novel heterodimeric deoxyadenosine deaminases (DDs) described herein. UMD(unmodified) and ENG (engineered) fused with a linker constitute the final DD sequence.

| Name | UMD SEQ ID NO: | Linker SEQ ID NO: | ENG SEQ ID NO: | DD SEQ ID NO: |
|---|---|---|---|---|
| DD1 | 2 | 32 | 17 | 33 |
| DD2 | 3 | 32 | 18 | 34 |
| DD3 | 4 | 32 | 19 | 35 |
| DD4 | 5 | 32 | 20 | 36 |
| DD5 | 6 | 32 | 21 | 37 |
| DD6 | 7 | 32 | 22 | 38 |
| DD7 | 8 | 32 | 23 | 39 |
| DD8 | 9 | 32 | 24 | 40 |
| DD9 | 10 | 32 | 25 | 41 |
| DD10 | 11 | 32 | 26 | 42 |
| DD11 | 12 | 32 | 27 | 43 |
| DD12 | 13 | 32 | 28 | 44 |
| DD13 | 14 | 32 | 29 | 45 |
| DD14 | 15 | 32 | 30 | 46 |
| DD15 | 16 | 32 | 31 | 47 |

Example 3: DNA Expression Cassettes for Targeted Deoxyadenosine Base Editing

In this Example, methods to optimize polynucleotide cassettes for the expression of CRISPR-associated (Cas) protein(s), guide RNA (gRNA), and novel deoxyadenosine deaminase(s) in a cell are described. In some aspects, said cell is a plant cell. In one example of a plant cell, a *Zea mays* cell is used.

In one method, a gene encoding the novel deoxyadenosine deaminase was plant codon optimized and gene destabilizing features (for example but not limited to MITEs (Miniature Inverted-repeat Transposable Elements) were removed. The resulting open-reading-frame (ORF) was then optionally fused in-frame to the end of a gene also conditioned for expression that encodes a Cas protein(s) capable of RNA guided recognition of a double-stranded (ds) DNA target site. In some cases, the cas gene encoded a functional, impaired, or dead nuclease. In other circumstances, additional sequences encoding accessory protein(s) that aid in the conversion of a deaminated nucleotide to a different one were also optimized for expression and attached to the cas gene. In some instances, the cas gene encoded a Cas9, Type I Cascade, Cas-alpha, Type V-U, Cas14, or Cas12f protein. An intron was also inserted into the resulting cas-deaminase gene to eliminate expression in *E. coli* or *Agrobacterium* prior to plant transformation. Additionally, to facilitate efficient entry into the nucleus, a sequence encoding a nuclear localization signal (NLS) (for example but not limited to a Simian Virus 40 (NLS)) was incorporated into the deaminase, cas, or accessory gene.

Figure 4:
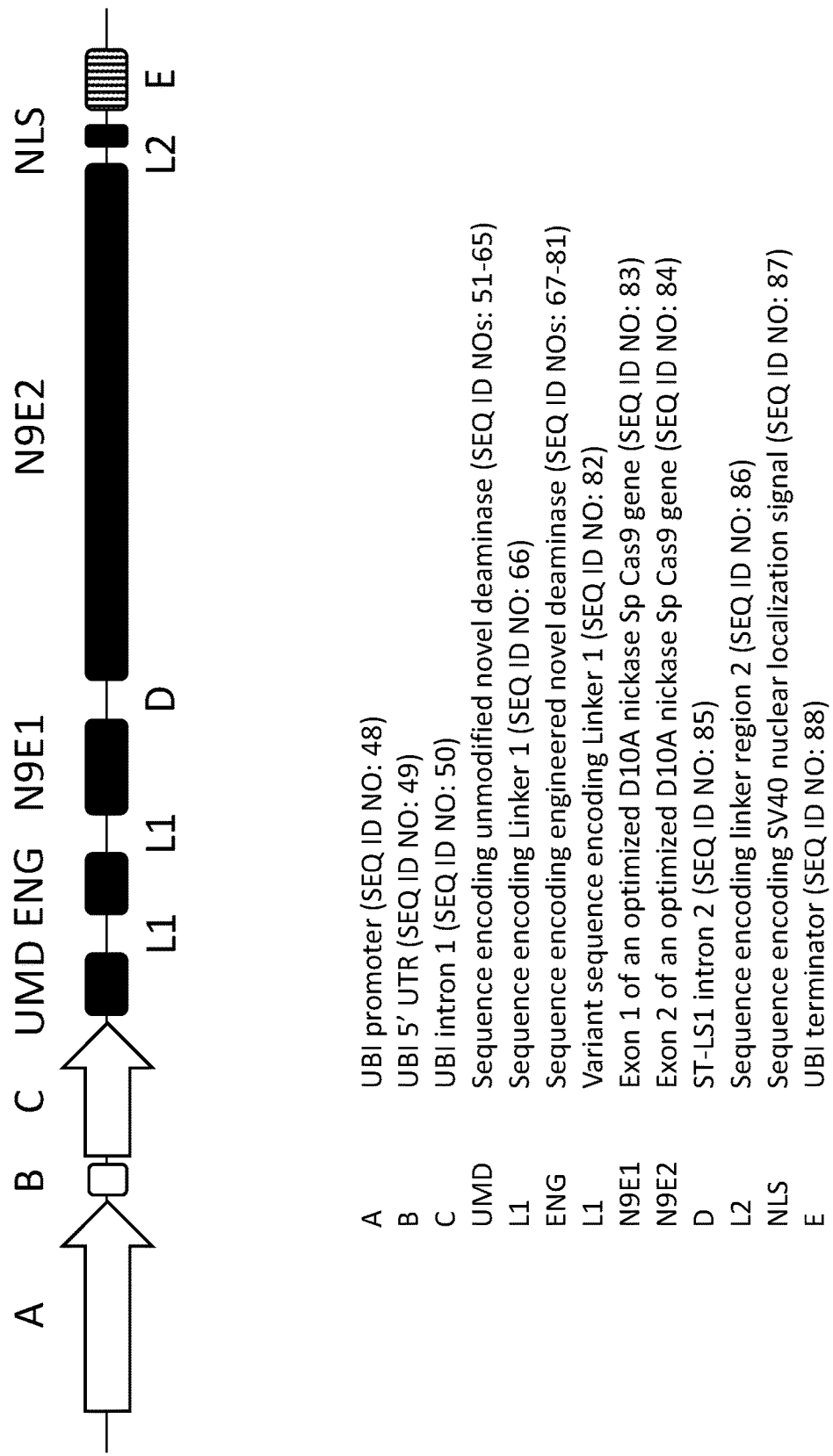
FIG. 4 depicts one example of an optimized novel deaminase expression construct.

The resulting genes engineered for plant cell expression and nuclear localization were next synthesized (for example but not limited to GenScript, Inc.) and operably cloned into a plasmid DNA vector containing an upstream promoter and downstream terminator using standard techniques (for example but not limited to Golden Gate or Gibson assembly (Potapov, V. et al. (2018) *ACS Synth. Biol.* 7:2665-2674 and Gibson, D. et al. (2010) *Science.* 329:52-56). In some instances, the promoter can be a constitutive, spatially or temporally regulated, or inducible. An example of a plant optimized novel deaminase expression construct is illustrated in FIG. 4.

Figure 5:
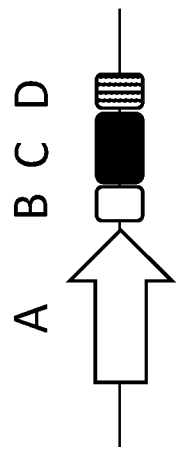
FIG. 5 depicts one example of an optimized guide RNA expression construct.

The deaminase associated Cas complex is directed by small RNAs (referred to herein as guide RNAs) to recognize double-stranded DNA target sites. These guide RNAs (gRNAs) comprise a sequence that aids recognition by the Cas protein (referred to as Cas recognition domain) and a sequence that serves to direct dsDNA target recognition by base pairing with one strand of the DNA target site (Cas variable targeting domain). To transcribe small RNAs necessary for directing base-editing in plant cells, a U6 polymerase III promoter and terminator were first isolated from a plant genome and operably fused to the ends of a suitable guide RNA. To promote optimal transcription of the guide RNA from the U6 polymerase III promoter, a G nucleotide is added to the 5' end of the sequence to be transcribed. Csy4 (Cas6 or CasE) ribonuclease recognition site, a tRNA-based system and heterologous RNAse-based system can also be used to process the guide RNA transcripts. Moreover, the RNA processing provided by these strategies can be harnessed to express multiple guide RNAs from either a single polymerase II or III promoter. An example of a plant optimized gRNA expression construct is illustrated in FIG. 5.

Example 4: Delivery of Components for Targeted Deoxyadenosine Base Editing

In this example, methods for introducing novel deoxyadenosine deaminase(s) and Clustered Regular Interspaced Short Pallindomic Repeat (CRISPR)-associated (Cas) and guide polynucleotide(s) into cells are described. In some aspects, said cell is a plant cell. In one example of a plant cell, a *Zea mays* cell is used.

*Zea mays* Transformation
Particle-Mediated Delivery of DNA Expression Cassettes Particle gun transformation of Hi-Type II 8 to 10-day-old immature maize embryos (IMEs) in the presence of BBM and WUS2 genes was carried-out as described in Svitashev et al. (2015) *Plant Physiology.* 169:931-945. Briefly, DNA expression cassettes were co-precipitated onto 0.6 μM (average size) gold particles utilizing TransIT-2020. Next, the DNA coated gold particles were pelleted by centrifugation, washed with absolute ethanol and re-dispersed by sonication. Following sonication, 10 µl of the DNA coated gold particles were loaded onto a macrocarrier and air dried. Next, biolistic transformation was performed using a PDS-1000/He Gun (Bio-Rad) with a 425 pound per square inch rupture disc. Since particle gun transformation can be highly variable, a visual marker DNA expression cassette encoding a yellow fluorescent protein (YFP) was also co-delivered to aid in the selection of evenly transformed IMEs and each treatment was performed in triplicate. To determine the plant transformation culture conditions optimal for target DNA deamination and repair, transformed IMEs are incubated at 28° C. for 48 hours, or at a range of temperatures lower or higher than 28° C. to establish the temperature optimum for target DNA deamination and repair. Post-bombardment culture, selection, and plant regeneration were performed using methods described previously (Gordon-Kamm, W. et al. (2002) *Proc Natl Acad Sci USA.* 99:11975-11980) except baby boom (bbm) and wuschel2 (wus2) genes were expressed with non-constitutive promoters, maize phospholipid transferase protein (Zm-PLTP) and maize auxin-inducible (Zm-Axig1) promoters, respectively (Lowe, K. et al. (2018) *In Vitro Cellular Dev-Pl.* 54:240-252).

Particle-Mediated Ribonucleoprotein Delivery

Novel deoxyadenosine deaminase, Cas, and associated guide polynucleotide(s) ribonucleoprotein (RNP) complex (es) can be delivered by particle gun transformation as described in Svitashev, S. et al. (2016) *Nat. Commun.* 7:13274. Briefly, RNPs (and optionally DNA expression) are precipitated onto 0.6 mm (average diameter) gold particles (Bio-Rad) using a water soluble cationic lipid TransIT-2020 (Mirus) as follows: 50 ml of gold particles (water suspension of 10 mg/ml) and 2 ml of TransIT-2020 water solution are added to the premixed RNPs (and optionally DNA expression vectors), mixed gently, and incubated on ice for 10 min. RNP/DNA-coated gold particles are then pelleted in a microfuge at 8,000 g for 30 s and supernatant is removed. The pellet is then resuspended in 50 ml of sterile water by brief sonication. Immediately after sonication, coated gold particles are loaded onto a microcarrier (10 ml each) and allowed to air dry. Immature maize embryos, 8-10 days after pollination, are then bombarded using a PDS-1000/He Gun (Bio-Rad) with a rupture pressure of 425 pounds per inch square. Post-bombardment culture, selection, and plant regeneration are performed using methods described previously (Gordon-Kamm, W. et al. 2002) except bbm and wus2 genes were expressed with non-constitutive promoters, Zm-PLTP and Zm-Axig1 promoters, respectively (Lowe, K. et al. 2018).

Agrobacterium-Mediated Transformation

Agrobacterium-mediated transformation is performed essentially as described in Djukanovic et al. (2006) *Plant Biotech J.* 4:345-57 except bbm and wus2 genes were expressed with non-constitutive promoters, Zm-PLTP and Zm-Axig1 promoters, respectively (Lowe, K. et al. 2018). Briefly, 10-12 day old immature embryos (average 2 mm in length) are dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium is replaced with 1 ml *Agrobacterium* at a concentration of 0.35-0.45 OD550. Maize embryos are incubated with *Agrobacterium* for 5 min at room temperature, then the mixture is poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos are incubated axis down, in the dark for 3 days at 21° C., then incubated 4 days in the dark at 28° C. at which time they may be harvested for DNA extraction.

In another variation for stable transformation, the embryos are then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos are subcultured every three weeks until transgenic events are identified. Somatic embryogenesis is induced by transferring a small amount of tissue onto regeneration medium (4.3 g/L MS salts (Gibco 11117), 5.0 ml/L MS Vitamins Stock Solution, 100 mg/L myo-inositol, 0.1 uM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots are transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets are moved into glass tubes containing the same medium and grown until they were sampled and/or transplanted into soil.

Example 5: CRISPR-Cas DNA Target Modification with Novel Deoxyadenosines

In this example, the conversion of deoxyadenosine to deoxyguanine within the vicinity of a Clustered Regular Interspaced Short Palindromic Repeat (CRISPR)-associated (Cas) and guide polynucleotide(s) chromosomal DNA target site(s) using the engineered deoxyadenosine deaminases described herein are described. In some aspects, said chromosomal DNA target site is in a plant. In one example of a plant chromosomal DNA target site, a *Zea mays* chromosomal DNA site is targeted.

In one method, the DNA expression construct illustrated in FIG. 4 was delivered by Particle Gun (PG) transformation into *Zea mays* immature embryos (IEs) as described in Example 4: Particle-mediated delivery of DNA expression cassettes. To direct the Cas9 and novel deoxyadenosine deaminase to a chromosomal DNA target, a sgRNA expression cassette (FIG. 5) was also included. After transformation, IEs were incubated either at 28° C. or 37° C. After four days, the 20-30 most evenly transformed IEs, based on YFP expression and consequential fluorescence (see Example 4), and examined for the presence of changes within the CRISPR-Cas target site similar to that described previously (Karvelis, T. et al. (2015) *Genome Biology.* 16:253 (Methods Section: in planta mutation detection)). Briefly, total genomic DNA was extracted and the region surrounding the intended target site was PCR amplified with Phusion® High Fidelity PCR Master Mix (New England Biolabs, M0531L) adding on the sequences necessary for amplicon-specific barcodes and Illumina sequencing using "tailed" primers through two rounds of PCR and deep sequenced. The resulting reads were then examined for the presence of alterations within and immediately adjacent to the CRISPR-Cas9 target site by comparison to control experiments where the small RNA transcriptional cassette was omitted from the transformation. For *Zea mays* plants regenerated from transformation experiments, a similar method was followed except total genomic DNA was extracted from leaf punches.

Figure 6:
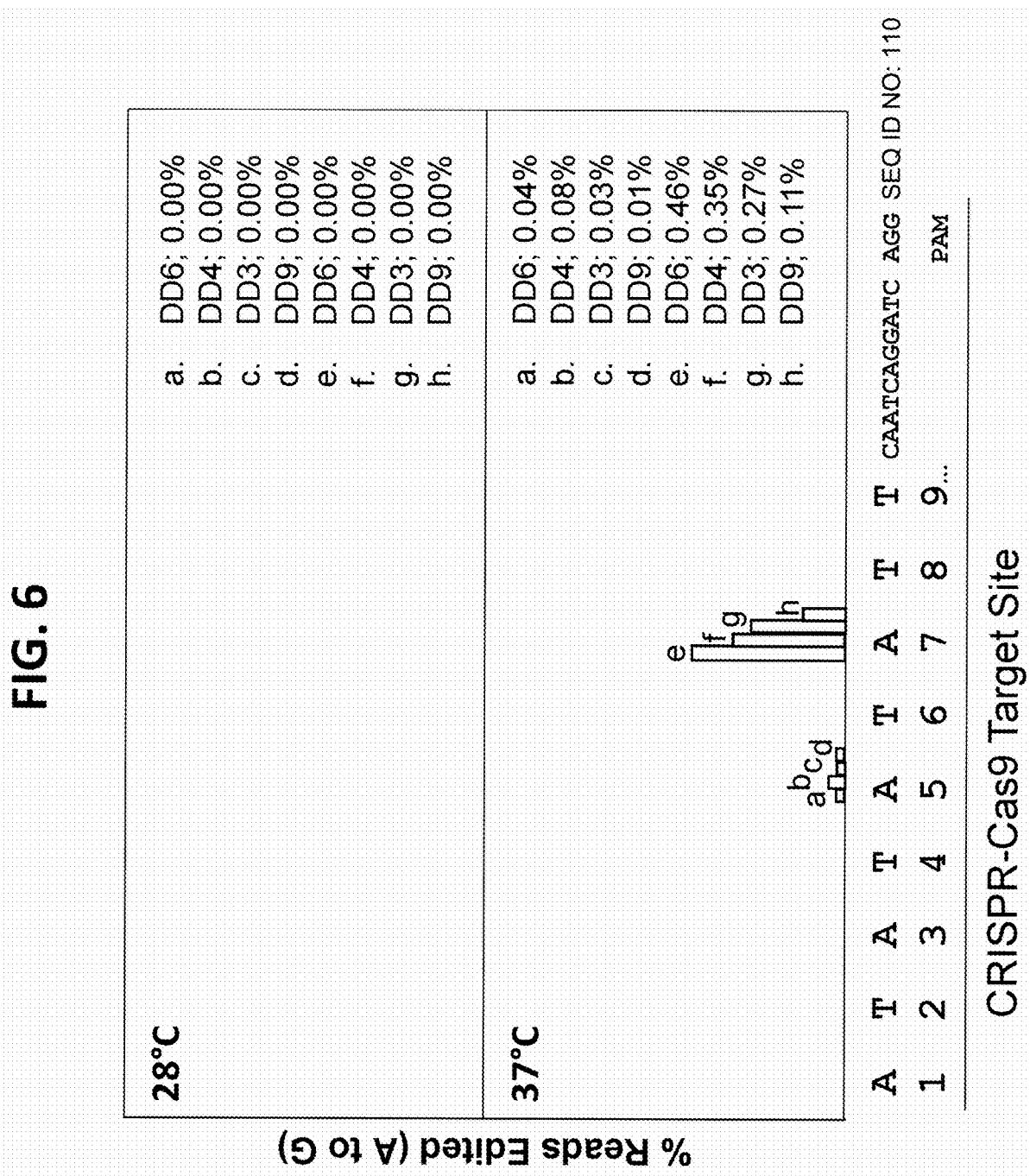
FIG. 6 shows that four of the novel engineered deoxyadenine deaminases produced polymorphisms within the CRISPR-Cas target site.

As shown in FIG. 6, four of the deaminases produced targeted deoxyadenosine (A) to deoxyguanine (G) conversions. Additionally, A to G conversions predominantly occurred at position 7 of the target site and only when the IEs were incubated at 37° C. following PG transformation. Phylogenetic analysis showed that the 3 most active deoxyadenine deaminases were related and from clade III (FIG. 2).

Multiple sequence alignment (MSAPRobs (Liu, Y. et. al. (2010) *Bioinformatics*. 26:1958-1964)) showed a distinct C-terminal motif (AESCSAMLSDFFRWRREEKKA[L/Q][K/R]KAR) (SEQ ID NO: 109) for the deaminases from clade III (FIG. 7). This motif was highly conserved and had three uniquely conserved residues S140-W150-R163 (FIG. 7). Secondary structure predictions (PSIPRED (Jones, J. T. (1999) *J. Mol. Biol.* 292:195-202)) and a study of the adenosine deaminase from *Trypanosoma brucei* (Ragone et al. (2011) *RNA*. 17:1296-1306) suggested that this motif corresponds to an extension of the fifth α-helix in the protein, termed α5', that may enhance substrate binding (FIG. 7).

To extend our findings from a plant cell to an entire plant, *Zea mays* cells transformed with a Cas9 linked deoxyadenosine deaminase (DD3, DD4, or DD6) and sgRNA expression constructs were cultured, selected and plants regenerated as described in Example 4: Particle-mediated delivery of DNA expression cassettes. Due to the observed temperature sensitivity (FIG. 6), experiments were assembled with and without a 4 day long 37° C. heat shock following transformation. As shown in FIG. 8 and Table 2, plantlets containing an A to G bp conversion with the Cas9 target site were recovered in all experiments. Additionally, no other alterations (e.g., insertion of deletion mutations) were observed at the CRISPR-Cas9 target. DD6 yielded the highest frequency of editing (in the 37° C. heat shock) that totaled 80% (12 of the 15 plants) (FIG. 8 and Table 2). Of these, 67% (10 plants) exhibited biallelic base editing (identified by the near equal presence of two editing outcomes or the presence of a single editing pattern with greatly reduced frequency (<5%) of unmodified sequence (Table 2)) within the CRISPR-Cas9 target site (FIG. 8). The remaining plants (2) from the DD6 heat shock experiment were heterozygous (determined by the observance of a near equal frequency of edited and unmodified sequences (Table 2)) (FIG. 8). This can be contrasted with the 28° C. (no heat shock) treatment where just 23% (3 out of 13) of the plants showed base editing with the majority of outcomes being heterozygous (FIG. 8 and Table 2). The impact of the heat shock on the editing efficiency for the DD4 construct was less notable with a near identical frequency of base editing recovered between experiments (FIG. 8 and Table 2). Like DD6, DD3 also showed enhanced editing in the 37° C. treatment, however, its overall frequencies of editing were lower than either DD6 and DD4 (FIG. 8 and Table 2).

In general, the position of editing within the CRISPR-Cas9 target site for DD6, DD4 and DD3 showed a strong preference for the $7^{th}$ position (FIG. 9). Out of the total editing observed and independent of the experiment, the frequency of A to G bp conversion was restricted to only the $7^{th}$ position for DD4 and DD3 (FIG. 9). DD6 exhibited temperature dependence in the position of editing (FIG. 9). Here, 28° C. treatments yielded editing at only the $7^{th}$ position while the 37° C. treatment produced A to G bp modifications at both $5^{th}$ and $7^{th}$ positions (FIG. 9).

TABLE 2

Cas9 and sgRNA directed deoxyadenosine deaminase induced A to G base editing in maize plants as assessed by examining the proportion of modified and unmodified sequence reads. To register as a base edited plant, A to G bp modified sequence reads totaling more than 10% of the total read depth were required.

| Treatment | Plant ID | Allele 1 Base Editing Frequency | Allele 2 Base Editing Frequency | Frequency of Unmodified |
|---|---|---|---|---|
| DD6; 37° C. Heat Shock | 20.META334.1.B.1 | 49% | 50% | 1% |
| | 20.META334.1.B.2 | — | — | 100% |
| | 20.META334.1.B.3 | 52% | — | 48% |
| | 20.META334.1.B.4 | 50% | 48% | 2% |
| | 20.META334.1.B.5 | 48% | 52% | — |
| | 20.META334.1.B.6 | 48% | 52% | — |
| | 20.META334.1.B.7 | 47% | 53% | — |
| | 20.META334.1.B.8 | 53% | — | 47% |
| | 20.META334.1.B.9 | 51% | 48% | 1% |
| | 20.META334.1.B.10 | 49% | 49% | 2% |
| | 20.META334.1.B.11 | 53% | — | 47% |
| | 20.META334.1.B.12 | — | — | 100% |
| | 20.META334.1.B.13 | 49% | 50% | 1% |
| | 20.META334.1.B.14 | — | — | 100% |
| | 20.META334.1.B.15 | 50% | 49% | 1% |
| DD6; No Heat Shock | 20.META334.1.F.1 | — | — | 100% |
| | 20.META334.1.F.2 | — | — | 100% |
| | 20.META334.1.F.3 | — | — | 100% |
| | 20.META334.1.F.4 | — | — | 100% |
| | 20.META334.1.F.5 | — | — | 100% |
| | 20.META334.1.F.6 | — | — | 100% |
| | 20.META334.1.F.7 | — | — | 100% |
| | 20.META334.1.F.8 | 2% | — | 98% |
| | 20.META334.1.F.9 | 54% | — | 46% |
| | 20.META334.1.F.10 | 99% | — | 1% |
| | 20.META334.1.F.11 | 48% | 52% | — |
| | 20.META334.1.F.12 | 7% | 2% | 91% |
| | 20.META334.1.F.13 | — | — | 100% |

TABLE 2-continued

Cas9 and sgRNA directed deoxyadenosine deaminase induced A to G base editing in maize plants as assessed by examining the proportion of modified and unmodified sequence reads. To register as a base edited plant, A to G bp modified sequence reads totaling more than 10% of the total read depth were required.

| Treatment | Plant ID | Allele 1 Base Editing Frequency | Allele 2 Base Editing Frequency | Frequency of Unmodified |
|---|---|---|---|---|
| DD4; 37° C. Heat Shock | 20.META334.1.C.1 | 55% | — | 45% |
| | 20.META334.1.C.2 | 54% | — | 46% |
| | 20.META334.1.C.3 | 100% | — | 0% |
| | 20.META334.1.C.4 | — | — | 100% |
| | 20.META334.1.C.5 | — | — | 100% |
| | 20.META334.1.C.6 | — | — | 100% |
| | 20.META334.1.C.7 | 51% | — | 49% |
| | 20.META334.1.C.8 | — | — | 100% |
| | 20.META334.1.C.9 | — | — | 100% |
| DD4; No Heat Shock | 20.META334.1.G.1 | 59% | — | 41% |
| | 20.META334.1.G.2 | 4% | — | 96% |
| | 20.META334.1.G.3 | — | — | 100% |
| | 20.META334.1.G.4 | 50% | — | 50% |
| | 20.META334.1.G.5 | 51% | — | 49% |
| | 20.META334.1.G.6 | — | — | 100% |
| | 20.META334.1.G.7 | — | — | 100% |
| | 20.META334.1.G.8 | — | — | 100% |
| | 20.META334.1.G.9 | 51% | — | 49% |
| | 20.META334.1.G.10 | 51% | — | 49% |
| | 20.META334.1.G.11 | 50% | — | 50% |
| | 20.META334.1.G.12 | — | — | 100% |
| | 20.META334.1.G.13 | — | — | 100% |
| | 20.META334.1.G.14 | 6% | — | 92% |
| | 20.META334.1.G.15 | — | — | 100% |
| | 20.META334.1.G.16 | — | — | 100% |
| | 20.META334.1.G.17 | — | — | 100% |
| DD3; 37° C. Heat Shock | 20.META334.1.D.1 | — | — | 100% |
| | 20.META334.1.D.2 | — | — | 100% |
| | 20.META334.1.D.3 | — | — | 100% |
| | 20.META334.1.D.4 | — | — | 100% |
| | 20.META334.1.D.5 | 13% | — | 87% |
| | 20.META334.1.D.6 | — | — | 100% |
| | 20.META334.1.D.7 | — | — | 100% |
| | 20.META334.1.D.8 | — | — | 100% |
| DD3; No Heat Shock | 20.META334.1.H.1 | — | — | 100% |
| | 20.META334.1.H.2 | — | — | 100% |
| | 20.META334.1.H.3 | — | — | 100% |
| | 20.META334.1.H.4 | — | — | 100% |
| | 20.META334.1.H.5 | — | — | 100% |
| | 20.META334.1.H.6 | — | — | 100% |
| | 20.META334.1.H.7 | — | — | 100% |
| | 20.META334.1.H.8 | — | — | 100% |
| | 20.META334.1.H.9 | — | — | 100% |
| | 20.META334.1.H.10 | 6% | 2% | 92% |
| | 20.META334.1.H.11 | — | — | 100% |
| | 20.META334.1.H.12 | — | — | 100% |
| | 20.META334.1.H.13 | — | — | 100% |
| | 20.META334.1.H.14 | — | — | 100% |
| | 20.META334.1.H.15 | — | — | 100% |
| | 20.META334.1.H.16 | — | — | 100% |
| | 20.META334.1.H.17 | — | — | 100% |
| | 20.META334.1.H.18 | — | — | 100% |
| | 20.META334.1.H.19 | 30% | — | 70% |
| | 20.META334.1.H.20 | — | — | 100% |
| | 20.META334.1.H.21 | — | — | 100% |
| | 20.META334.1.H.22 | 2% | — | 98% |
| | 20.META334.1.H.23 | — | — | 100% |
| | 20.META334.1.H.24 | — | — | 100% |
| | 20.META334.1.D.1 | — | — | 100% |

We claim:

1. An engineered, non-natural deaminase comprising an amino acid sequence having at least 90% identity to SEQ ID NO: 38.

2. The deaminase of claim 1, wherein the deaminase is operably linked or fused with a guided DNA-binding polypeptide.

3. The deaminase of claim 1, wherein the deaminase is operably linked or fused with a guided Cas polypeptide.

4. The deaminase of claim 1, wherein the deaminase is operably linked or fused with a guided Cas polypeptide that lacks double-strand-break-inducing activity and a single strand nickase activity.

5. The deaminase of claim 3, wherein the Cas polypeptide is Type II or Type V.

6. The deaminase of claim 1, wherein the deaminase is an adenine deaminase.

7. A cell comprising the deaminase of claim 1.

8. The cell of claim 7, wherein the cell is an eukaryotic cell.

9. The cell of claim 7, wherein the cell is a plant cell.

10. The engineered deaminase of claim 1, further comprising SEQ ID NO: 109.

* * * * *

SEQUENCE LISTING

<160> NUMBER OF SEQ ID NOS: 110

<210> SEQ ID NO 1

```
<211> LENGTH: 167
<212> TYPE: PRT
<213> ORGANISM: Escherichia coli

<400> SEQUENCE: 1

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165

<210> SEQ ID NO 2
<211> LENGTH: 168
<212> TYPE: PRT
<213> ORGANISM: Enterobacteriaceae bacterium strain FGI 57

<400> SEQUENCE: 2

Met Ser Asp Asn Glu Phe Asn His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val Leu Asp Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Met Val Leu Gln Asn Tyr Arg Leu Ile Asn Ala Thr Leu
65                  70                  75                  80

Tyr Val Thr Leu Glu Pro Cys Val Met Cys Ala Gly Ala Met Val His
                85                  90                  95

Ser Arg Ile Gly His Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Val Thr Glu Gly Val Leu Arg Glu Gln Cys Ala Gly Met
    130                 135                 140

Leu Ser Asp Phe Phe Arg Glu Arg Arg Glu Gln Ile Lys Ala Leu Arg
145                 150                 155                 160

Lys Ala Gln Lys Ala Glu Asn Gln
                165
```

-continued

<210> SEQ ID NO 3
<211> LENGTH: 167
<212> TYPE: PRT
<213> ORGANISM: Kluyvera georgiana

<400> SEQUENCE: 3

Met Ser Asp Ile Glu Gln Asn His Glu Tyr Trp Met Arg His Ala Leu
1               5                   10                  15

Ala Leu Ala Arg Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Val Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Gly Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Ala Asp Glu Cys Ser Ala Met
    130                 135                 140

Leu Ser Asp Phe Phe Arg His Arg Arg Gln Gln Gln Lys Ala Leu Lys
145                 150                 155                 160

Gln Ser Leu Lys Asn Ser Leu
                165

<210> SEQ ID NO 4
<211> LENGTH: 169
<212> TYPE: PRT
<213> ORGANISM: Klebsiella pneumoniae

<400> SEQUENCE: 4

Met Ser Asp Leu Glu Leu Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ala Arg Leu Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Ser Glu Gly Val Leu Ala Glu Ser Cys Ser Ala Met
    130                 135                 140

Leu Ser Asp Phe Phe Arg Trp Arg Arg Glu Glu Lys Lys Ala Gln Lys
145                 150                 155                 160

```
Lys Ala Arg Glu Gln Thr Gly Glu Ser
                165

<210> SEQ ID NO 5
<211> LENGTH: 167
<212> TYPE: PRT
<213> ORGANISM: Klebsiella aerogenes

<400> SEQUENCE: 5

Met Ser Asp His Glu Phe Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Ile Leu Ala Glu Ser Cys Ser Ala Met
    130                 135                 140

Leu Ser Asp Phe Phe Arg Trp Arg Arg Glu Glu Lys Lys Ala Leu Arg
145                 150                 155                 160

Lys Ala Arg Gln Glu Glu Gly
                165

<210> SEQ ID NO 6
<211> LENGTH: 166
<212> TYPE: PRT
<213> ORGANISM: Kluyvera ascorbata ATCC 33433

<400> SEQUENCE: 6

Met Ser Asp Ile Glu Leu Asn His Glu Tyr Trp Met Arg His Ala Leu
1               5                   10                  15

Val Leu Ala Gln Arg Ala Trp Asp Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Gly Arg Ile Gly Asn Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Ala Glu Glu Cys Ser Ala Met
    130                 135                 140
```

-continued

Leu Ser Asp Phe Phe Arg His Arg Gln Gln Gln Lys Ala Leu Arg
145                 150                 155                 160

Gln Ala Glu Lys Gly Ser
                165

<210> SEQ ID NO 7
<211> LENGTH: 168
<212> TYPE: PRT
<213> ORGANISM: Raoultella sp.

<400> SEQUENCE: 7

Met Ser Asp His Glu Arg Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Ile Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Ala Glu Gly Val Leu Ala Glu Ser Cys Ser Ala Met
    130                 135                 140

Leu Ser Asp Phe Phe Arg Trp Arg Glu Glu Lys Lys Ala Leu Lys
145                 150                 155                 160

Lys Ala Arg Gln Ala Asp Glu Ser
                165

<210> SEQ ID NO 8
<211> LENGTH: 167
<212> TYPE: PRT
<213> ORGANISM: Klebsiella sp. RIT-PI-d

<400> SEQUENCE: 8

Met Ser Asp His Glu Leu Asn His Glu His Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Glu Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Ser Arg Ile Gly Gln Leu Val Phe Gly Ala Arg Asp Ala Lys Thr Gly
            100                 105                 110

Ala Ala Gly Ser Leu Ile Asp Ile Leu His His Pro Gly Met Asn His
        115                 120                 125

```
Arg Val Glu Phe Thr Glu Gly Val Leu Lys Asp Thr Cys Ala Thr Leu
    130                 135                 140

Leu Ser Glu Phe Phe Arg His Arg Arg Gln Val Lys Lys Ala Leu Arg
145                 150                 155                 160

Gln Ala Glu Lys Asp Pro Arg
                165
```

<210> SEQ ID NO 9
<211> LENGTH: 168
<212> TYPE: PRT
<213> ORGANISM: Pseudocitrobacter faecalis

<400> SEQUENCE: 9

```
Met Ser Asp Asn Glu Phe Asn His Glu Tyr Trp Met Arg His Ala Leu
1               5                   10                  15

Thr Leu Ala Gln Arg Ala Trp Asp Glu Gly Val Pro Val Gly Ala
                20                  25                  30

Val Leu Val Leu Asp Asn Gln Val Ile Gly Glu Gly Trp Asn Arg Pro
            35                  40                  45

Ile Gly Arg His Asp Pro Thr Ala His Ala Glu Ile Met Ala Leu Arg
    50                  55                  60

Gln Gly Gly Met Val Leu Gln Asn Tyr Arg Leu Ile Asn Ala Thr Leu
65                  70                  75                  80

Tyr Val Thr Leu Glu Pro Cys Val Met Cys Ala Gly Ala Met Val His
                85                  90                  95

Ser Arg Ile Gly Arg Val Val Phe Gly Ala Arg Asp Ala Lys Thr Gly
                100                 105                 110

Ala Ala Gly Ser Leu Met Asp Val Leu His His Pro Gly Met Asn His
            115                 120                 125

Arg Val Glu Val Thr Glu Gly Ile Leu Arg Asp Gln Cys Ala Ser Met
    130                 135                 140

Leu Ser Asp Phe Phe Arg Glu Arg Glu Gln Ile Lys Ala Leu Arg
145                 150                 155                 160

Lys Ala Gln Lys Ala Gly Asn Gln
                165
```

<210> SEQ ID NO 10
<211> LENGTH: 168
<212> TYPE: PRT
<213> ORGANISM: Enterobacter cloacae

<400> SEQUENCE: 10

```
Met Ser Ile Pro Glu Tyr Asn His Glu Tyr Trp Met Arg His Ala Leu
1               5                   10                  15

Thr Leu Ala Gln Arg Ala Trp Asp Glu Gly Glu Val Pro Val Gly Ala
                20                  25                  30

Val Leu Val His Asn Asn Gln Val Ile Gly Glu Gly Trp Asn Arg Pro
            35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Leu Asp Thr Thr Leu
65                  70                  75                  80

Tyr Val Thr Leu Glu Pro Cys Val Met Cys Ser Gly Ala Met Val His
                85                  90                  95

Ser Arg Ile Gly Thr Leu Val Phe Gly Ala Arg Asp Glu Lys Thr Gly
                100                 105                 110
```

```
Ala Ala Gly Ser Leu Met Asp Val Leu Gly His Pro Gly Met Asn His
        115                 120                 125

Gln Val Lys Thr Ile Gly Gly Val Leu Ala Pro Glu Cys Ser Gly Leu
    130                 135                 140

Leu Ser Asp Phe Phe Arg Met Arg Arg Gln Gln Lys Lys Gln Gln Lys
145                 150                 155                 160

Ala Glu Leu Lys Leu Leu Gly Asp
                165
```

<210> SEQ ID NO 11
<211> LENGTH: 164
<212> TYPE: PRT
<213> ORGANISM: Citrobacter youngae

<400> SEQUENCE: 11

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Arg Trp Val Arg
            20                  25                  30

Tyr Trp Tyr Ile Thr Thr Ala Phe Gly Glu Gly Trp Asn Arg Pro Ile
        35                  40                  45

Gly His His Asp Pro Thr Ala His Ala Glu Ile Met Ala Leu Arg Gln
    50                  55                  60

Gly Gly Leu Val Leu Gln Asn Tyr Arg Leu Leu Asp Ala Thr Leu Tyr
65                  70                  75                  80

Val Thr Leu Glu Pro Cys Val Met Cys Ala Gly Ala Met Val His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Asp Val Thr Glu Gly Val Leu Arg Asp Glu Cys Ala Thr Leu Leu
    130                 135                 140

Ser Asp Phe Phe Arg Met Arg Arg Gln Glu Ile Lys Ala Leu Lys Lys
145                 150                 155                 160

Ser Ala Asn Gln
```

<210> SEQ ID NO 12
<211> LENGTH: 169
<212> TYPE: PRT
<213> ORGANISM: Kosakonia pseudosacchari

<400> SEQUENCE: 12

```
Met Ser Ile Pro Glu Leu Asn His Asp Val Trp Met Arg His Ala Leu
1               5                   10                  15

Thr Leu Ala Lys Arg Ala Arg Glu Glu Gly Glu Val Pro Val Gly Ala
            20                  25                  30

Val Leu Val His Asn Gly Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95
```

Ser Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Arg Asp Glu Cys Ala Ala Met
    130                 135                 140

Leu Ser Asp Phe Phe Arg Gln Arg Leu Glu Lys Lys Ala Leu Lys
145                 150                 155                 160

Lys Pro Thr Gly Asp Pro Thr Ala Phe
                165

<210> SEQ ID NO 13
<211> LENGTH: 163
<212> TYPE: PRT
<213> ORGANISM: Pluralibacter gergoviae

<400> SEQUENCE: 13

Met Ser Asp Thr Glu Gln His Glu Tyr Trp Met Arg His Ala Leu Thr
1               5                   10                  15

Leu Ala Arg His Ala Trp Asp Glu Gly Glu Val Pro Val Gly Ala Val
            20                  25                  30

Leu Val His Glu Gly Asn Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Ala Val Leu Gln Asn Tyr Arg Leu Ile Asn Ala Thr Leu Tyr
65                  70                  75                  80

Val Thr Leu Glu Pro Cys Val Met Cys Ala Gly Ala Met Val His Ser
                85                  90                  95

Arg Ile Ala Arg Leu Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Val Leu Gly Ala Glu Cys Ala Ser Leu Leu
    130                 135                 140

Ser Asp Phe Phe Arg Gln Arg Glu Gln Lys Lys Ala Leu Lys Arg
145                 150                 155                 160

Gly Cys Cys

<210> SEQ ID NO 14
<211> LENGTH: 169
<212> TYPE: PRT
<213> ORGANISM: Klebsiella pneumoniae

<400> SEQUENCE: 14

Met Ser Asp Leu Glu Leu Asn Asp Glu Tyr Trp Met Arg His Ala Leu
1               5                   10                  15

Thr Leu Ala Lys Arg Ala Arg Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80

```
Tyr Val Thr Leu Glu Pro Cys Val Met Cys Ala Gly Ala Met Val His
                85                  90                  95

Ser Arg Ile Ala Arg Leu Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Ser Glu Gly Val Leu Ala Glu Ser Cys Ser Ala Met
    130                 135                 140

Leu Ser Asp Phe Phe Arg Trp Arg Glu Glu Lys Lys Ala Leu Lys
145                 150                 155                 160

Lys Ala Arg Glu Gln Thr Gly Glu Ser
                165
```

<210> SEQ ID NO 15
<211> LENGTH: 167
<212> TYPE: PRT
<213> ORGANISM: Superficieibacter electus

<400> SEQUENCE: 15

```
Met Ser Asn His Glu Leu Asn His Glu His Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Asp Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Ser Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Phe Thr Glu Gly Val Leu Gly Glu Glu Cys Ala Ala Leu
    130                 135                 140

Leu Ser Asp Phe Phe Arg His Arg Arg Gln Val Lys Lys Ala Leu Arg
145                 150                 155                 160

Gln Ala Glu Lys Ser Gln Asp
                165
```

<210> SEQ ID NO 16
<211> LENGTH: 173
<212> TYPE: PRT
<213> ORGANISM: Cronobacter malonaticus

<400> SEQUENCE: 16

```
Met Ser Gln Thr Glu Leu Thr His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60
```

```
Gln Gly Gly Leu Val Leu Gln Asn Tyr Arg Leu Leu Asp Thr Thr Leu
65                  70                  75                  80

Tyr Val Thr Leu Glu Pro Cys Val Met Cys Ala Gly Ala Met Val His
                85                  90                  95

Gly Arg Ile Gly Thr Leu Val Phe Gly Ala Arg Asp Ala Lys Thr Gly
            100                 105                 110

Ala Val Gly Ser Leu Met Asp Ile Thr Gly His Pro Gly Met Asn His
            115                 120                 125

Gln Val Gln Val Ile Glu Gly Ile Leu Ala Thr Glu Cys Ser Ala Met
            130                 135                 140

Leu Ser Ala Phe Phe Arg Gln Arg Arg Leu Glu Lys Lys Ala Leu Lys
145                 150                 155                 160

Glu Ala Thr Lys Arg Ala Thr Gly Ser Asp Pro Ala Ala
                165                 170
```

<210> SEQ ID NO 17
<211> LENGTH: 167
<212> TYPE: PRT
<213> ORGANISM: Artificial
<220> FEATURE:
<223> OTHER INFORMATION: Engineered novel adenine deaminase 1

<400> SEQUENCE: 17

```
Ser Asp Asn Glu Phe Asn His Glu Tyr Trp Met Arg His Ala Leu Thr
1               5                   10                  15

Leu Ala Gln Arg Ala Arg Asp Glu Gly Glu Val Pro Val Gly Ala Val
                20                  25                  30

Leu Val Leu Asp Asn Gln Val Ile Gly Glu Gly Trp Asn Arg Ala Ile
            35                  40                  45

Gly Leu His Asp Pro Thr Ala His Ala Glu Ile Met Ala Leu Arg Gln
50                  55                  60

Gly Gly Met Val Leu Gln Asn Tyr Arg Leu Ile Asn Ala Thr Leu Tyr
65                  70                  75                  80

Val Thr Phe Glu Pro Cys Val Met Cys Ala Gly Ala Met Val His Ser
                85                  90                  95

Arg Ile Gly His Val Val Phe Gly Val Arg Asn Ala Lys Thr Gly Ala
            100                 105                 110

Ala Gly Ser Leu Met Asp Val Leu His Tyr Pro Gly Met Asn His Arg
            115                 120                 125

Val Glu Val Thr Glu Gly Val Leu Arg Glu Gln Cys Ala Gly Met Leu
            130                 135                 140

Cys Tyr Phe Phe Arg Glu Pro Arg Glu Val Phe Asn Ala Leu Arg Lys
145                 150                 155                 160

Ala Gln Lys Ala Glu Asn Gln
                165
```

<210> SEQ ID NO 18
<211> LENGTH: 166
<212> TYPE: PRT
<213> ORGANISM: Artificial
<220> FEATURE:
<223> OTHER INFORMATION: Engineered novel adenine deaminase 2

<400> SEQUENCE: 18

```
Ser Asp Ile Glu Gln Asn His Glu Tyr Trp Met Arg His Ala Leu Ala
1               5                   10                  15
```

```
Leu Ala Arg Arg Ala Arg Glu Glu Gly Glu Val Pro Val Gly Ala Val
             20                  25                  30

Leu Val Leu Asn Asn Gln Val Ile Gly Glu Gly Trp Asn Arg Ala Ile
         35                  40                  45

Gly Leu His Asp Pro Thr Ala His Ala Glu Ile Met Ala Leu Arg Gln
 50                  55                  60

Gly Gly Val Val Leu Gln Asn Tyr Arg Leu Ile Asp Thr Thr Leu Tyr
 65                  70                  75                  80

Val Thr Phe Glu Pro Cys Val Met Cys Ala Gly Ala Met Val His Gly
                 85                  90                  95

Arg Ile Gly Gln Leu Val Phe Gly Val Arg Asn Ala Lys Thr Gly Ala
            100                 105                 110

Ala Gly Ser Leu Ile Asp Val Leu His Tyr Pro Gly Met Asn His Arg
        115                 120                 125

Val Glu Ile Thr Glu Gly Val Leu Ala Asp Glu Cys Ser Ala Met Leu
    130                 135                 140

Cys Tyr Phe Phe Arg His Pro Arg Gln Val Phe Asn Ala Leu Lys Gln
145                 150                 155                 160

Ser Leu Lys Asn Ser Leu
                165

<210> SEQ ID NO 19
<211> LENGTH: 168
<212> TYPE: PRT
<213> ORGANISM: Artificial
<220> FEATURE:
<223> OTHER INFORMATION: Engineered novel adenine deaminase 3

<400> SEQUENCE: 19

Ser Asp Leu Glu Leu Asn Asp Glu Tyr Trp Met Arg His Ala Leu Thr
 1               5                  10                  15

Leu Ala Lys Arg Ala Arg Glu Glu Gly Glu Val Pro Val Gly Ala Val
             20                  25                  30

Leu Val Leu Asn Asn Gln Val Ile Gly Glu Gly Trp Asn Arg Ala Ile
         35                  40                  45

Gly Leu His Asp Pro Thr Ala His Ala Glu Ile Met Ala Leu Arg Gln
 50                  55                  60

Gly Gly Leu Val Leu Gln Asn Tyr Arg Leu Ile Asp Ala Thr Leu Tyr
 65                  70                  75                  80

Val Thr Phe Glu Pro Cys Val Met Cys Ala Gly Ala Met Val His Ser
                 85                  90                  95

Arg Ile Ala Arg Leu Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Ser Glu Gly Val Leu Ala Glu Ser Cys Ser Ala Met Leu
    130                 135                 140

Cys Tyr Phe Phe Arg Trp Pro Arg Glu Val Phe Asn Ala Gln Lys Lys
145                 150                 155                 160

Ala Arg Glu Gln Thr Gly Glu Ser
                165

<210> SEQ ID NO 20
<211> LENGTH: 166
<212> TYPE: PRT
<213> ORGANISM: Artificial
```

```
<220> FEATURE:
<223> OTHER INFORMATION: Engineered novel adenine deaminase 4

<400> SEQUENCE: 20

Ser Asp His Glu Phe Asn Asp Glu Tyr Trp Met Arg His Ala Leu Thr
1               5                   10                  15

Leu Ala Lys Arg Ala Arg Glu Glu Gly Glu Val Pro Val Gly Ala Val
            20                  25                  30

Leu Val Leu Asn Asn Gln Val Ile Gly Glu Gly Trp Asn Arg Ala Ile
        35                  40                  45

Gly Leu His Asp Pro Thr Ala His Ala Glu Ile Met Ala Leu Arg Gln
50                  55                  60

Gly Gly Leu Val Leu Gln Asn Tyr Arg Leu Ile Asp Ala Thr Leu Tyr
65                  70                  75                  80

Val Thr Phe Glu Pro Cys Val Met Cys Ala Gly Ala Met Val His Ser
                85                  90                  95

Arg Ile Ser Arg Leu Val Phe Gly Val Arg Asn Ala Lys Thr Gly Ala
            100                 105                 110

Ala Gly Ser Leu Ile Asp Val Leu His Tyr Pro Gly Met Asn His Arg
        115                 120                 125

Val Glu Ile Thr Glu Gly Ile Leu Ala Glu Ser Cys Ser Ala Met Leu
130                 135                 140

Cys Tyr Phe Phe Arg Trp Pro Arg Glu Val Phe Asn Ala Leu Arg Lys
145                 150                 155                 160

Ala Arg Gln Glu Glu Gly
                165

<210> SEQ ID NO 21
<211> LENGTH: 165
<212> TYPE: PRT
<213> ORGANISM: Artificial
<220> FEATURE:
<223> OTHER INFORMATION: Engineered novel adenine deaminase 5

<400> SEQUENCE: 21

Ser Asp Ile Glu Leu Asn His Glu Tyr Trp Met Arg His Ala Leu Val
1               5                   10                  15

Leu Ala Gln Arg Ala Arg Asp Glu Gly Glu Val Pro Val Gly Ala Val
            20                  25                  30

Leu Val Leu Asn Asn Gln Val Ile Gly Glu Gly Trp Asn Arg Ala Ile
        35                  40                  45

Gly Leu His Asp Pro Thr Ala His Ala Glu Ile Met Ala Leu Arg Gln
50                  55                  60

Gly Gly Leu Val Leu Gln Asn Tyr Arg Leu Ile Asp Thr Thr Leu Tyr
65                  70                  75                  80

Val Thr Phe Glu Pro Cys Val Met Cys Ala Gly Ala Met Val His Gly
                85                  90                  95

Arg Ile Gly Asn Leu Val Phe Gly Val Arg Asn Ala Lys Thr Gly Ala
            100                 105                 110

Ala Gly Ser Leu Ile Asp Val Leu His Tyr Pro Gly Met Asn His Arg
        115                 120                 125

Val Glu Ile Thr Glu Gly Val Leu Ala Glu Glu Cys Ser Ala Met Leu
130                 135                 140
```

```
Cys Tyr Phe Phe Arg His Pro Arg Gln Val Phe Asn Ala Leu Arg Gln
145                 150                 155                 160

Ala Glu Lys Gly Ser
                165
```

<210> SEQ ID NO 22
<211> LENGTH: 167
<212> TYPE: PRT
<213> ORGANISM: Artificial
<220> FEATURE:
<223> OTHER INFORMATION: Engineered novel adenine deaminase 6

<400> SEQUENCE: 22

```
Ser Asp His Glu Arg Asn Asp Glu Tyr Trp Met Arg His Ala Leu Thr
1               5                   10                  15

Leu Ala Lys Arg Ala Arg Glu Glu Gly Glu Val Pro Val Gly Ala Val
                20                  25                  30

Leu Val Leu Asn Asn Gln Val Ile Gly Glu Gly Trp Asn Arg Ala Ile
            35                  40                  45

Gly Leu His Asp Pro Thr Ala His Ala Glu Ile Met Ala Ile Arg Gln
    50                  55                  60

Gly Gly Leu Val Leu Gln Asn Tyr Arg Leu Ile Asp Ala Thr Leu Tyr
65                  70                  75                  80

Val Thr Phe Glu Pro Cys Val Met Cys Ala Gly Ala Met Val His Ser
                85                  90                  95

Arg Ile Ser Arg Leu Val Phe Gly Val Arg Asn Ala Lys Thr Gly Ala
            100                 105                 110

Ala Gly Ser Leu Ile Asp Val Leu His Tyr Pro Gly Met Asn His Arg
        115                 120                 125

Val Glu Ile Ala Glu Gly Val Leu Ala Glu Ser Cys Ser Ala Met Leu
    130                 135                 140

Cys Tyr Phe Phe Arg Trp Pro Arg Glu Val Phe Asn Ala Leu Lys Lys
145                 150                 155                 160

Ala Arg Gln Ala Asp Glu Ser
                165
```

<210> SEQ ID NO 23
<211> LENGTH: 166
<212> TYPE: PRT
<213> ORGANISM: Artificial
<220> FEATURE:
<223> OTHER INFORMATION: Engineered novel adenine deaminase 7

<400> SEQUENCE: 23

```
Ser Asp His Glu Leu Asn His Glu His Trp Met Arg His Ala Leu Thr
1               5                   10                  15

Leu Ala Gln Arg Ala Arg Asp Glu Gly Glu Val Pro Val Gly Ala Val
                20                  25                  30

Leu Val Leu Glu Asn Arg Val Ile Gly Glu Gly Trp Asn Arg Ala Ile
            35                  40                  45

Gly Leu His Asp Pro Thr Ala His Ala Glu Ile Met Ala Leu Arg Gln
    50                  55                  60

Gly Gly Leu Val Leu Gln Asn Tyr Arg Leu Ile Asp Thr Thr Leu Tyr
65                  70                  75                  80

Val Thr Phe Glu Pro Cys Val Met Cys Ala Gly Ala Met Val His Ser
                85                  90                  95
```

Arg Ile Gly Gln Leu Val Phe Gly Val Arg Asn Ala Lys Thr Gly Ala
            100                 105                 110

Ala Gly Ser Leu Ile Asp Ile Leu His Tyr Pro Gly Met Asn His Arg
            115                 120                 125

Val Glu Phe Thr Glu Gly Val Leu Lys Asp Thr Cys Ala Thr Leu Leu
    130                 135                 140

Cys Tyr Phe Phe Arg His Pro Arg Gln Val Phe Asn Ala Leu Arg Gln
145                 150                 155                 160

Ala Glu Lys Asp Pro Arg
                165

<210> SEQ ID NO 24
<211> LENGTH: 167
<212> TYPE: PRT
<213> ORGANISM: Artificial
<220> FEATURE:
<223> OTHER INFORMATION: Engineered novel adenine deaminase 8

<400> SEQUENCE: 24

Ser Asp Asn Glu Phe Asn His Glu Tyr Trp Met Arg His Ala Leu Thr
1               5                   10                  15

Leu Ala Gln Arg Ala Arg Asp Glu Gly Glu Val Pro Val Gly Ala Val
            20                  25                  30

Leu Val Leu Asp Asn Gln Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Met Val Leu Gln Asn Tyr Arg Leu Ile Asn Ala Thr Leu Tyr
65                  70                  75                  80

Val Thr Phe Glu Pro Cys Val Met Cys Ala Gly Ala Met Val His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
            115                 120                 125

Val Glu Val Thr Glu Gly Ile Leu Arg Asp Gln Cys Ala Ser Met Leu
    130                 135                 140

Cys Tyr Phe Phe Arg Glu Pro Arg Glu Val Phe Asn Ala Leu Arg Lys
145                 150                 155                 160

Ala Gln Lys Ala Gly Asn Gln
                165

<210> SEQ ID NO 25
<211> LENGTH: 167
<212> TYPE: PRT
<213> ORGANISM: Artificial
<220> FEATURE:
<223> OTHER INFORMATION: Engineered novel adenine deaminase 9

<400> SEQUENCE: 25

Ser Ile Pro Glu Tyr Asn His Glu Tyr Trp Met Arg His Ala Leu Thr
1               5                   10                  15

Leu Ala Gln Arg Ala Arg Asp Glu Gly Glu Val Pro Val Gly Ala Val
            20                  25                  30

Leu Val Leu Asn Asn Gln Val Ile Gly Glu Gly Trp Asn Arg Ala Ile
        35                  40                  45

```
Gly Leu His Asp Pro Thr Ala His Ala Glu Ile Met Ala Leu Arg Gln
 50                  55                  60

Gly Gly Leu Val Leu Gln Asn Tyr Arg Leu Leu Asp Thr Thr Leu Tyr
 65                  70                  75                  80

Val Thr Phe Glu Pro Cys Val Met Cys Ser Gly Ala Met Val His Ser
                 85                  90                  95

Arg Ile Gly Thr Leu Val Phe Gly Val Arg Asn Glu Lys Thr Gly Ala
                100                 105                 110

Ala Gly Ser Leu Met Asp Val Leu Gly Tyr Pro Gly Met Asn His Gln
            115                 120                 125

Val Lys Thr Ile Gly Gly Val Leu Ala Pro Glu Cys Ser Gly Leu Leu
            130                 135                 140

Cys Tyr Phe Phe Arg Met Pro Arg Gln Val Phe Asn Gln Gln Lys Ala
145                 150                 155                 160

Glu Leu Lys Leu Leu Gly Asp
                165
```

```
<210> SEQ ID NO 26
<211> LENGTH: 163
<212> TYPE: PRT
<213> ORGANISM: Artificial
<220> FEATURE:
<223> OTHER INFORMATION: Engineered novel adenine deaminase 10

<400> SEQUENCE: 26
```

```
Ser Glu Val Glu Phe Ser His Glu Tyr Trp Met Arg His Ala Leu Thr
 1                5                  10                  15

Leu Ala Lys Arg Ala Arg Asp Glu Arg Glu Val Arg Trp Val Arg Tyr
                 20                  25                  30

Trp Leu Ile Thr Thr Ala Phe Gly Glu Gly Trp Asn Arg Ala Ile Gly
                 35                  40                  45

Leu His Asp Pro Thr Ala His Ala Glu Ile Met Ala Leu Arg Gln Gly
 50                  55                  60

Gly Leu Val Leu Gln Asn Tyr Arg Leu Leu Asp Ala Thr Leu Tyr Val
 65                  70                  75                  80

Thr Phe Glu Pro Cys Val Met Cys Ala Gly Ala Met Val His Ser Arg
                 85                  90                  95

Ile Gly Arg Val Val Phe Gly Val Arg Asn Ala Lys Thr Gly Ala Ala
                100                 105                 110

Gly Ser Leu Met Asp Val Leu His Tyr Pro Gly Met Asn His Arg Val
            115                 120                 125

Asp Val Thr Glu Gly Val Leu Arg Asp Glu Cys Ala Thr Leu Leu Cys
            130                 135                 140

Tyr Phe Phe Arg Met Pro Arg Gln Val Phe Asn Ala Leu Lys Lys Ser
145                 150                 155                 160

Ala Asn Gln
```

```
<210> SEQ ID NO 27
<211> LENGTH: 168
<212> TYPE: PRT
<213> ORGANISM: Artificial
<220> FEATURE:
<223> OTHER INFORMATION: Engineered novel adenine deaminase 11

<400> SEQUENCE: 27
```

```
Ser Ile Pro Glu Leu Asn His Asp Val Trp Met Arg His Ala Leu Thr
 1                5                  10                  15
```

```
Leu Ala Lys Arg Ala Arg Glu Glu Gly Glu Val Pro Val Gly Ala Val
            20                  25                  30

Leu Val Leu Asn Gly Gln Val Ile Gly Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Leu Gln Asn Tyr Arg Leu Ile Asp Thr Thr Leu Tyr
65                  70                  75                  80

Val Thr Phe Glu Pro Cys Val Met Cys Ala Gly Ala Met Val His Ser
                85                  90                  95

Arg Ile Gly Gln Leu Val Phe Gly Val Arg Asn Ala Lys Thr Gly Ala
            100                 105                 110

Ala Gly Ser Leu Ile Asp Val Leu His Tyr Pro Gly Met Asn His Arg
        115                 120                 125

Val Glu Ile Thr Glu Gly Val Leu Arg Asp Glu Cys Ala Ala Met Leu
    130                 135                 140

Cys Tyr Phe Phe Arg Gln Pro Arg Leu Val Phe Asn Ala Leu Lys Lys
145                 150                 155                 160

Pro Thr Gly Asp Pro Thr Ala Phe
                165

<210> SEQ ID NO 28
<211> LENGTH: 162
<212> TYPE: PRT
<213> ORGANISM: Artificial
<220> FEATURE:
<223> OTHER INFORMATION: Engineered novel adenine deaminase 12

<400> SEQUENCE: 28

Ser Asp Thr Glu Gln His Glu Tyr Trp Met Arg His Ala Leu Thr Leu
1               5                   10                  15

Ala Arg His Ala Arg Asp Glu Gly Glu Val Pro Val Gly Ala Val Leu
            20                  25                  30

Val Leu Glu Gly Asn Val Ile Gly Glu Gly Trp Asn Arg Ala Ile Gly
        35                  40                  45

Leu His Asp Pro Thr Ala His Ala Glu Ile Met Ala Leu Arg Gln Gly
    50                  55                  60

Gly Ala Val Leu Gln Asn Tyr Arg Leu Ile Asn Ala Thr Leu Tyr Val
65                  70                  75                  80

Thr Phe Glu Pro Cys Val Met Cys Ala Gly Ala Met Val His Ser Arg
                85                  90                  95

Ile Ala Arg Leu Val Phe Gly Val Arg Asn Ala Lys Thr Gly Ala Ala
            100                 105                 110

Gly Ser Leu Met Asp Val Leu His Tyr Pro Gly Met Asn His Arg Val
        115                 120                 125

Glu Ile Thr Glu Gly Val Leu Gly Ala Glu Cys Ala Ser Leu Leu Cys
    130                 135                 140

Tyr Phe Phe Arg Gln Pro Arg Glu Val Phe Asn Ala Leu Lys Arg Gly
145                 150                 155                 160

Cys Cys

<210> SEQ ID NO 29
<211> LENGTH: 168
<212> TYPE: PRT
<213> ORGANISM: Artificial
<220> FEATURE:
```

<223> OTHER INFORMATION: Engineered novel adenine deaminase 13

<400> SEQUENCE: 29

```
Ser Asp Leu Glu Leu Asn Asp Glu Tyr Trp Met Arg His Ala Leu Thr
1               5                   10                  15
Leu Ala Lys Arg Ala Arg Glu Glu Gly Glu Val Pro Val Gly Ala Val
            20                  25                  30
Leu Val Leu Asn Asn Gln Val Ile Gly Glu Gly Trp Asn Arg Ala Ile
        35                  40                  45
Gly Leu His Asp Pro Thr Ala His Ala Glu Ile Met Ala Leu Arg Gln
    50                  55                  60
Gly Gly Leu Val Leu Gln Asn Tyr Arg Leu Ile Asp Ala Thr Leu Tyr
65                  70                  75                  80
Val Thr Phe Glu Pro Cys Val Met Cys Ala Gly Ala Met Val His Ser
                85                  90                  95
Arg Ile Ala Arg Leu Val Phe Gly Val Arg Asn Ala Lys Thr Gly Ala
            100                 105                 110
Ala Gly Ser Leu Met Asp Val Leu His Tyr Pro Gly Met Asn His Arg
        115                 120                 125
Val Glu Ile Ser Glu Gly Val Leu Ala Glu Ser Cys Ser Ala Met Leu
    130                 135                 140
Cys Tyr Phe Phe Arg Trp Pro Arg Glu Val Phe Asn Ala Leu Lys Lys
145                 150                 155                 160
Ala Arg Glu Gln Thr Gly Glu Ser
                165
```

<210> SEQ ID NO 30
<211> LENGTH: 166
<212> TYPE: PRT
<213> ORGANISM: Artificial
<220> FEATURE:
<223> OTHER INFORMATION: Engineered novel adenine deaminase 14

<400> SEQUENCE: 30

```
Ser Asn His Glu Leu Asn His Glu His Trp Met Arg His Ala Leu Thr
1               5                   10                  15
Leu Ala Gln Arg Ala Arg Asp Glu Gly Glu Val Pro Val Gly Ala Val
            20                  25                  30
Leu Val Leu Asp Asn Arg Val Ile Gly Glu Gly Trp Asn Arg Ala Ile
        35                  40                  45
Gly Leu His Asp Pro Thr Ala His Ala Glu Ile Met Ala Leu Arg Gln
    50                  55                  60
Gly Gly Leu Val Leu Gln Asn Tyr Arg Leu Ile Asp Thr Thr Leu Tyr
65                  70                  75                  80
Val Thr Phe Glu Pro Cys Val Met Cys Ala Gly Ala Met Val His Ser
                85                  90                  95
Arg Ile Gly Gln Leu Val Phe Gly Val Arg Asn Ala Lys Thr Gly Ala
            100                 105                 110
Ala Gly Ser Leu Ile Asp Val Leu His Tyr Pro Gly Met Asn His Arg
        115                 120                 125
Val Glu Phe Thr Glu Gly Val Leu Gly Glu Glu Cys Ala Ala Leu Leu
    130                 135                 140
Cys Tyr Phe Phe Arg His Pro Arg Gln Val Phe Asn Ala Leu Arg Gln
145                 150                 155                 160
Ala Glu Lys Ser Gln Asp
                165
```

```
<210> SEQ ID NO 31
<211> LENGTH: 172
<212> TYPE: PRT
<213> ORGANISM: Artificial
<220> FEATURE:
<223> OTHER INFORMATION: Engineered novel adenine deaminase 15

<400> SEQUENCE: 31

Ser Gln Thr Glu Leu Thr His Glu Tyr Trp Met Arg His Ala Leu Thr
1               5                   10                  15

Leu Ala Gln Arg Ala Arg Asp Glu Gly Glu Val Pro Val Gly Ala Val
            20                  25                  30

Leu Val Leu Asn Asn Gln Val Ile Gly Glu Gly Trp Asn Arg Ala Ile
        35                  40                  45

Gly Leu His Asp Pro Thr Ala His Ala Glu Ile Met Ala Leu Arg Gln
50                  55                  60

Gly Gly Leu Val Leu Gln Asn Tyr Arg Leu Leu Asp Thr Thr Leu Tyr
65                  70                  75                  80

Val Thr Phe Glu Pro Cys Val Met Cys Ala Gly Ala Met Val His Gly
                85                  90                  95

Arg Ile Gly Thr Leu Val Phe Gly Val Arg Asn Ala Lys Thr Gly Ala
            100                 105                 110

Val Gly Ser Leu Met Asp Ile Thr Gly Tyr Pro Gly Met Asn His Gln
        115                 120                 125

Val Gln Val Ile Glu Gly Ile Leu Ala Thr Glu Cys Ser Ala Met Leu
    130                 135                 140

Cys Tyr Phe Phe Arg Gln Pro Arg Leu Val Phe Asn Ala Leu Lys Glu
145                 150                 155                 160

Ala Thr Lys Arg Ala Thr Gly Ser Asp Pro Ala Ala
                165                 170

<210> SEQ ID NO 32
<211> LENGTH: 32
<212> TYPE: PRT
<213> ORGANISM: Artificial
<220> FEATURE:
<223> OTHER INFORMATION: Linker 1

<400> SEQUENCE: 32

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

<210> SEQ ID NO 33
<211> LENGTH: 367
<212> TYPE: PRT
<213> ORGANISM: Artificial
<220> FEATURE:
<223> OTHER INFORMATION: Novel heterodimeric deoxyadenosine deaminase 1

<400> SEQUENCE: 33

Met Ser Asp Asn Glu Phe Asn His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val Leu Asp Asn Gln Val Ile Gly Glu Gly Trp Asn Arg Pro
        35                  40                  45
```

Ile Gly Arg His Asp Pro Thr Ala His Ala Glu Ile Met Ala Leu Arg
          50                  55                  60

Gln Gly Gly Met Val Leu Gln Asn Tyr Arg Leu Ile Asn Ala Thr Leu
 65                  70                  75                  80

Tyr Val Thr Leu Glu Pro Cys Val Met Cys Ala Gly Ala Met Val His
                     85                  90                  95

Ser Arg Ile Gly His Val Val Phe Gly Ala Arg Asp Ala Lys Thr Gly
                100                 105                 110

Ala Ala Gly Ser Leu Met Asp Val Leu His His Pro Gly Met Asn His
            115                 120                 125

Arg Val Glu Val Thr Glu Gly Val Leu Arg Gln Cys Ala Gly Met
130                 135                 140

Leu Ser Asp Phe Phe Arg Glu Arg Glu Gln Ile Lys Ala Leu Arg
145                 150                 155                 160

Lys Ala Gln Lys Ala Glu Asn Gln Ser Gly Ser Ser Gly Gly Ser
                165                 170                 175

Ser Gly Ser Glu Thr Pro Gly Thr Ser Glu Ser Ala Thr Pro Glu Ser
            180                 185                 190

Ser Gly Gly Ser Ser Gly Gly Ser Ser Asp Asn Glu Phe Asn His Glu
            195                 200                 205

Tyr Trp Met Arg His Ala Leu Thr Leu Ala Gln Arg Ala Arg Asp Glu
            210                 215                 220

Gly Glu Val Pro Val Gly Ala Val Leu Val Leu Asp Asn Gln Val Ile
225                 230                 235                 240

Gly Glu Gly Trp Asn Arg Ala Ile Gly Leu His Asp Pro Thr Ala His
                245                 250                 255

Ala Glu Ile Met Ala Leu Arg Gln Gly Gly Met Val Leu Gln Asn Tyr
            260                 265                 270

Arg Leu Ile Asn Ala Thr Leu Tyr Val Thr Phe Glu Pro Cys Val Met
            275                 280                 285

Cys Ala Gly Ala Met Val His Ser Arg Ile Gly His Val Val Phe Gly
            290                 295                 300

Val Arg Asn Ala Lys Thr Gly Ala Ala Gly Ser Leu Met Asp Val Leu
305                 310                 315                 320

His Tyr Pro Gly Met Asn His Arg Val Glu Val Thr Glu Gly Val Leu
                325                 330                 335

Arg Glu Gln Cys Ala Gly Met Leu Cys Tyr Phe Phe Arg Glu Pro Arg
            340                 345                 350

Glu Val Phe Asn Ala Leu Arg Lys Ala Gln Lys Ala Glu Asn Gln
            355                 360                 365

<210> SEQ ID NO 34
<211> LENGTH: 365
<212> TYPE: PRT
<213> ORGANISM: Artificial
<220> FEATURE:
<223> OTHER INFORMATION: Novel heterodimeric deoxyadenosine deaminase 2

<400> SEQUENCE: 34

Met Ser Asp Ile Glu Gln Asn His Glu Tyr Trp Met Arg His Ala Leu
 1               5                  10                  15

Ala Leu Ala Arg Arg Ala Trp Glu Glu Gly Glu Val Pro Val Gly Ala
                20                  25                  30

Val Leu Val His Asn Asn Gln Val Ile Gly Glu Gly Trp Asn Arg Pro
            35                  40                  45

```
Ile Gly Arg His Asp Pro Thr Ala His Ala Glu Ile Met Ala Leu Arg
        50                  55                  60

Gln Gly Gly Val Val Leu Gln Asn Tyr Arg Leu Ile Asp Thr Thr Leu
 65                  70                  75                  80

Tyr Val Thr Leu Glu Pro Cys Val Met Cys Ala Gly Ala Met Val His
                    85                  90                  95

Gly Arg Ile Gly Gln Leu Val Phe Gly Ala Arg Asp Ala Lys Thr Gly
                100                 105                 110

Ala Ala Gly Ser Leu Ile Asp Val Leu His His Pro Gly Met Asn His
                115                 120                 125

Arg Val Glu Ile Thr Glu Gly Val Leu Ala Asp Glu Cys Ser Ala Met
    130                 135                 140

Leu Ser Asp Phe Phe Arg His Arg Gln Gln Gln Lys Ala Leu Lys
145                 150                 155                 160

Gln Ser Leu Lys Asn Ser Leu Ser Gly Gly Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Asp Ile Glu Gln Asn His Glu Tyr
                195                 200                 205

Trp Met Arg His Ala Leu Ala Leu Ala Arg Arg Ala Arg Glu Glu Gly
    210                 215                 220

Glu Val Pro Val Gly Ala Val Leu Val Leu Asn Asn Gln Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Val Val Leu Gln Asn Tyr Arg
                260                 265                 270

Leu Ile Asp Thr Thr Leu Tyr Val Thr Phe Glu Pro Cys Val Met Cys
                275                 280                 285

Ala Gly Ala Met Val His Gly Arg Ile Gly Gln Leu Val Phe Gly Val
                290                 295                 300

Arg Asn Ala Lys Thr Gly Ala Ala Gly Ser Leu Ile Asp Val Leu His
305                 310                 315                 320

Tyr Pro Gly Met Asn His Arg Val Glu Ile Thr Glu Gly Val Leu Ala
                325                 330                 335

Asp Glu Cys Ser Ala Met Leu Cys Tyr Phe Phe Arg His Pro Arg Gln
                340                 345                 350

Val Phe Asn Ala Leu Lys Gln Ser Leu Lys Asn Ser Leu
                355                 360                 365

<210> SEQ ID NO 35
<211> LENGTH: 369
<212> TYPE: PRT
<213> ORGANISM: Artificial
<220> FEATURE:
<223> OTHER INFORMATION: Novel heterodimeric deoxyadenosine deaminase 3

<400> SEQUENCE: 35

Met Ser Asp Leu Glu Leu Asn Asp Glu Tyr Trp Met Arg His Ala Leu
 1               5                  10                  15

Thr Leu Ala Lys Arg Ala Trp Glu Glu Gly Glu Val Pro Val Gly Ala
                20                  25                  30

Val Leu Val His Asn Asn Gln Val Ile Gly Glu Gly Trp Asn Arg Pro
                35                  40                  45
```

```
Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ala Arg Leu Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Ser Glu Gly Val Leu Ala Glu Ser Cys Ser Ala Met
130                 135                 140

Leu Ser Asp Phe Phe Arg Trp Arg Arg Glu Glu Lys Lys Ala Gln Lys
145                 150                 155                 160

Lys Ala Arg Glu Gln Thr Gly Glu Ser Ser Gly Ser Ser Gly Gly
            165                 170                 175

Ser Ser Gly Ser Glu Thr Pro Gly Thr Ser Glu Ser Ala Thr Pro Glu
        180                 185                 190

Ser Ser Gly Gly Ser Ser Gly Gly Ser Ser Asp Leu Glu Leu Asn Asp
        195                 200                 205

Glu Tyr Trp Met Arg His Ala Leu Thr Leu Ala Lys Arg Ala Arg Glu
    210                 215                 220

Glu Gly Glu Val Pro Val Gly Ala Val Leu Val Leu Asn Asn Gln Val
225                 230                 235                 240

Ile Gly Glu Gly Trp Asn Arg Ala Ile Gly Leu His Asp Pro Thr Ala
                245                 250                 255

His Ala Glu Ile Met Ala Leu Arg Gln Gly Gly Leu Val Leu Gln Asn
            260                 265                 270

Tyr Arg Leu Ile Asp Ala Thr Leu Tyr Val Thr Phe Glu Pro Cys Val
        275                 280                 285

Met Cys Ala Gly Ala Met Val His Ser Arg Ile Ala Arg Leu Val Phe
290                 295                 300

Gly Val Arg Asn Ala Lys Thr Gly Ala Ala Gly Ser Leu Met Asp Val
305                 310                 315                 320

Leu His Tyr Pro Gly Met Asn His Arg Val Glu Ile Ser Glu Gly Val
                325                 330                 335

Leu Ala Glu Ser Cys Ser Ala Met Leu Cys Tyr Phe Phe Arg Trp Pro
            340                 345                 350

Arg Glu Val Phe Asn Ala Gln Lys Lys Ala Arg Glu Gln Thr Gly Glu
        355                 360                 365

Ser

<210> SEQ ID NO 36
<211> LENGTH: 365
<212> TYPE: PRT
<213> ORGANISM: Artificial
<220> FEATURE:
<223> OTHER INFORMATION: Novel heterodimeric deoxyadenosine deaminase 4

<400> SEQUENCE: 36

Met Ser Asp His Glu Phe Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30
```

```
Val Leu Val His Asn Asn Gln Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Ile Leu Ala Glu Ser Cys Ser Ala Met
130                 135                 140

Leu Ser Asp Phe Phe Arg Trp Arg Glu Glu Lys Lys Ala Leu Arg
145                 150                 155                 160

Lys Ala Arg Gln Glu Glu Gly Ser Gly Ser Ser Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Ser Ser Asp His Glu Phe Asn Asp Glu Tyr
            195                 200                 205

Trp Met Arg His Ala Leu Thr Leu Ala Lys Arg Ala Arg Glu Glu Gly
210                 215                 220

Glu Val Pro Val Gly Ala Val Leu Val Leu Asn Asn Gln Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Leu Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Val His Ser Arg Ile Ser Arg Leu Val Phe Gly Val
            290                 295                 300

Arg Asn Ala Lys Thr Gly Ala Ala Gly Ser Leu Ile Asp Val Leu His
305                 310                 315                 320

Tyr Pro Gly Met Asn His Arg Val Glu Ile Thr Glu Gly Ile Leu Ala
            325                 330                 335

Glu Ser Cys Ser Ala Met Leu Cys Tyr Phe Phe Arg Trp Pro Arg Glu
            340                 345                 350

Val Phe Asn Ala Leu Arg Lys Ala Arg Gln Glu Glu Gly
            355                 360                 365

<210> SEQ ID NO 37
<211> LENGTH: 363
<212> TYPE: PRT
<213> ORGANISM: Artificial
<220> FEATURE:
<223> OTHER INFORMATION: Novel heterodimeric deoxyadenosine deaminase 5

<400> SEQUENCE: 37

Met Ser Asp Ile Glu Leu Asn His Glu Tyr Trp Met Arg His Ala Leu
1               5                   10                  15

Val Leu Ala Gln Arg Ala Trp Asp Glu Gly Glu Val Pro Val Gly Ala
            20                  25                  30
```

Val Leu Val His Asn Asn Gln Val Ile Gly Glu Gly Trp Asn Arg Pro
             35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Ile Asp Thr Thr Leu
 65                  70                  75                  80

Tyr Val Thr Leu Glu Pro Cys Val Met Cys Ala Gly Ala Met Val His
                 85                  90                  95

Gly Arg Ile Gly Asn Leu Val Phe Gly Ala Arg Asp Ala Lys Thr Gly
            100                 105                 110

Ala Ala Gly Ser Leu Ile Asp Val Leu His His Pro Gly Met Asn His
            115                 120                 125

Arg Val Glu Ile Thr Glu Gly Val Leu Ala Glu Cys Ser Ala Met
130                 135                 140

Leu Ser Asp Phe Phe Arg His Arg Gln Gln Gln Lys Ala Leu Arg
145                 150                 155                 160

Gln Ala Glu Lys Gly Ser Ser Gly Ser Ser Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Asp Ile Glu Leu Asn His Glu Tyr Trp
            195                 200                 205

Met Arg His Ala Leu Val Leu Ala Gln Arg Ala Arg Asp Glu Gly Glu
210                 215                 220

Val Pro Val Gly Ala Val Leu Val Leu Asn Asn Gln Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Leu Gln Asn Tyr Arg Leu
            260                 265                 270

Ile Asp Thr Thr Leu Tyr Val Thr Phe Glu Pro Cys Val Met Cys Ala
            275                 280                 285

Gly Ala Met Val His Gly Arg Ile Gly Asn Leu Val Phe Gly Val Arg
            290                 295                 300

Asn Ala Lys Thr Gly Ala Ala Gly Ser Leu Ile Asp Val Leu His Tyr
305                 310                 315                 320

Pro Gly Met Asn His Arg Val Glu Ile Thr Glu Gly Val Leu Ala Glu
                325                 330                 335

Glu Cys Ser Ala Met Leu Cys Tyr Phe Arg His Pro Arg Gln Val
            340                 345                 350

Phe Asn Ala Leu Arg Gln Ala Glu Lys Gly Ser
            355                 360

<210> SEQ ID NO 38
<211> LENGTH: 367
<212> TYPE: PRT
<213> ORGANISM: Artificial
<220> FEATURE:
<223> OTHER INFORMATION: Novel heterodimeric deoxyadenosine deaminase 6

<400> SEQUENCE: 38

Met Ser Asp His Glu Arg Asn Asp Glu Tyr Trp Met Arg His Ala Leu
 1                   5                  10                  15

Thr Leu Ala Lys Arg Ala Trp Glu Glu Gly Glu Val Pro Val Gly Ala
             20                  25                  30

```
Val Leu Val His Asn Asn Gln Val Ile Gly Glu Gly Trp Asn Arg Pro
         35                  40                  45

Ile Gly Arg His Asp Pro Thr Ala His Ala Glu Ile Met Ala Ile Arg
 50                  55                  60

Gln Gly Gly Leu Val Leu Gln Asn Tyr Arg Leu Ile Asp Ala Thr Leu
 65                  70                  75                  80

Tyr Val Thr Leu Glu Pro Cys Val Met Cys Ala Gly Ala Met Val His
                 85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Ala Glu Gly Val Leu Ala Glu Ser Cys Ser Ala Met
130                 135                 140

Leu Ser Asp Phe Phe Arg Trp Arg Glu Glu Lys Lys Ala Leu Lys
145                 150                 155                 160

Lys Ala Arg Gln Ala Asp Glu Ser Ser Gly Ser Ser Gly Gly Ser
                165                 170                 175

Ser Gly Ser Glu Thr Pro Gly Thr Ser Glu Ser Ala Thr Pro Glu Ser
            180                 185                 190

Ser Gly Gly Ser Ser Gly Gly Ser Ser Asp His Glu Arg Asn Asp Glu
        195                 200                 205

Tyr Trp Met Arg His Ala Leu Thr Leu Ala Lys Arg Ala Arg Glu Glu
210                 215                 220

Gly Glu Val Pro Val Gly Ala Val Leu Val Leu Asn Asn Gln Val Ile
225                 230                 235                 240

Gly Glu Gly Trp Asn Arg Ala Ile Gly Leu His Asp Pro Thr Ala His
                245                 250                 255

Ala Glu Ile Met Ala Ile Arg Gln Gly Gly Leu Val Leu Gln Asn Tyr
            260                 265                 270

Arg Leu Ile Asp Ala Thr Leu Tyr Val Thr Phe Glu Pro Cys Val Met
        275                 280                 285

Cys Ala Gly Ala Met Val His Ser Arg Ile Ser Arg Leu Val Phe Gly
290                 295                 300

Val Arg Asn Ala Lys Thr Gly Ala Ala Gly Ser Leu Ile Asp Val Leu
305                 310                 315                 320

His Tyr Pro Gly Met Asn His Arg Val Glu Ile Ala Glu Gly Val Leu
                325                 330                 335

Ala Glu Ser Cys Ser Ala Met Leu Cys Tyr Phe Phe Arg Trp Pro Arg
            340                 345                 350

Glu Val Phe Asn Ala Leu Lys Lys Ala Arg Gln Ala Asp Glu Ser
        355                 360                 365

<210> SEQ ID NO 39
<211> LENGTH: 365
<212> TYPE: PRT
<213> ORGANISM: Artificial
<220> FEATURE:
<223> OTHER INFORMATION: Novel heterodimeric deoxyadenosine deaminase 7

<400> SEQUENCE: 39

Met Ser Asp His Glu Leu Asn His Glu His Trp Met Arg His Ala Leu
1               5                   10                  15

Thr Leu Ala Gln Arg Ala Trp Asp Glu Gly Glu Val Pro Val Gly Ala
            20                  25                  30
```

Val Leu Val His Glu Asn Arg Val Ile Gly Glu Gly Trp Asn Arg Pro
         35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Ile Asp Thr Thr Leu
 65                  70                  75                  80

Tyr Val Thr Leu Glu Pro Cys Val Met Cys Ala Gly Ala Met Val His
                 85                  90                  95

Ser Arg Ile Gly Gln Leu Val Phe Gly Ala Arg Asp Ala Lys Thr Gly
                100                 105                 110

Ala Ala Gly Ser Leu Ile Asp Ile Leu His His Pro Gly Met Asn His
                115                 120                 125

Arg Val Glu Phe Thr Glu Gly Val Leu Lys Asp Thr Cys Ala Thr Leu
            130                 135                 140

Leu Ser Glu Phe Phe Arg His Arg Gln Val Lys Lys Ala Leu Arg
145                 150                 155                 160

Gln Ala Glu Lys Asp Pro Arg Ser Gly Ser Ser Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Asp His Glu Leu Asn His Glu His
                195                 200                 205

Trp Met Arg His Ala Leu Thr Leu Ala Gln Arg Ala Arg Asp Glu Gly
            210                 215                 220

Glu Val Pro Val Gly Ala Val Leu Val Leu Glu Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Leu Gln Asn Tyr Arg
                260                 265                 270

Leu Ile Asp Thr Thr Leu Tyr Val Thr Phe Glu Pro Cys Val Met Cys
            275                 280                 285

Ala Gly Ala Met Val His Ser Arg Ile Gly Gln Leu Val Phe Gly Val
            290                 295                 300

Arg Asn Ala Lys Thr Gly Ala Ala Gly Ser Leu Ile Asp Ile Leu His
305                 310                 315                 320

Tyr Pro Gly Met Asn His Arg Val Glu Phe Thr Glu Gly Val Leu Lys
                325                 330                 335

Asp Thr Cys Ala Thr Leu Leu Cys Tyr Phe Phe Arg His Pro Arg Gln
            340                 345                 350

Val Phe Asn Ala Leu Arg Gln Ala Glu Lys Asp Pro Arg
            355                 360                 365

<210> SEQ ID NO 40
<211> LENGTH: 367
<212> TYPE: PRT
<213> ORGANISM: Artificial
<220> FEATURE:
<223> OTHER INFORMATION: Novel heterodimeric deoxyadenosine deaminase 8

<400> SEQUENCE: 40

Met Ser Asp Asn Glu Phe Asn His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val Leu Asp Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Met Val Leu Gln Asn Tyr Arg Leu Ile Asn Ala Thr Leu
65                  70                  75                  80

Tyr Val Thr Leu Glu Pro Cys Val Met Cys Ala Gly Ala Met Val His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Val Thr Glu Gly Ile Leu Arg Asp Gln Cys Ala Ser Met
    130                 135                 140

Leu Ser Asp Phe Phe Arg Glu Arg Glu Gln Ile Lys Ala Leu Arg
145                 150                 155                 160

Lys Ala Gln Lys Ala Gly Asn Gln Ser Gly Ser Ser Gly Gly Ser
                165                 170                 175

Ser Gly Ser Glu Thr Pro Gly Thr Ser Glu Ser Ala Thr Pro Glu Ser
            180                 185                 190

Ser Gly Gly Ser Ser Gly Gly Ser Ser Asp Asn Glu Phe Asn His Glu
        195                 200                 205

Tyr Trp Met Arg His Ala Leu Thr Leu Ala Gln Arg Ala Arg Asp Glu
    210                 215                 220

Gly Glu Val Pro Val Gly Ala Val Leu Val Leu Asp Asn Gln Val Ile
225                 230                 235                 240

Gly Glu Gly Trp Asn Arg Ala Ile Gly Leu His Asp Pro Thr Ala His
                245                 250                 255

Ala Glu Ile Met Ala Leu Arg Gln Gly Gly Met Val Leu Gln Asn Tyr
            260                 265                 270

Arg Leu Ile Asn Ala Thr Leu Tyr Val Thr Phe Glu Pro Cys Val Met
        275                 280                 285

Cys Ala Gly Ala Met Val His Ser Arg Ile Gly Arg Val Val Phe Gly
    290                 295                 300

Val Arg Asn Ala Lys Thr Gly Ala Ala Gly Ser Leu Met Asp Val Leu
305                 310                 315                 320

His Tyr Pro Gly Met Asn His Arg Val Glu Val Thr Glu Gly Ile Leu
                325                 330                 335

Arg Asp Gln Cys Ala Ser Met Leu Cys Tyr Phe Phe Arg Glu Pro Arg
            340                 345                 350

Glu Val Phe Asn Ala Leu Arg Lys Ala Gln Lys Ala Gly Asn Gln
        355                 360                 365

<210> SEQ ID NO 41
<211> LENGTH: 367
<212> TYPE: PRT
<213> ORGANISM: Artificial
<220> FEATURE:
<223> OTHER INFORMATION: Novel heterodimeric deoxyadenosine deaminase 9

<400> SEQUENCE: 41

Met Ser Ile Pro Glu Tyr Asn His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

```
Val Leu Val His Asn Asn Gln Val Ile Gly Glu Gly Trp Asn Arg Pro
         35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Leu Asp Thr Thr Leu
 65                  70                  75                  80

Tyr Val Thr Leu Glu Pro Cys Val Met Cys Ser Gly Ala Met Val His
                 85                  90                  95

Ser Arg Ile Gly Thr Leu Val Phe Gly Ala Arg Asp Glu Lys Thr Gly
                100                 105                 110

Ala Ala Gly Ser Leu Met Asp Val Leu Gly His Pro Gly Met Asn His
                115                 120                 125

Gln Val Lys Thr Ile Gly Gly Val Leu Ala Pro Glu Cys Ser Gly Leu
    130                 135                 140

Leu Ser Asp Phe Phe Arg Met Arg Arg Gln Gln Lys Lys Gln Gln Lys
145                 150                 155                 160

Ala Glu Leu Lys Leu Leu Gly Asp Ser Gly Ser Ser Gly Gly Ser
                165                 170                 175

Ser Gly Ser Glu Thr Pro Gly Thr Ser Glu Ser Ala Thr Pro Glu Ser
                180                 185                 190

Ser Gly Gly Ser Ser Gly Gly Ser Ser Ile Pro Glu Tyr Asn His Glu
                195                 200                 205

Tyr Trp Met Arg His Ala Leu Thr Leu Ala Gln Arg Ala Arg Asp Glu
            210                 215                 220

Gly Glu Val Pro Val Gly Ala Val Leu Val Leu Asn Asn Gln Val Ile
225                 230                 235                 240

Gly Glu Gly Trp Asn Arg Ala Ile Gly Leu His Asp Pro Thr Ala His
                245                 250                 255

Ala Glu Ile Met Ala Leu Arg Gln Gly Gly Leu Val Leu Gln Asn Tyr
                260                 265                 270

Arg Leu Leu Asp Thr Thr Leu Tyr Val Thr Phe Glu Pro Cys Val Met
            275                 280                 285

Cys Ser Gly Ala Met Val His Ser Arg Ile Gly Thr Leu Val Phe Gly
290                 295                 300

Val Arg Asn Glu Lys Thr Gly Ala Ala Gly Ser Leu Met Asp Val Leu
305                 310                 315                 320

Gly Tyr Pro Gly Met Asn His Gln Val Lys Thr Ile Gly Gly Val Leu
                325                 330                 335

Ala Pro Glu Cys Ser Gly Leu Leu Cys Tyr Phe Phe Arg Met Pro Arg
                340                 345                 350

Gln Val Phe Asn Gln Gln Lys Ala Glu Leu Lys Leu Leu Gly Asp
            355                 360                 365

<210> SEQ ID NO 42
<211> LENGTH: 359
<212> TYPE: PRT
<213> ORGANISM: Artificial
<220> FEATURE:
<223> OTHER INFORMATION: Novel heterodimeric deoxyadenosine deaminase 10

<400> SEQUENCE: 42

Met Ser Glu Val Glu Phe Ser His Glu Tyr Trp Met Arg His Ala Leu
 1               5                  10                  15

Thr Leu Ala Lys Arg Ala Trp Asp Glu Arg Glu Val Arg Trp Val Arg
                20                  25                  30
```

Tyr Trp Tyr Ile Thr Thr Ala Phe Gly Glu Gly Trp Asn Arg Pro Ile
                35                  40                  45

Gly His His Asp Pro Thr Ala His Ala Glu Ile Met Ala Leu Arg Gln
     50                  55                  60

Gly Gly Leu Val Leu Gln Asn Tyr Arg Leu Leu Asp Ala Thr Leu Tyr
65                  70                  75                  80

Val Thr Leu Glu Pro Cys Val Met Cys Ala Gly Ala Met Val His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Asp Val Thr Glu Gly Val Leu Arg Asp Glu Cys Ala Thr Leu Leu
    130                 135                 140

Ser Asp Phe Phe Arg Met Arg Arg Gln Glu Ile Lys Ala Leu Lys Lys
145                 150                 155                 160

Ser Ala Asn Gln Ser Gly Gly Ser Ser Gly Ser Ser Gly Ser Ser Glu
                165                 170                 175

Thr Pro Gly Thr Ser Glu Ser Ala Thr Pro Glu Ser Ser Gly Gly Ser
            180                 185                 190

Ser Gly Gly Ser Ser Glu Val Glu Phe Ser His Glu Tyr Trp Met Arg
        195                 200                 205

His Ala Leu Thr Leu Ala Lys Arg Ala Arg Asp Glu Arg Glu Val Arg
    210                 215                 220

Trp Val Arg Tyr Trp Leu Ile Thr Thr Ala Phe Gly Glu Gly Trp Asn
225                 230                 235                 240

Arg Ala Ile Gly Leu His Asp Pro Thr Ala His Ala Glu Ile Met Ala
                245                 250                 255

Leu Arg Gln Gly Gly Leu Val Leu Gln Asn Tyr Arg Leu Leu Asp Ala
            260                 265                 270

Thr Leu Tyr Val Thr Phe Glu Pro Cys Val Met Cys Ala Gly Ala Met
        275                 280                 285

Val His Ser Arg Ile Gly Arg Val Val Phe Gly Val Arg Asn Ala Lys
    290                 295                 300

Thr Gly Ala Ala Gly Ser Leu Met Asp Val Leu His Tyr Pro Gly Met
305                 310                 315                 320

Asn His Arg Val Asp Val Thr Glu Gly Val Leu Arg Asp Glu Cys Ala
                325                 330                 335

Thr Leu Leu Cys Tyr Phe Phe Arg Met Pro Arg Gln Val Phe Asn Ala
            340                 345                 350

Leu Lys Lys Ser Ala Asn Gln
        355

<210> SEQ ID NO 43
<211> LENGTH: 369
<212> TYPE: PRT
<213> ORGANISM: Artificial
<220> FEATURE:
<223> OTHER INFORMATION: Novel heterodimeric deoxyadenosine deaminase 11

<400> SEQUENCE: 43

Met Ser Ile Pro Glu Leu Asn His Asp Val Trp Met Arg His Ala Leu
1               5                   10                  15

Thr Leu Ala Lys Arg Ala Arg Glu Glu Gly Glu Val Pro Val Gly Ala
            20                  25                  30

Val Leu Val His Asn Gly Gln Val Ile Gly Glu Gly Trp Asn Arg Pro
                35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Ile Asp Thr Thr Leu
 65                  70                  75                  80

Tyr Val Thr Leu Glu Pro Cys Val Met Cys Ala Gly Ala Met Val His
                 85                  90                  95

Ser Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Arg Asp Glu Cys Ala Ala Met
130                 135                 140

Leu Ser Asp Phe Phe Arg Gln Arg Leu Glu Lys Lys Ala Leu Lys
145                 150                 155                 160

Lys Pro Thr Gly Asp Pro Thr Ala Phe Ser Gly Ser Ser Gly Gly
                165                 170                 175

Ser Ser Gly Ser Glu Thr Pro Gly Thr Ser Glu Ser Ala Thr Pro Glu
            180                 185                 190

Ser Ser Gly Gly Ser Ser Gly Gly Ser Ser Ile Pro Glu Leu Asn His
        195                 200                 205

Asp Val Trp Met Arg His Ala Leu Thr Leu Ala Lys Arg Ala Arg Glu
210                 215                 220

Glu Gly Glu Val Pro Val Gly Ala Val Leu Val Leu Asn Gly Gln Val
225                 230                 235                 240

Ile Gly Glu Gly Trp Asn Arg Ala Ile Gly Leu His Asp Pro Thr Ala
                245                 250                 255

His Ala Glu Ile Met Ala Leu Arg Gln Gly Gly Leu Val Leu Gln Asn
            260                 265                 270

Tyr Arg Leu Ile Asp Thr Thr Leu Tyr Val Thr Phe Glu Pro Cys Val
        275                 280                 285

Met Cys Ala Gly Ala Met Val His Ser Arg Ile Gly Gln Leu Val Phe
290                 295                 300

Gly Val Arg Asn Ala Lys Thr Gly Ala Ala Gly Ser Leu Ile Asp Val
305                 310                 315                 320

Leu His Tyr Pro Gly Met Asn His Arg Val Glu Ile Thr Glu Gly Val
                325                 330                 335

Leu Arg Asp Glu Cys Ala Ala Met Leu Cys Tyr Phe Phe Arg Gln Pro
            340                 345                 350

Arg Leu Val Phe Asn Ala Leu Lys Lys Pro Thr Gly Asp Pro Thr Ala
        355                 360                 365

Phe

<210> SEQ ID NO 44
<211> LENGTH: 357
<212> TYPE: PRT
<213> ORGANISM: Artificial
<220> FEATURE:
<223> OTHER INFORMATION: Novel heterodimeric deoxyadenosine deaminase 12

<400> SEQUENCE: 44

Met Ser Asp Thr Glu Gln His Glu Tyr Trp Met Arg His Ala Leu Thr
1               5                   10                  15

```
Leu Ala Arg His Ala Trp Asp Glu Gly Glu Val Pro Val Gly Ala Val
            20                  25                  30

Leu Val His Glu Gly Asn Val Ile Gly Glu Gly Trp Asn Arg Pro Ile
        35                  40                  45

Gly Arg His Asp Pro Thr Ala His Ala Glu Ile Met Ala Leu Arg Gln
 50                  55                  60

Gly Gly Ala Val Leu Gln Asn Tyr Arg Leu Ile Asn Ala Thr Leu Tyr
 65                  70                  75                  80

Val Thr Leu Glu Pro Cys Val Met Cys Ala Gly Ala Met Val His Ser
                85                  90                  95

Arg Ile Ala Arg Leu Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Val Leu Gly Ala Glu Cys Ala Ser Leu Leu
    130                 135                 140

Ser Asp Phe Phe Arg Gln Arg Glu Gln Lys Lys Ala Leu Lys Arg
145                 150                 155                 160

Gly Cys Cys Ser Gly Gly Ser Ser Gly Ser Ser Gly Ser Glu Thr
            165                 170                 175

Pro Gly Thr Ser Glu Ser Ala Thr Pro Glu Ser Ser Gly Gly Ser Ser
        180                 185                 190

Gly Gly Ser Ser Asp Thr Glu Gln His Glu Tyr Trp Met Arg His Ala
    195                 200                 205

Leu Thr Leu Ala Arg His Ala Arg Asp Glu Gly Glu Val Pro Val Gly
    210                 215                 220

Ala Val Leu Val Leu Glu Gly Asn Val Ile Gly Glu Gly Trp Asn Arg
225                 230                 235                 240

Ala Ile Gly Leu His Asp Pro Thr Ala His Ala Glu Ile Met Ala Leu
            245                 250                 255

Arg Gln Gly Gly Ala Val Leu Gln Asn Tyr Arg Leu Ile Asn Ala Thr
        260                 265                 270

Leu Tyr Val Thr Phe Glu Pro Cys Val Met Cys Ala Gly Ala Met Val
    275                 280                 285

His Ser Arg Ile Ala Arg Leu Val Phe Gly Val Arg Asn Ala Lys Thr
290                 295                 300

Gly Ala Ala Gly Ser Leu Met Asp Val Leu His Tyr Pro Gly Met Asn
305                 310                 315                 320

His Arg Val Glu Ile Thr Glu Gly Val Leu Gly Ala Glu Cys Ala Ser
            325                 330                 335

Leu Leu Cys Tyr Phe Phe Arg Gln Pro Arg Glu Val Phe Asn Ala Leu
        340                 345                 350

Lys Arg Gly Cys Cys
        355

<210> SEQ ID NO 45
<211> LENGTH: 369
<212> TYPE: PRT
<213> ORGANISM: Artificial
<220> FEATURE:
<223> OTHER INFORMATION: Novel heterodimeric deoxyadenosine deaminase 13

<400> SEQUENCE: 45

Met Ser Asp Leu Glu Leu Asn Asp Glu Tyr Trp Met Arg His Ala Leu
1               5                   10                  15
```

Thr Leu Ala Lys Arg Ala Arg Glu Glu Gly Val Pro Val Gly Ala
            20                  25                  30

Val Leu Val His Asn Asn Gln Val Ile Gly Glu Gly Trp Asn Arg Pro
                35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Ile Asp Ala Thr Leu
 65                  70                  75                  80

Tyr Val Thr Leu Glu Pro Cys Val Met Cys Ala Gly Ala Met Val His
                85                  90                  95

Ser Arg Ile Ala Arg Leu Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Ser Glu Gly Val Leu Ala Glu Ser Cys Ser Ala Met
            130                 135                 140

Leu Ser Asp Phe Phe Arg Trp Arg Arg Glu Glu Lys Lys Ala Leu Lys
145                 150                 155                 160

Lys Ala Arg Glu Gln Thr Gly Glu Ser Ser Gly Ser Ser Gly Gly
            165                 170                 175

Ser Ser Gly Ser Glu Thr Pro Gly Thr Ser Glu Ser Ala Thr Pro Glu
            180                 185                 190

Ser Ser Gly Gly Ser Ser Gly Gly Ser Ser Asp Leu Glu Leu Asn Asp
            195                 200                 205

Glu Tyr Trp Met Arg His Ala Leu Thr Leu Ala Lys Arg Ala Arg Glu
            210                 215                 220

Glu Gly Glu Val Pro Val Gly Ala Val Leu Val Leu Asn Asn Gln Val
225                 230                 235                 240

Ile Gly Glu Gly Trp Asn Arg Ala Ile Gly Leu His Asp Pro Thr Ala
            245                 250                 255

His Ala Glu Ile Met Ala Leu Arg Gln Gly Gly Leu Val Leu Gln Asn
            260                 265                 270

Tyr Arg Leu Ile Asp Ala Thr Leu Tyr Val Thr Phe Glu Pro Cys Val
            275                 280                 285

Met Cys Ala Gly Ala Met Val His Ser Arg Ile Ala Arg Leu Val Phe
            290                 295                 300

Gly Val Arg Asn Ala Lys Thr Gly Ala Ala Gly Ser Leu Met Asp Val
305                 310                 315                 320

Leu His Tyr Pro Gly Met Asn His Arg Val Glu Ile Ser Glu Gly Val
            325                 330                 335

Leu Ala Glu Ser Cys Ser Ala Met Leu Cys Tyr Phe Phe Arg Trp Pro
            340                 345                 350

Arg Glu Val Phe Asn Ala Leu Lys Lys Ala Arg Glu Gln Thr Gly Glu
            355                 360                 365

Ser

<210> SEQ ID NO 46
<211> LENGTH: 365
<212> TYPE: PRT
<213> ORGANISM: Artificial
<220> FEATURE:
<223> OTHER INFORMATION: Novel heterodimeric deoxyadenosine deaminase 14

<400> SEQUENCE: 46

```
Met Ser Asn His Glu Leu Asn His Glu His Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Asp Asn Arg Val Ile Gly Glu Gly Trp Asn Arg Pro
        35                  40                  45

Ile Gly Arg His Asp Pro Thr Ala His Ala Glu Ile Met Ala Leu Arg
50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Ser Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Phe Thr Glu Gly Val Leu Gly Glu Cys Ala Ala Leu
130                 135                 140

Leu Ser Asp Phe Phe Arg His Arg Arg Gln Val Lys Lys Ala Leu Arg
145                 150                 155                 160

Gln Ala Glu Lys Ser Gln Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Asn His Glu Leu Asn His Glu His
        195                 200                 205

Trp Met Arg His Ala Leu Thr Leu Ala Gln Arg Ala Arg Asp Glu Gly
        210                 215                 220

Glu Val Pro Val Gly Ala Val Leu Val Leu Asp Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Leu Gln Asn Tyr Arg
            260                 265                 270

Leu Ile Asp Thr Thr Leu Tyr Val Thr Phe Glu Pro Cys Val Met Cys
        275                 280                 285

Ala Gly Ala Met Val His Ser Arg Ile Gly Gln Leu Val Phe Gly Val
290                 295                 300

Arg Asn Ala Lys Thr Gly Ala Ala Gly Ser Leu Ile Asp Val Leu His
305                 310                 315                 320

Tyr Pro Gly Met Asn His Arg Val Glu Phe Thr Glu Gly Val Leu Gly
                325                 330                 335

Glu Glu Cys Ala Ala Leu Leu Cys Tyr Phe Phe Arg His Pro Arg Gln
            340                 345                 350

Val Phe Asn Ala Leu Arg Gln Ala Glu Lys Ser Gln Asp
        355                 360                 365
```

<210> SEQ ID NO 47
<211> LENGTH: 377
<212> TYPE: PRT
<213> ORGANISM: Artificial
<220> FEATURE:
<223> OTHER INFORMATION: Novel heterodimeric deoxyadenosine deaminase 15

-continued

<400> SEQUENCE: 47

```
Met Ser Gln Thr Glu Leu Thr His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
 50                  55                  60

Gln Gly Gly Leu Val Leu Gln Asn Tyr Arg Leu Leu Asp Thr Thr Leu
65                  70                  75                  80

Tyr Val Thr Leu Glu Pro Cys Val Met Cys Ala Gly Ala Met Val His
                85                  90                  95

Gly Arg Ile Gly Thr Leu Val Phe Gly Ala Arg Asp Ala Lys Thr Gly
            100                 105                 110

Ala Val Gly Ser Leu Met Asp Ile Thr Gly Pro Gly Met Asn His
        115                 120                 125

Gln Val Gln Val Ile Glu Gly Ile Leu Ala Thr Glu Cys Ser Ala Met
130                 135                 140

Leu Ser Ala Phe Phe Arg Gln Arg Leu Glu Lys Lys Ala Leu Lys
145                 150                 155                 160

Glu Ala Thr Lys Arg Ala Thr Gly Ser Asp Pro Ala Ala Ser Gly Gly
                165                 170                 175

Ser Ser Gly Gly Ser Ser Gly Ser Glu Thr Pro Gly Thr Ser Glu Ser
            180                 185                 190

Ala Thr Pro Glu Ser Ser Gly Gly Ser Ser Gly Gly Ser Ser Gln Thr
        195                 200                 205

Glu Leu Thr His Glu Tyr Trp Met Arg His Ala Leu Thr Leu Ala Gln
210                 215                 220

Arg Ala Arg Asp Glu Gly Glu Val Pro Val Gly Ala Val Leu Val Leu
225                 230                 235                 240

Asn Asn Gln Val Ile Gly Glu Gly Trp Asn Arg Ala Ile Gly Leu His
                245                 250                 255

Asp Pro Thr Ala His Ala Glu Ile Met Ala Leu Arg Gln Gly Gly Leu
            260                 265                 270

Val Leu Gln Asn Tyr Arg Leu Leu Asp Thr Thr Leu Tyr Val Thr Phe
        275                 280                 285

Glu Pro Cys Val Met Cys Ala Gly Ala Met Val His Gly Arg Ile Gly
290                 295                 300

Thr Leu Val Phe Gly Val Arg Asn Ala Lys Thr Gly Ala Val Gly Ser
305                 310                 315                 320

Leu Met Asp Ile Thr Gly Tyr Pro Gly Met Asn His Gln Val Gln Val
                325                 330                 335

Ile Glu Gly Ile Leu Ala Thr Glu Cys Ser Ala Met Leu Cys Tyr Phe
            340                 345                 350

Phe Arg Gln Pro Arg Leu Val Phe Asn Ala Leu Lys Glu Ala Thr Lys
        355                 360                 365

Arg Ala Thr Gly Ser Asp Pro Ala Ala
370                 375
```

<210> SEQ ID NO 48
<211> LENGTH: 896
<212> TYPE: DNA

-continued

<213> ORGANISM: Zea mays

<400> SEQUENCE: 48

| gtgcagcgtg | acccggtcgt | gcccctctct | agagataatg | agcattgcat | gtctaagtta | 60 |
| taaaaaatta | ccacatattt | ttttgtcac | acttgtttga | agtgcagttt | atctatcttt | 120 |
| atacatatat | ttaaacttta | ctctacgaat | aatataatct | atagtactac | aataatatca | 180 |
| gtgttttaga | gaatcatata | aatgaacagt | tagacatggt | ctaaaggaca | attgagtatt | 240 |
| ttgacaacag | gactctacag | ttttatcttt | ttagtgtgca | tgtgttctcc | tttttttttg | 300 |
| caaatagctt | cacctatata | atacttcatc | cattttatta | gtacatccat | ttagggttta | 360 |
| gggttaatgg | ttttatatga | ctaatttttt | tagtacatct | attttattct | attttagcct | 420 |
| ctaaattaag | aaaactaaaa | ctctatttta | gttttttttat | ttaataattt | agatataaaa | 480 |
| tagaataaaa | taaagtgact | aaaaattaaa | caaatacct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggaccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattccttc | ccaccgctcc | 840 |
| ttcgctttcc | cttcctcgcc | cgccgtaata | aatagacacc | cctccacac | cctctt | 896 |

<210> SEQ ID NO 49
<211> LENGTH: 82
<212> TYPE: DNA
<213> ORGANISM: Zea mays

<400> SEQUENCE: 49

| tccccaacct | cgtgttgttc | ggagcgcaca | cacacacaac | cagatctccc | ccaaatccac | 60 |
| ccgtcggcac | ctccgcttca | ag | | | | 82 |

<210> SEQ ID NO 50
<211> LENGTH: 1013
<212> TYPE: DNA
<213> ORGANISM: Zea mays

<400> SEQUENCE: 50

| gtacgccgct | cgtcctcccc | cccccccctc | tctaccttct | ctagatcggc | gttccggtcc | 60 |
| atgcatggtt | agggcccggt | agttctactt | ctgttcatgt | ttgtgttaga | tccgtgtttg | 120 |
| tgttagatcc | gtgctgctag | cgttcgtaca | cggatgcgac | ctgtacgtca | gacacgttct | 180 |
| gattgctaac | ttgccagtgt | ttctctttgg | ggaatcctgg | gatggctcta | gccgttccgc | 240 |
| agacgggatc | gatttcatga | tttttttttgt | ttcgttgcat | agggtttggt | ttgccctttt | 300 |
| cctttatttc | aatatatgcc | gtgcacttgt | ttgtcgggtc | atcttttcat | gctttttttt | 360 |
| gtcttggttg | tgatgatgtg | gtctggttgg | gcggtcgttc | tagatcggag | tagaattctg | 420 |
| tttcaaacta | cctggtggat | ttattaattt | tggatctgta | tgtgtgtgcc | atacatattc | 480 |
| atagttacga | attgaagatg | atggatggaa | atatcgatct | aggataggta | tacatgttga | 540 |
| tgcgggtttt | actgatgcat | atacagagat | gcttttttgtt | cgcttggttg | tgatgatgtg | 600 |
| gtgtggttgg | gcggtcgttc | attcgttcta | gatcggagta | gaatactgtt | tcaaactacc | 660 |
| tggtgtattt | attaattttg | gaactgtatg | tgtgtgtcat | acatcttcat | agttacgagt | 720 |
| ttaagatgga | tggaaatatc | gatctaggat | aggtatacat | gttgatgtgg | gttttactga | 780 |

| | |
|---|---|
| tgcatataca tgatggcata tgcagcatct attcatatgc tctaaccttg agtacctatc | 840 |
| tattataata aacaagtatg ttttataatt attttgatct tgatatactt ggatgatggc | 900 |
| atatgcagca gctatatgtg gattttttta gccctgcctt catacgctat ttatttgctt | 960 |
| ggtactgttt cttttgtcga tgctcaccct gttgtttggt gttacttctg cag | 1013 |

<210> SEQ ID NO 51
<211> LENGTH: 504
<212> TYPE: DNA
<213> ORGANISM: Artificial
<220> FEATURE:
<223> OTHER INFORMATION: Sequence encoding novel adenine deaminase 1

<400> SEQUENCE: 51

| | |
|---|---|
| atgagcgaca acgagttcaa ccacgagtac tggatgcgcc acgccctcac actcgcccag | 60 |
| agagcgtggg acgagggcga ggttcctgtc ggtgctgtcc tcgtcctgga caaccaggtg | 120 |
| atcggagagg gctggaacag gccgatcggc agacacgacc ccacagcgca cgcagagatc | 180 |
| atggccctcc gccagggcgg catggtcctc cagaactacc gcctcatcaa cgccaccctc | 240 |
| tacgtcaccc tcgagccgtg cgtgatgtgc gcaggcgcga tggtgcacag ccgcatcggc | 300 |
| cacgtcgtgt tcggcgccag agacgccaag acaggagccg caggctcgtt gatggacgtg | 360 |
| ctccaccacc ccggcatgaa ccacagagtc gaggtgaccg agggcgtcct cagagagcag | 420 |
| tgcgccggga tgctcagcga cttcttccgc gagcggaggg agcagatcaa ggccctccgc | 480 |
| aaggcacaga aggccgagaa tcag | 504 |

<210> SEQ ID NO 52
<211> LENGTH: 501
<212> TYPE: DNA
<213> ORGANISM: Artificial
<220> FEATURE:
<223> OTHER INFORMATION: Sequence encoding novel adenine deaminase 2

<400> SEQUENCE: 52

| | |
|---|---|
| atgagcgaca tcgagcagaa ccacgagtac tggatgcgcc acgccctcgc tctggccagg | 60 |
| agagcctggg aggagggcga ggtcccggtc ggtgctgtcc tcgtccacaa caatcaggtg | 120 |
| ataggcgagg gctggaacag gccgataggc aggcacgatc cgaccgcgca cgcagagatc | 180 |
| atggccctgc ggcaaggcgg cgtcgtgctt cagaactacc gcctcatcga caccaccctg | 240 |
| tacgtcaccc tcgagccgtg cgtcatgtgc gcaggcgcga tggtccacgg caggatcggc | 300 |
| cagctcgtgt tcggggcgag agatgcgaaa accggcgcag ccggctccct gatcgatgtg | 360 |
| ctccaccacc ccgggatgaa ccacagggtc gagatcaccg agggcgtcct cgcagacgag | 420 |
| tgcagcgcca tgctcagcga cttcttccgg caccggcgcc agcaacagaa agccctcaag | 480 |
| cagagcctca agaactccct g | 501 |

<210> SEQ ID NO 53
<211> LENGTH: 507
<212> TYPE: DNA
<213> ORGANISM: Artificial
<220> FEATURE:
<223> OTHER INFORMATION: Sequence encoding novel adenine deaminase 3

<400> SEQUENCE: 53

| | |
|---|---|
| atgagcgacc tcgaactcaa cgacgagtac tggatgcgcc acgccctcac cctcgcaaaa | 60 |
| cgcgcgtggg aggaaggtga ggtgccagtc ggtgcggtcc tcgtccacaa caaccaggtt | 120 |

```
atcggagagg ggtggaaccg cccaatcgga cgccacgacc caaccgctca cgcagagatc    180
atggcccttc ggcagggagg cctcgtcctc cagaactacc gcctcatcga cgccaccctg    240
tacgtcaccc tcgagccctg cgtcatgtgc gcaggcgcga tggtccacag caggatcgcc    300
cggctggtgt tcggagccag ggacgccaaa actggggcag ccgggtccct catggacgtt    360
ctccaccacc ccggcatgaa ccacagggtc gagatcagcg agggcgtcct cgccgaatcg    420
tgcagcgcca tgctcagcga cttcttccgg tggcgccgcg aggagaagaa ggcccaaaag    480
aaagccaggg agcagacggg cgagtcc                                       507
```

```
<210> SEQ ID NO 54
<211> LENGTH: 501
<212> TYPE: DNA
<213> ORGANISM: Artificial
<220> FEATURE:
<223> OTHER INFORMATION: Sequence encoding novel adenine deaminase 4

<400> SEQUENCE: 54
atgagcgacc acgagttcaa cgacgagtac tggatgcgcc acgccctcac actcgccaag     60
agggcctggg aggagggaga ggtgccggtt ggagcagtcc tcgtccacaa caatcaggtg    120
ataggagagg gctggaaccg ccccataggc aggcatgacc cgaccgccca cgcagagatc    180
atggccctcc ggcagggagg cctcgtcctc cagaactacc gcctcatcga cgcaaccctg    240
tacgtcaccc ttgagccgtg cgtcatgtgc gcaggcgcga tggtccacag ccgcatcagc    300
cgcctggtgt ttggagcaag ggacgctaag acggggcag ccggcagcct catcgacgtt    360
ctccaccacc ccggcatgaa ccaccgcgtc gagatcaccg agggcatcct cgcagagagc    420
tgcagcgcaa tgctcagcga cttcttccgc tggcgcaggg aggagaagaa ggccctccgc    480
aaggcacgcc aggaggaggg c                                             501
```

```
<210> SEQ ID NO 55
<211> LENGTH: 498
<212> TYPE: DNA
<213> ORGANISM: Artificial
<220> FEATURE:
<223> OTHER INFORMATION: Sequence encoding novel adenine deaminase 5

<400> SEQUENCE: 55
atgagcgaca tcgagctcaa ccacgagtac tggatgcgcc acgccctcgt cctcgcgcaa     60
agagcctggg acgagggaga ggtccccgtg ggagccgtcc tcgtccacaa caaccaagtg    120
atcggagagg gctggaaccg gcccatcggt agacacgacc ccaccgcgca cgcagaaatc    180
atggcgctcc gccaaggcgg cctcgtcctc cagaactacc gcctcatcga cacgaccctc    240
tacgtcaccc tcgagccctg cgtcatgtgc gcaggagcga tggtccacgg ccgcatcggc    300
aacctcgtgt ttggagcgag agacgccaaa accggcgcag ccggcagctt gatcgacgtg    360
ctccaccacc ccggcatgaa ccacagggtc gagatcaccg agggcgtcct cgcagaggag    420
tgcagcgcga tgcttagcga cttcttccgc caccgcagac agcaacagaa ggcactgcgg    480
caggccgaga aggggagc                                                 498
```

```
<210> SEQ ID NO 56
<211> LENGTH: 504
<212> TYPE: DNA
<213> ORGANISM: Artificial
<220> FEATURE:
<223> OTHER INFORMATION: Sequence encoding novel adenine deaminase 6
```

<400> SEQUENCE: 56

```
atgagcgacc acgagcgcaa cgacgaatac tggatgcgcc acgcactcac cctcgccaag      60
agagcgtggg aggagggtga agtccctgtg ggcgcagtcc tcgtccacaa caaccaagtc     120
atcggcgaag gatggaacag gcccatcggc agacacgacc ctaccgccca cgccgagatc     180
atggccatcc gccaaggcgg cctcgtcctc cagaactacc gcctcatcga cgccacccte     240
tacgtcaccc tcgagccgtg cgtcatgtgc gcaggcgcga tggtccacag ccgcatcagc     300
cgcctggtgt tcggggccag agacgctaag accggtgcag ccggctccct gattgacgtg     360
ctccaccacc ccggcatgaa ccacagagtc gagatcgccg agggcgtgct cgcagagagc     420
tgttccgcga tgctcagcga cttcttccgc tggcgccgcg aggaaaagaa ggccctcaag     480
aaagcccggc aggccgacga gtcc                                            504
```

<210> SEQ ID NO 57
<211> LENGTH: 501
<212> TYPE: DNA
<213> ORGANISM: Artificial
<220> FEATURE:
<223> OTHER INFORMATION: Sequence encoding novel adenine deaminase 7

<400> SEQUENCE: 57

```
atgagcgacc acgagctcaa ccatgaacac tggatgcgcc acgcgctcac cctcgcacaa      60
cgcgcttggg acgaaggcga ggtccctgtc ggagcagtcc tcgtgcacga gaaccgcgtg     120
atcggagagg gctggaacag gcccatcggc aggcatgacc cgaccgcaca cgcagagatc     180
atggccctcc gccaaggcgg cctcgtcctc cagaactacc gcctcatcga caccacccet     240
tacgtcaccc ttgagccctg cgtcatgtgc gcagggggcga tggtcacag ccgcatcggc     300
cagctcgtgt tcggagcaag ggatgctaaa accggggcag ccggctccct gatcgatatc     360
ctccaccacc ccggcatgaa ccacagggtc gagttcaccg agggcgtcct caaggacacc     420
tgcgccaccc tgctcagcga gttcttccgc caccgcaggc aggtcaagaa ggcccttcgc     480
caagccgaga aggacccccg g                                                501
```

<210> SEQ ID NO 58
<211> LENGTH: 504
<212> TYPE: DNA
<213> ORGANISM: Artificial
<220> FEATURE:
<223> OTHER INFORMATION: Sequence encoding novel adenine deaminase 8

<400> SEQUENCE: 58

```
atgagcgaca cgagttcaa ccacgagtac tggatgcgcc acgccctcac actcgcccag      60
agggcgtggg atgaaggcga ggtccctgtc ggcgccgtcc tcgtccttga caaccaggtg     120
atcggagagg gctggaacag gcccatcgga aggcacgacc ctaccgcgca cgcagagatc     180
atggccctgc gccagggcgg catggtcctc cagaactacc gcctcatcaa cgccacccte     240
tacgtcaccc tggagccctg cgtcatgtgc gcaggagcga tggtgcacag caggatcggc     300
cgcgtcgtgt tcggagccag ggacgccaaa actggagccg caggctcgct gatggacgtt     360
ctccaccacc ccggcatgaa ccacagggtc gaggtcacgg agggcatcct cagggaccag     420
tgcgcctcga tgctcagcga cttttttccgc gagcgcaggg agcagatcaa agcactccgc     480
aaggcccaga aggccggcaa ccag                                            504
```

<210> SEQ ID NO 59

```
<211> LENGTH: 504
<212> TYPE: DNA
<213> ORGANISM: Artificial
<220> FEATURE:
<223> OTHER INFORMATION: Sequence encoding novel adenine deaminase 9

<400> SEQUENCE: 59
atgagcatcc cagagtacaa ccacgagtac tggatgcgcc acgccctcac actcgcgcag      60
agagcgtggg acgaaggaga ggtcccggtc ggcgccgtcc tcgtccacaa caaccaagtc     120
atcggagagg gctggaacag gccgatcgga cggcacgatc ccacagcgca cgccgaaatc     180
atggcccttc ggcaaggcgg cctggtgctc cagaactacc gcctcctcga caccaccctg     240
tacgtcaccc tcgagccctg cgtcatgtgc agcggcgcga tggtccacag ccgcatcggc     300
acgctcgtgt tcggagcgag ggacgaaaag accggcgccg cgggatcact gatggacgtg     360
ctcggacacc cggggatgaa ccaccaggtc aagaccatcg gcggcgtcct cgcgcccgag     420
tgctcaggac ttctcagcga cttcttccgc atgcgcaggc agcagaagaa gcagcagaag     480
gccgagctca agctcctggg ggac                                            504

<210> SEQ ID NO 60
<211> LENGTH: 492
<212> TYPE: DNA
<213> ORGANISM: Artificial
<220> FEATURE:
<223> OTHER INFORMATION: Sequence encoding novel adenine deaminase 10

<400> SEQUENCE: 60
atgagcgagg tcgagtttag ccacgagtac tggatgcgcc acgccctcac actcgcgaaa      60
cgggcctggg acgagagaga ggtcaggtgg gtgcgctact ggtacatcac caccgccttc     120
ggagagggct ggaacaggcc gatcggacac cacgacccta cagcccacgc cgagataatg     180
gccctccgcc agggcggcct cgtcctccag aactacaggc tcctcgacgc caccctctac     240
gtcaccctcg agccctgcgt catgtgcgca ggcgcgatgg tgcactcaag aatcgggcgc     300
gtggtgttcg gggccagaga cgcaaaaacg ggcgccgcag ctccctcat ggacgtgctc      360 caccaccccg gcatgaacca cagggtcgac gtcacagagg gcgtcctcag agacgagtgc     420
gccaccctcc tgagcgactt cttccgcatg cgccggcaag agatcaaggc cctgaagaag     480
agcgccaacc ag                                                         492

<210> SEQ ID NO 61
<211> LENGTH: 507
<212> TYPE: DNA
<213> ORGANISM: Artificial
<220> FEATURE:
<223> OTHER INFORMATION: Sequence encoding novel adenine deaminase 11

<400> SEQUENCE: 61
atgagcatcc cagagctcaa ccacgacgtc tggatgaggc acgccctcac actcgccaag      60
agggcgcggg aagaaggtga agtgccggtg ggagccgtcc tcgtgcacaa cggccaggtc     120
atcggagaag gctggaaccg gcccatcgga aggcacgatc ccaccgcaca cgcagagatc     180
atggccctgc gccaaggcgg cctcgtcctg cagaactacc gcctcatcga caccaccctc     240
tacgtcaccc tcgagccctg cgtcatgtgc gcaggcgcta tggtccacag ccgcatcggc     300
cagctggtgt tcggagccag ggatgccaaa accggcgcag caggctcact catcgacgtg     360
```

```
ctccaccacc ccgggatgaa ccacagggtc gagatcaccg agggcgtgct cagagacgag    420
tgcgccgcca tgctcagcga cttcttccgc cagcggcgcc tcgagaagaa ggcgctgaag    480
aaaccaaccg gcgaccccac tgccttc                                        507
```

<210> SEQ ID NO 62
<211> LENGTH: 489
<212> TYPE: DNA
<213> ORGANISM: Artificial
<220> FEATURE:
<223> OTHER INFORMATION: Sequence encoding novel adenine deaminase 12

<400> SEQUENCE: 62

```
atgagcgaca ccgagcagca cgagtattgg atgcgccacg ccctcaccct tgccagacac    60
gcgtgggatg agggggaagt gccagtcgga gctgtcctcg tccacgaggg caacgtgatc    120
ggagaaggct ggaacaggcc catcggaagg cacgacccaa cagcgcacgc cgagataatg    180
gccctccggc agggaggcgc ggtcctccag aactaccgcc tcatcaacgc cacccctgtac  240 gtcaccctcg agccgtgcgt catgtgcgcc ggagcgatgg tccactcaag aatcgcccgg    300
ctggtgttcg gggccaggga cgctaagaca ggggctgcag gttccctcat ggacgtcctg    360
caccacccag gcatgaacca cccgggtcgag atcaccgagg gcgtgctcgg agccgaatgt   420
gcctcgcttc tgagcgactt cttccgccaa cggcgcgagc agaagaaagc gctgaagcgc   480
gggtgctgc                                                            489
```

<210> SEQ ID NO 63
<211> LENGTH: 507
<212> TYPE: DNA
<213> ORGANISM: Artificial
<220> FEATURE:
<223> OTHER INFORMATION: Sequence encoding novel adenine deaminase 13

<400> SEQUENCE: 63

```
atgagcgacc tcgagctcaa cgacgaatac tggatgcgcc acgccctcac acttgccaaa    60
cgcgcccggg aagaaggcga ggtgcccgtg ggggcagtcc ttgtccacaa caaccaagtg    120
ataggcgagg ggtggaacag gcctataggc aggcacgatc ccaccgccca cgcagagatc    180
atggccctcc ggcaaggcgg cctcgtcctc cagaactacc gcctcatcga cgccaccctg    240
tacgtcaccc tcgagccctg tgtcatgtgc gcagggggcga tggtcacacag caggatcgcc    300 cgcctggtgt tcggagcacg ggatgccaaa accggtgcag ccggcagcct catggatgtg    360
ctccaccacc ccggcatgaa ccacagggtc gagatcagcg agggcgtcct cgcagagagc    420
tgctccgcga tgctcagcga cttcttccgc tggcgccgcg aggagaagaa ggcccctcaag   480 aaagcacggg agcagaccgg cgagtcc                                        507
```

<210> SEQ ID NO 64
<211> LENGTH: 501
<212> TYPE: DNA
<213> ORGANISM: Artificial
<220> FEATURE:
<223> OTHER INFORMATION: Sequence encoding novel adenine deaminase 14

<400> SEQUENCE: 64

```
atgagcaacc acgagcttaa ccacgaacac tggatgcgcc acgccctcac actggcccag    60
agggcctggg atgaaggaga ggttcctgtc ggcgccgtcc tcgtccacga caaccgcgtc    120
ataggagagg ggtggaaccg cccgataggc aggcacgacc caacggccca cgcagagatc    180
```

```
atggccctgc gccaaggcgg cctcgtgctc cagaactacc gcctcatcga caccacgctc    240
tacgtcacgc tcgagccgtg cgtcatgtgt gcaggcgcga tggtccacag ccgcatcggc    300
cagctcgtgt ttggagccag agatgccaag acgggtgcag ccggcagctt gatcgacgtc    360
ctccaccacc ccggcatgaa ccacagagtc gagttcaccg agggcgtcct cggagaggag    420
tgtgccgcac tcctctccga cttcttccgc caccggaggc aggtcaaaaa ggccctccgc    480
caggccgaga agagccagga c                                              501
```

<210> SEQ ID NO 65
<211> LENGTH: 519
<212> TYPE: DNA
<213> ORGANISM: Artificial
<220> FEATURE:
<223> OTHER INFORMATION: Sequence encoding novel adenine deaminase 15

<400> SEQUENCE: 65

```
atgagccaga ccgagctcac ccacgagtac tggatgcgcc acgcccttac acttgcccag     60
agggcttggg acgaagggga agtgcctgtg ggagctgtcc tcgtccataa caaccaggtg    120
ataggcgagg gctggaacag gccgataggc aggcatgacc cgaccgccca cgccgaaatc    180
atggcgctcc ggcagggcgg actggtcctc cagaactacc gcctcctgga caccacgctc    240
tacgtcaccc tcgagccgtg cgtcatgtgc gcaggcgcga tggtccacgg acggatcggc    300
acgctcgtgt tcggagccag ggacgcaaag acgggtgccg tcggcagcct tatggacatc    360
accggccacc cggcatgaa ccaccaggtc caggtcatcg agggcatcct cgcaacggag     420
tgtagcgcga tgctcagcgc cttcttccgc cagaggcgcc tcgagaagaa ggccctgaag    480
gaagcgacca agagggccac tggttctgac cctgccgcg                           519
```

<210> SEQ ID NO 66
<211> LENGTH: 96
<212> TYPE: DNA
<213> ORGANISM: Artificial
<220> FEATURE:
<223> OTHER INFORMATION: Sequence encoding Linker 1

<400> SEQUENCE: 66

```
agcggaggtt cttctggcgg gtcaagcggt tccgaaacac ctggcaccag cgagagcgca     60
accccagagt caagcggggg atcgtcaggt ggttcc                               96
```

<210> SEQ ID NO 67
<211> LENGTH: 501
<212> TYPE: DNA
<213> ORGANISM: Artificial
<220> FEATURE:
<223> OTHER INFORMATION: Sequence encoding novel engineered adenine
      deaminase 1

<400> SEQUENCE: 67

```
agcgacaacg agttcaacca cgagtactgg atgcgccacg ccctcacgct tgcccaaagg     60
gccagggacg aaggagaagt gcctgtgggg gccgtcctcg tcctggacaa ccaggtgata    120
ggagagggct ggaaccgggc cataggcctc cacgacccta ccgcccacgc cgagataatg    180
gccctccgcc agggcggcat ggtcctccag aactaccgcc tcatcaacgc caccctgtac    240
gtcaccttcg agccctgcgt catgtgcgca ggcgcgatgg tccacagccg catcggccac    300
gtcgtgttcg gagtcaggaa cgccaagacc ggggcagccg gcagcctttat ggacgtgctc    360 cactaccccg gcatgaacca cagggtcgag gtcaccgaag gggtgctcag ggagcaatgc    420
```

```
gccggcatgc tctgctactt cttccgcgag cccagggagg tgttcaacgc cctgcgcaag    480
gcacagaagg ccgaaaacca g                                              501
```

<210> SEQ ID NO 68
<211> LENGTH: 498
<212> TYPE: DNA
<213> ORGANISM: Artificial
<220> FEATURE:
<223> OTHER INFORMATION: Sequence encoding novel engineered adenine
      deaminase 2

<400> SEQUENCE: 68

```
agcgacatcg agcagaacca cgagtactgg atgcgccacg ccctcgccct cgccaggagg     60
gcgagggagg agggcgaggt tccagtgggg gccgtcctcg tcctcaacaa ccaggtcatt    120
ggcgagggct ggaacagggc catcggcctt cacgatccca ccgccacgc cgagatcatg     180 gccctcaggc aaggcggcgt ggtgctccag aactaccgcc tcatcgacac caccctgtac    240
gtcaccttcg aaccctgcgt catgtgcgcc ggcgcgatgg ttcacggcag gatcggccag    300
ctggtgttcg gcgtgaggaa tgccaagacc ggcgccgccg gctctctgat tgacgtcctc    360
cactaccccg gcatgaacca cagagtcgag atcaccgagg gcgtcctcgc cgacgagtgc    420
tcagccatgc tctgctactt cttccgccac ccgcgccagg tgttcaacgc cctcaagcag    480
agcctcaaga actccctc                                                  498
```

<210> SEQ ID NO 69
<211> LENGTH: 504
<212> TYPE: DNA
<213> ORGANISM: Artificial
<220> FEATURE:
<223> OTHER INFORMATION: Sequence encoding novel engineered adenine
      deaminase 3

<400> SEQUENCE: 69

```
agcgacctcg aactcaacga cgagtactgg atgcgccacg ccctcaccct cgccaagagg     60
gccagggaag aaggagaggt gccggtgggc gcggtcctcg tcctgaacaa ccaagtcata    120
ggcgaggggt ggaacagggc gataggcctc cacgacccga ctgcccacgc cgaaatcatg    180
gccctccggc aaggcggcct cgtgctccag aactaccgcc tcatcgacgc caccctctac    240
gtcaccttcg agccctgcgt gatgtgcgcc ggagcgatgg tgcacagcag gatcgcccgc    300
ctcgtgttcg gagtcaggaa cgccaagacc ggcgccgccg gcagccttat ggacgttctc    360
cactaccccg gcatgaacca cagggtcgag atcagcgagg gcgtgctcgc cgaaagctgc    420
agcgccatgc tctgctactt cttccgctgg ccccgcgagg tgttcaacgc gcagaagaag    480
gccagagagc agaccgggga gtcc                                           504
```

<210> SEQ ID NO 70
<211> LENGTH: 498
<212> TYPE: DNA
<213> ORGANISM: Artificial
<220> FEATURE:
<223> OTHER INFORMATION: Sequence encoding novel engineered adenine
      deaminase 4

<400> SEQUENCE: 70

```
agcgaccacg aattcaacga cgagtactgg atgcgccacg ccctcaccct cgcgaagagg     60
gcgagggaag aaggcgaagt ccccgtcggc gccgtcctcg tcctcaacaa tcaggtgatc    120
ggcgaaggct ggaacagggc catcggcctc catgacccaa cggcgcacgc cgaaatcatg    180
```

-continued

| | |
|---|---|
| gctctgcggc aaggcggcct cgtgctccag aactaccgcc tcatcgacgc caccctctac | 240 |
| gtcacattcg agccctgcgt catgtgcgcc ggcgcgatgg tccatagccg catcagccgg | 300 |
| ctcgtgttcg gcgtcaggaa cgccaagact ggggccgccg gcagccttat tgacgtgctc | 360 |
| cactaccccg gcatgaacca ccgcgtcgag atcaccgagg catcctcgc cgaaagctgc | 420 |
| agcgccatgc tctgctactt cttccgctgg cccagggagg tgttcaacgc cctccgcaag | 480 |
| gccaggcagg aggagggc | 498 |

<210> SEQ ID NO 71
<211> LENGTH: 495
<212> TYPE: DNA
<213> ORGANISM: Artificial
<220> FEATURE:
<223> OTHER INFORMATION: Sequence encoding novel engineered adenine
      deaminase 5

<400> SEQUENCE: 71

| | |
|---|---|
| agcgacatcg agctcaacca cgagtactgg atgcgccacg ccctcgtcct cgcacaaagg | 60 |
| gcgagggacg agggagaggt gcctgtggga gcagtcctcg tcctcaacaa ccaagtcata | 120 |
| ggcgagggct ggaaccgcgc cataggcctc cacgacccaa cggcgcacgc agagatcatg | 180 |
| gcgctccgcc aaggcggcct cgtcctgcag aactaccgcc tcatcgacac cacgctgtac | 240 |
| gtcaccttcg agccctgcgt gatgtgcgca ggcgcgatgg tccacggccg catcggcaac | 300 |
| ctcgtgttcg gagtcaggaa cgccaagacg ggggcagcgg gatcgctcat cgacgtcctc | 360 |
| cactaccccg ggatgaacca cagggtcgag atcaccgagg gcgtcctcgc agaggagtgc | 420 |
| agcgccatgc tctgctactt cttccgccac cccaggcaag tgttcaacgc cctccgccag | 480 |
| gcggagaagg gctcc | 495 |

<210> SEQ ID NO 72
<211> LENGTH: 501
<212> TYPE: DNA
<213> ORGANISM: Artificial
<220> FEATURE:
<223> OTHER INFORMATION: Sequence encoding novel engineered adenine
      deaminase 6

<400> SEQUENCE: 72

| | |
|---|---|
| agcgaccacg agcgcaacga cgagtactgg atgcgccacg ccctcaccct cgccaagagg | 60 |
| gctcgggaag aaggcgaggt ccccgtcggc gctgtcctcg tgctcaacaa ccaggttatc | 120 |
| ggagagggct ggaacagggc catcggactc cacgacccca ctgctcacgc cgagatcatg | 180 |
| gccatccgcc agggaggcct cgtcctgcag aactaccgcc tcatcgacgc aaccctctac | 240 |
| gtcacattcg agccctgcgt catgtgcgca ggcgcgatgg tccacagccg catctcccgg | 300 |
| ctcgtgtttg gagtcaggaa cgccaagacc ggggcagccg gctccctgat tgacgtgctc | 360 |
| cactaccccg gcatgaacca cagggtcgaa atcgccgagg gcgtgctcgc agagagctgc | 420 |
| tcggcgatgc tctgctactt cttccgctgg ccgcgcgagg tgttcaacgc cctcaagaag | 480 |
| gcacggcagg ccgacgagtc c | 501 |

<210> SEQ ID NO 73
<211> LENGTH: 498
<212> TYPE: DNA
<213> ORGANISM: Artificial
<220> FEATURE:
<223> OTHER INFORMATION: Sequence encoding novel engineered adenine
      deaminase 7

<400> SEQUENCE: 73

```
agcgaccacg aactcaacca cgaacactgg atgcgccacg cccttacctt ggcccagcgc    60
gctagagacg aaggagaggt cccagtcgga gcagtcctcg tcctcgagaa ccgcgtgatc   120
ggagagggct ggaaccgggc catcggactc cacgacccaa ccgccacgc agagatcatg    180
gccctccgcc agggaggcct cgtgctgcag aactaccgcc tcatcgacac cacactgtac   240
gtcaccttcg agccgtgcgt gatgtgcgca ggcgcgatgg tgcacagccg catcggccag   300
ctcgtgttcg gagtcaggaa cgccaagacc ggcgcagcgg gctccctcat cgacatcctc   360
cactaccccg gcatgaacca cagggtcgag ttcaccgagg cgtcctcaa ggacacctgc    420
gccaccctcc tctgctactt ctttcgccac cccaggcagg tgttcaacgc cctccggcag   480
gcagagaagg accccgc                                                   498
```

<210> SEQ ID NO 74
<211> LENGTH: 501
<212> TYPE: DNA
<213> ORGANISM: Artificial
<220> FEATURE:
<223> OTHER INFORMATION: Sequence encoding novel engineered adenine deaminase 8

<400> SEQUENCE: 74

```
agcgacaacg agttcaacca cgagtactgg atgcgccacg ccctcacact ggcgcagcgc    60
gcaagagacg agggcgaagt tcccgtgggc gctgtcctcg tcctcgacaa ccaggtgatc   120
ggcgagggct ggaacagagc catcggcctc cacgacccca cagcacacgc agagatcatg   180
gccctgcggc agggcggcat ggtcctccag aactaccgcc tcatcaacgc caccctctac   240
gtcaccttcg agccctgcgt catgtgcgca ggcgcgatgg tccacagcag gatcggccgc   300
gtcgtgttcg gcgtcaggaa cgcaaaaacc ggcgccgcag gctccctgat ggatgtgctc   360
cactaccccg gcatgaacca cagggtcgaa gtcaccgagg catcctcag ggaccagtgc    420
gccagcatgc tctgctactt cttccgcgag cccagggagg tgttcaacgc cctgcgcaag   480
gcccagaagg ccggcaacca g                                              501
```

<210> SEQ ID NO 75
<211> LENGTH: 501
<212> TYPE: DNA
<213> ORGANISM: Artificial
<220> FEATURE:
<223> OTHER INFORMATION: Sequence encoding novel engineered adenine deaminase 9

<400> SEQUENCE: 75

```
agcatccccg agtacaacca cgagtactgg atgcgccacg ccctcacact cgctcagagg    60
gcgagggacg agggcgaggt cccagtcggc gctgtcctcg tcctcaacaa ccaggtcatc   120
ggcgagggct ggaacagggc aatcggcctc cacgacccaa cagcccacgc agagatcatg   180
gccctccggc agggcggcct cgtgcttcag aactaccgcc tcctcgacac cacgctgtac   240
gtcaccttcg agccctgcgt catgtgcagc ggcgcgatgg tccacagccg catcggcacc   300
ctcgtgttcg gcgtcaggaa cgaaaagacc ggcgcagctg cagcctcat ggacgtgctc    360
ggctaccccg gcatgaacca ccaggtcaag accatcggcg gcgtcctcgc acccgagtgc   420
agcggcctgc tctgctactt cttcaggatg cccaggcagg tgttcaacca gcagaaggcc   480
gagctcaagc tcctcggcga c                                              501
```

```
<210> SEQ ID NO 76
<211> LENGTH: 489
<212> TYPE: DNA
<213> ORGANISM: Artificial
<220> FEATURE:
<223> OTHER INFORMATION: Sequence encoding novel engineered adenine
      deaminase 10

<400> SEQUENCE: 76
agcgaggtcg agttctccca cgagtactgg atgcgccacg ccctcaccct ggcaaagagg     60
gcgagggacg agagggaggt caggtgggtc aggtactggc tcatcaccac cgcattcgga    120
gagggctgga acagggcgat cggactccat gacccaaccg cccacgcaga gatcatggcg    180
ctccgccagg gcggcctcgt cctccagaac tacaggctcc tcgacgccac cctctacgtc    240
accttcgagc cctgcgtcat gtgcgcagga gcgatggtgc actccaggat cggacgggtc    300
gtgttcgggg tcaggaacgc caagaccgga gccgcaggct ccctcatgga cgtgctccac    360
taccccggca tgaaccaccg cgtcgacgtg accgagggag tcctcaggga cgagtgcgcc    420
accctccttt gctacttctt ccgcatgccc cgccaggtgt tcaacgccct caagaagtcc    480
gcaaaccag                                                            489

<210> SEQ ID NO 77
<211> LENGTH: 504
<212> TYPE: DNA
<213> ORGANISM: Artificial
<220> FEATURE:
<223> OTHER INFORMATION: Sequence encoding novel engineered adenine
      deaminase 11

<400> SEQUENCE: 77
agcatcccag agctcaacca cgacgtctgg atgaggcacg ccctcaccct cgcgaagagg     60
gccagagagg aggggaagt tccggtgggt gcagtcctcg tcctcaacgg ccaggtgatc    120
ggagaaggct ggaaccgcgc catcggactc cacgaccct ccgccacgc agagatcatg    180 gccctccggc agggaggcct cgtcctccag aactaccgcc tcatcgacac caccctctac    240
gtcaccttcg agccctgcgt catgtgtgca ggcgcgatgg tccacagccg catcggccag    300
ctcgtgttcg gagtcaggaa cgccaagacc ggcgcagcag gcagcctgat cgacgtcctt    360
cactaccccg gcatgaacca cagggtcgag atcaccgagg gcgtcctcag agacgagtgc    420
gccgccatgc tctgctactt cttccgccag ccccgcctcg tgttcaacgc cctcaagaag    480
ccaaccggcg accccaccgc cttc                                           504

<210> SEQ ID NO 78
<211> LENGTH: 486
<212> TYPE: DNA
<213> ORGANISM: Artificial
<220> FEATURE:
<223> OTHER INFORMATION: Sequence encoding novel engineered adenine
      deaminase 12

<400> SEQUENCE: 78
agcgacaccg agcagcacga gtactggatg cgccacgccc tcaccctcgc aagacacgct     60
cgggatgagg gggaagtgcc tgtgggtgct gtgctcgtcc tggagggcaa cgtcatcgga    120
gaagggtgga accgggcgat cggactgcac gatcctaccg cccacgcaga gatcatggcc    180
ctgcggcagg gaggagccgt gctgcagaac taccgcctga tcaacgccac cctctacgtc    240
accttcgagc cctgcgtcat gtgcgcagga gcgatggtgc actcgaggat agcccgcctt    300
gtgttcggcg tcaggaacgc caagacaggg gccgccggaa gcctgatgga tgtgctgcac    360
```

```
taccccggca tgaaccaccg cgtcgagatc accgagggcg tcctcggagc agagtgcgcg    420
tcgctgttgt gttacttctt ccgccagccc cgcgaggtgt tcaacgccct gaagcgcggc    480
tgctgc                                                               486
```

<210> SEQ ID NO 79
<211> LENGTH: 504
<212> TYPE: DNA
<213> ORGANISM: Artificial
<220> FEATURE:
<223> OTHER INFORMATION: Sequence encoding novel engineered adenine
      deaminase 13

<400> SEQUENCE: 79

```
agcgacctcg agctcaacga cgagtactgg atgcgccacg ccctcacact cgccaagagg     60
gcacgcgagg aaggagaggt ccccgtcggg gcagtcctcg tccttaacaa ccaggtcatc    120
ggcgaagggt ggaacagggc gatcggcctc cacgacccta cggctcacgc agagatcatg    180
gccctccgcc agggcggcct cgtccttcag aactaccgcc tcatcgacgc caccctctac    240
gtcaccttcg agccctgcgt catgtgcgca ggcgcgatgg tgcacagcag gatcgcccgc    300
ctcgtgttcg gcgtcaggaa cgcaaagacc ggcgcagcag gcagcctcat ggacgtgctc    360
cactaccccg gcatgaacca cagggtcgag atcagcgagg gcgtcctcgc agagtcgtgc    420
agcgcgatgc tttgctactt cttccgctgg ccccgcgagg tgttcaacgc cctcaagaaa    480
gcacgcgagc aaaccggcga gtcc                                           504
```

<210> SEQ ID NO 80
<211> LENGTH: 498
<212> TYPE: DNA
<213> ORGANISM: Artificial
<220> FEATURE:
<223> OTHER INFORMATION: Sequence encoding novel engineered adenine
      deaminase 14

<400> SEQUENCE: 80

```
agcaaccacg aactcaacca cgaacactgg atgcgccacg ccctcaccttg gctcaaagg     60 gcacgcgacg agggcgaagt tccggtgggt gcagtcctcg tgctcgacaa ccgcgtgatc    120
ggagaaggct ggaaccgggc gatcggactc catgaccccca cggcccacgc agagatcatg    180
gccctccggc agggaggcct cgtgctccag aactaccgcc tcatcgacac cacgctgtac    240
gtcaccttcg agccctgcgt gatgtgcgca ggcgcgatgg tgcacagccg catcggccag    300
ctcgtgttcg gagtcaggaa cgccaagact ggggcagccg cagcctgat tgacgtgctc    360 cactaccccg gcatgaacca cagggtcgag ttcacggagg gcgtcctcgg ggaagaatgc    420 gccgccttc tctgctactt cttccgccac ccaggcagg tgttcaacgc cctccgccag     480
gccgagaaga gccaggac                                                  498
```

<210> SEQ ID NO 81
<211> LENGTH: 516
<212> TYPE: DNA
<213> ORGANISM: Artificial
<220> FEATURE:
<223> OTHER INFORMATION: Sequence encoding novel engineered adenine
      deaminase 15

<400> SEQUENCE: 81

```
agccagaccg agctcaccca cgagtattgg atgcgccacg ccctgacact cgcacagagg     60
gcgcgggacg aagggggaggt ccccgtcggc gcagtcctcg tcctcaacaa ccaagtcatc    120
```

-continued

```
ggcgaagggt ggaacagggc catcggcctc cacgatccga ctgctcacgc agagatcatg      180
gcgctccgcc aaggcggcct cgtgctgcag aactaccgcc tcctcgatac gaccctgtac      240
gtcaccttcg agccctgcgt catgtgcgca ggcgcgatgg tgcacggcag gatcggcacc      300
ctcgtgttcg gcgtcagaaa cgccaagacc ggggccgtcg gaagcctcat ggacatcacc      360
ggctacccgg gcatgaacca ccaggtccag gtcatcgagg gcatcctcgc aaccgagtgc      420
tcggcgatgc tctgttattt cttccgccag ccgcgcctcg tgttcaacgc cctcaaggag      480
gcaacaaaga gggccaccgg ctccgatccg gcagcg                                 516
```

<210> SEQ ID NO 82
<211> LENGTH: 96
<212> TYPE: DNA
<213> ORGANISM: Artificial
<220> FEATURE:
<223> OTHER INFORMATION: Variant sequence encoding Linker 1

<400> SEQUENCE: 82

```
agcggcggct cttctggtgg atcaagcgga agcgaaacac ctggcacgag cgaatccgca      60 accctgagt cgagcggagg cagctcgggt ggttct                                  96
```

<210> SEQ ID NO 83
<211> LENGTH: 372
<212> TYPE: DNA
<213> ORGANISM: Artificial
<220> FEATURE:
<223> OTHER INFORMATION: Exon 1 of an optimized D10A nickase Sp Cas9
      gene

<400> SEQUENCE: 83

```
gacaagaagt acagcatcgg cctcgccatc ggcaccaact cggtgggctg ggccgtcatc      60
acggacgaat ataaggtccc gtcgaagaag ttcaaggtcc tcggcaatac agaccgccac      120
agcatcaaga aaaacttgat cggcgccctc ctgttcgata cggcgagac cgcggaggcg      180 accaggctca agaggaccgc caggagacgg tacactaggc gcaagaacag gatctgctac      240
ctgcaggaga tcttcagcaa cgagatggcg aaggtggacg actccttctt ccaccgcctg      300
gaggaatcat tcctggtgga ggaggacaag aagcatgagc ggcacccaat cttcggcaac      360
atcgtcgacg ag                                                           372
```

<210> SEQ ID NO 84
<211> LENGTH: 3729
<212> TYPE: DNA
<213> ORGANISM: Artificial
<220> FEATURE:
<223> OTHER INFORMATION: Exon 2 of an optimized D10A nickase Sp Cas9
      gene

<400> SEQUENCE: 84

```
gtggcctacc acgagaagta cccgacaatc taccacctcc ggaagaaact ggtggacagc      60
acagacaagg cggacctccg gctcatctac cttgccctcg cgcatatgat caagttccgc      120
ggccacttcc tcatcgaggg cgacctgaac ccggacaact ccgacgtgga caagctgttc      180
atccagctcg tgcagacgta caatcaactg ttcgaggaga cccccataaa cgctagcggc      240
gtggacgcca aggccatcct ctcggccagg ctctcgaaat caagaaggct ggagaacctt      300
atcgcgcagt tgccaggcga aaagaagaac ggcctcttcg gcaacctat tgcgctcagc      360 ctcggcctga cgccgaactt caaatcaaac ttcgacctcg cggaggacgc caagctccag      420
```

```
ctctcaaagg acacctacga cgacgacctc gacaacctcc tggcccagat aggagaccag      480
tacgcggacc tcttcctcgc cgccaagaac ctctccgacg ctatcctgct cagcgacatc      540
cttcgggtca acaccgaaat taccaaggca ccgctgtccg ccagcatgat taaacgctac      600
gacgagcacc atcaggacct cacgctgctc aaggcactcg tccgccagca gctccccgag      660
aagtacaagg agatcttctt cgaccaatca aaaaacggct acgcgggata tatcgacggc      720
ggtgccagcc aggaagagtt ctacaagttc atcaaaccaa tcctggagaa gatggacggc      780
accgaggagt tgctggtcaa gctcaacagg gaggacctcc tcaggaagca gaggaccttc      840
gacaacggct ccatcccgca tcagatccac ctgggcgaac tgcatgccat cctgcggcgc      900
caggaggact tctacccgtt cctgaaggat aaccgggaga agatcgagaa gatcttgacg      960
ttccgcatcc catactacgt gggcccgctg gctcgcggca actcccggtt cgcctggatg     1020 accccggaagt cggaggagac catcacaccc tggaactttg aggaggtggt cgataagggc     1080
gctagcgctc agagcttcat cgagcgcatg accaacttcg ataaaaacct gcccaatgaa     1140
aaagtcctcc ccaagcactc gctgctctac gagtacttca ccgtgtacaa cgagctcacc     1200
aaggtcaaat acgtcaccga gggcatgcgg aagccggcgt tcctgagcgg cgagcagaag     1260
aaggcgatag tggacctcct cttcaagacc aacaggaagg tgaccgtgaa gcaattaaaa     1320
gaggactact tcaagaaaat agagtgcttc gactccgtgg agatctcggg cgtggaggat     1380
cggttcaacg cctcactcgg cacgtatcac gacctcctca agatcattaa agacaaggac     1440
ttcctcgaca acgaggagaa cgaggacatc ctcgaggaca tcgtcctcac cctgaccctg     1500
ttcgaggacc gcgaaatgat cgaggagagg ctgaagacct acgcgcacct gttcgacgac     1560
aaggtcatga acagctcaa gaggcgccgc tacactggtt ggggaaggct gtcccgcaag     1620
ctcattaatg gcatcaggga caagcagagc ggcaagacca tcctggactt cctcaagtcc     1680
gacgggttcg ccaaccgcaa cttcatgcag ctcattcacg acgactcgct cacgttcaag     1740
gaagacatcc agaaggcaca ggtgagcggg cagggtgact ccctccacga acacatcgcc     1800
aacctggccg gctcgccggc cattaaaaag gcatcctgc agacggtcaa ggtcgtcgac     1860
gagctcgtga aggtgatggg ccggcacaag cccgaaaata tcgtcataga gatggccagg     1920
gagaaccaga ccacccaaaa agggcagaag aactcgcgcg agcggatgaa acggatcgag     1980
gagggcatta agagctcgg gtcccagatc ctgaaggagc accccgtgga aaatacccag     2040
ctccagaatg aaaagctcta cctctactac ctgcagaacg gccgcgacat gtacgtggac     2100
caggagctgg acattaatcg gctatcggac tacgacgtcg accacatcgt gccgcagtcg     2160
ttcctcaagg acgatagcat cgacaacaag gtgctcaccc ggtcggataa aaatcggggc     2220
aagagcgaca acgtgcccag cgaggaggtc gtgaagaaga tgaaaaacta ctggcgccag     2280
ctcctcaacg cgaaactgat cacccagcgc aagttcgaca acctgacgaa ggcggaacgc     2340
ggtggcttga cgaactcga taaggcgggc ttcataaaaa ggcagctggt cgagacgcgc     2400
cagatcacga agcatgtcgc ccagatcctg gacagccgca tgaatactaa gtacgatgaa     2460
aacgacaagc tgatccggga ggtgaaggtg atcacgctga agtccaagct cgtgtcggac     2520
ttccgcaagg acttccagtt ctacaaggtc cgcgagatca caactacca ccacgcccac      2580 gacgcctacc tgaatgcggt ggtcgggacc gccctgatca agaagtaccc gaagctggag      2640
tcggagttcg tgtacggcga ctacaaggtc tacgacgtgc gcaaaatgat cgccaagtcc     2700
gagcaggaga tcggcaaggc cacggcaaaa tacttcttct actcgaacat catgaacttc     2760
ttcaagaccg agatcaccct cgcgaacggc gagatccgca agcgcccgct catcgaaacc     2820
```

```
aacggcgaga cgggcgagat cgtctgggat aagggccggg atttcgcgac ggtccgcaag    2880
gtgctctcca tgccgcaagt caatatcgtg aaaaagacgg aggtccagac gggcgggttc    2940
agcaaggagt ccatcctccc gaagcgcaac tccgacaagc tcatcgcgag gaagaaggat    3000
tgggacccga aaaatatgg cggcttcgac agcccgaccg tcgcatacag cgtcctcgtc    3060
gtggcgaagg tggagaaggg caagtcaaag aagctcaagt ccgtgaagga gctgctcggg    3120
atcacgatta tggagcggtc ctccttcgag aagaacccga tcgacttcct agaggccaag    3180
ggatataagg aggtcaagaa ggacctgatt attaaactgc cgaagtactc gctcttcgag    3240
ctggaaaacg gccgcaagag gatgctcgcc tccgcaggcg agttgcagaa gggcaacgag    3300
ctcgccctcc cgagcaaata cgtcaatttc ctgtacctcg ctagccacta tgaaaagctc    3360
aagggcagcc cggaggacaa cgagcagaag cagctcttcg tggagcagca caagcattac    3420
ctggacgaga tcatcgagca gatcagcgag ttctcgaagc gggtgatcct cgccgacgcg    3480
aacctggaca aggtgctgtc ggcatataac aagcaccgcg acaaaccaat acgcgagcag    3540
gccgaaaata tcatccacct cttcacccctc accaacctcg gcgctccggc agccttcaag    3600
tacttcgaca ccacgattga ccggaagcgg tacacgagca cgaaggaggt gctcgatgcg    3660
acgctgatcc accagagcat cacagggctc tatgaaacac gcatcgacct gagccagctg    3720
ggcggagac                                                            3729

<210> SEQ ID NO 85
<211> LENGTH: 189
<212> TYPE: DNA
<213> ORGANISM: Solanum tuberosum

<400> SEQUENCE: 85
gtaagtttct gcttctacct ttgatatata tataataatt atcattaatt agtagtaata     60
taatatttca aatattttt tcaaaataaa agaatgtagt atatagcaat tgcttttctg    120
tagtttataa gtgtgtatat tttaatttat aacttttcta atatatgacc aaaacatggt    180
gatgtgcag                                                            189

<210> SEQ ID NO 86
<211> LENGTH: 12
<212> TYPE: DNA
<213> ORGANISM: Artificial
<220> FEATURE:
<223> OTHER INFORMATION: Sequence encoding linker region 2

<400> SEQUENCE: 86
agcagggccg ac                                                         12

<210> SEQ ID NO 87
<211> LENGTH: 21
<212> TYPE: DNA
<213> ORGANISM: Artificial
<220> FEATURE:
<223> OTHER INFORMATION: Sequence encoding SV40 nuclear localization
      signal

<400> SEQUENCE: 87
ccgaagaaga agcgcaaggt g                                               21

<210> SEQ ID NO 88
<211> LENGTH: 910
<212> TYPE: DNA
<213> ORGANISM: Zea mays
```

<400> SEQUENCE: 88

```
gtcatgggtc gtttaagctg ccgatgtgcc tgcgtcgtct ggtgccctct ctccatatgg      60
aggttgtcaa agtatctgct gttcgtgtca tgagtcgtgt cagtgttggt ttaataatgg     120
accggttgtg ttgtgtgtgc gtactaccca gaactatgac aaatcatgaa taagtttgat     180
gtttgaaatt aaagcctgtg ctcattatgt tctgtctttc agttgtctcc taatatttgc     240
ctgcaggtac tggctatcta ccgtttctta cttaggaggt gtttgaatgc actaaaacta     300
atagttagtg gctaaaatta gttaaaacat ccaaacacca tagctaatag ttgaactatt     360
agctattttt ggaaaattag ttaatagtga ggtagttatt tgttagctag ctaattcaac     420
taacaatttt tagccaacta acaattagtt tcagtgcatt caaacacccc cttaatgtta     480
acgtggttct atctaccgtc tcctaatata tggttgattg ttcggtttgt tgctatgcta     540
ttgggttctg attgctgcta gttcttgctg aatccagaag ttctcgtagt atagctcaga     600
ttcatattat ttatttgagt gataagtgat ccaggttatt actatgttag ctaggttttt     660
tttacaagga taaattatct gtgatcataa ttcttatgaa agctttatgt ttcctggagg     720
cagtggcatg caatgcatga cagcaacttg atcacaccag ctgaggtaga tacggtaaca     780
aggttcttaa atctgttcac caaatcattg gagaacacac atacacattc ttgccagtct     840
tggttagaga aatttcatga caaaatgcca aagctgtctt gactcttcac ttttggccat     900
gagtcgtgac                                                            910
```

<210> SEQ ID NO 89
<211> LENGTH: 1001
<212> TYPE: DNA
<213> ORGANISM: Zea mays

<400> SEQUENCE: 89

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggg ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgttttcca gctgttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta ttttttttata tacctttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt g                        1001
```

<210> SEQ ID NO 90

```
<211> LENGTH: 20
<212> TYPE: DNA
<213> ORGANISM: Zea mays

<400> SEQUENCE: 90
atatatattc aatcaggatc                                                 20

<210> SEQ ID NO 91
<211> LENGTH: 77
<212> TYPE: DNA
<213> ORGANISM: Artificial
<220> FEATURE:
<223> OTHER INFORMATION: Sequence encoding Cas recognition domain of
      gRNA

<400> SEQUENCE: 91
gttttagagc tagaaatagc aagttaaaat aaggctagtc cgttatcaac ttgaaaaagt     60
ggcaccgagt cggtgct                                                    77

<210> SEQ ID NO 92
<211> LENGTH: 910
<212> TYPE: DNA
<213> ORGANISM: Zea mays

<400> SEQUENCE: 92
gtcatgggtc gtttaagctg ccgatgtgcc tgcgtcgtct ggtgccctct ctccatatgg     60
aggttgtcaa agtatctgct gttcgtgtca tgagtcgtgt cagtgttggt ttaataatgg    120
accggttgtg ttgtgtgtgc gtactaccca gaactatgac aaatcatgaa taagtttgat    180
gtttgaaatt aaagcctgtg ctcattatgt tctgtctttc agttgtctcc taatatttgc    240
ctgcaggtac tggctatcta ccgtttctta cttaggaggt gtttgaatgc actaaaacta    300
atagttagtg gctaaaatta gttaaaacat ccaaacacca tagctaatag ttgaactatt    360
agctattttt ggaaaattag ttaatagtga ggtagttatt tgttagctag ctaattcaac    420
taacaatttt tagccaacta acaattagtt tcagtgcatt caaacacccc cttaatgtta    480
acgtggttct atctaccgtc tcctaatata tggttgattg ttcggtttgt tgctatgcta    540
ttgggttctg attgctgcta gttcttgctg aatccagaag ttctcgtagt atagctcaga    600
ttcatattat ttatttgagt gataagtgat ccaggttatt actatgttag ctaggttttt    660
tttacaagga taaattatct gtgatcataa ttcttatgaa agctttatgt ttcctggagg    720
cagtggcatg caatgcatga cagcaacttg atcacaccag ctgaggtaga tacggtaaca    780
aggttcttaa atctgttcac caaatcattg gagaacacac atacacattc ttgccagtct    840
tggttagaga aatttcatga caaaatgcca aagctgtctt gactcttcac ttttggccat    900
gagtcgtgac                                                           910

<210> SEQ ID NO 93
<211> LENGTH: 59
<212> TYPE: PRT
<213> ORGANISM: Raoultella sp.

<400> SEQUENCE: 93

Asp Ala Lys Thr Gly Ala Ala Gly Ser Leu Ile Asp Val Leu His His
1               5                   10                  15

Pro Gly Met Asn His Arg Val Glu Ile Ala Glu Gly Val Leu Ala Glu
                20                  25                  30

Ser Cys Ser Ala Met Leu Ser Asp Phe Phe Arg Trp Arg Arg Glu Glu
        35                  40                  45
```

```
Lys Lys Ala Leu Lys Lys Ala Arg Gln Ala Asp
         50                  55
```

<210> SEQ ID NO 94
<211> LENGTH: 58
<212> TYPE: PRT
<213> ORGANISM: Klebsiella aerogenes

<400> SEQUENCE: 94

```
Asp Ala Lys Thr Gly Ala Ala Gly Ser Leu Ile Asp Val Leu His His
1               5                   10                  15

Pro Gly Met Asn His Arg Val Glu Ile Thr Glu Gly Ile Leu Ala Glu
            20                  25                  30

Ser Cys Ser Ala Met Leu Ser Asp Phe Phe Arg Trp Arg Arg Glu Glu
        35                  40                  45

Lys Lys Ala Leu Arg Lys Ala Arg Gln Glu
         50                  55
```

<210> SEQ ID NO 95
<211> LENGTH: 60
<212> TYPE: PRT
<213> ORGANISM: Klebsiella pneumoniae

<400> SEQUENCE: 95

```
Asp Ala Lys Thr Gly Ala Ala Gly Ser Leu Met Asp Val Leu His His
1               5                   10                  15

Pro Gly Met Asn His Arg Val Glu Ile Ser Glu Gly Val Leu Ala Glu
            20                  25                  30

Ser Cys Ser Ala Met Leu Ser Asp Phe Phe Arg Trp Arg Arg Glu Glu
        35                  40                  45

Lys Lys Ala Gln Lys Lys Ala Arg Glu Gln Thr Gly
         50                  55                  60
```

<210> SEQ ID NO 96
<211> LENGTH: 60
<212> TYPE: PRT
<213> ORGANISM: Klebsiella pneumoniae

<400> SEQUENCE: 96

```
Asp Ala Lys Thr Gly Ala Ala Gly Ser Leu Met Asp Val Leu His His
1               5                   10                  15

Pro Gly Met Asn His Arg Val Glu Ile Ser Glu Gly Val Leu Ala Glu
            20                  25                  30

Ser Cys Ser Ala Met Leu Ser Asp Phe Phe Arg Trp Arg Arg Glu Glu
        35                  40                  45

Lys Lys Ala Leu Lys Lys Ala Arg Glu Gln Thr Gly
         50                  55                  60
```

<210> SEQ ID NO 97
<211> LENGTH: 58
<212> TYPE: PRT
<213> ORGANISM: Escherichia coli

<400> SEQUENCE: 97

```
Asp Ala Lys Thr Gly Ala Ala Gly Ser Leu Met Asp Val Leu His His
1               5                   10                  15

Pro Gly Met Asn His Arg Val Glu Ile Thr Glu Gly Ile Leu Ala Asp
            20                  25                  30
```

-continued

```
Glu Cys Ala Ala Leu Leu Ser Asp Phe Phe Arg Met Arg Arg Gln Glu
         35                  40                  45

Ile Lys Ala Gln Lys Lys Ala Gln Ser Ser
     50                  55

<210> SEQ ID NO 98
<211> LENGTH: 59
<212> TYPE: PRT
<213> ORGANISM: Enterobacteriaceae bacterium strain FGI 57

<400> SEQUENCE: 98

Asp Ala Lys Thr Gly Ala Ala Gly Ser Leu Met Asp Val Leu His His
1               5                   10                  15

Pro Gly Met Asn His Arg Val Glu Val Thr Glu Gly Val Leu Arg Glu
             20                  25                  30

Gln Cys Ala Gly Met Leu Ser Asp Phe Phe Arg Glu Arg Arg Glu Gln
         35                  40                  45

Ile Lys Ala Leu Arg Lys Ala Gln Lys Ala Glu
     50                  55

<210> SEQ ID NO 99
<211> LENGTH: 58
<212> TYPE: PRT
<213> ORGANISM: Kluyvera georgiana

<400> SEQUENCE: 99

Asp Ala Lys Thr Gly Ala Ala Gly Ser Leu Ile Asp Val Leu His His
1               5                   10                  15

Pro Gly Met Asn His Arg Val Glu Ile Thr Glu Gly Val Leu Ala Asp
             20                  25                  30

Glu Cys Ser Ala Met Leu Ser Asp Phe Phe Arg His Arg Gln Gln
         35                  40                  45

Gln Lys Ala Leu Lys Gln Ser Leu Lys Asn
     50                  55

<210> SEQ ID NO 100
<211> LENGTH: 58
<212> TYPE: PRT
<213> ORGANISM: Kluyvera ascorbata ATCC 33433

<400> SEQUENCE: 100

Asp Ala Lys Thr Gly Ala Ala Gly Ser Leu Ile Asp Val Leu His His
1               5                   10                  15

Pro Gly Met Asn His Arg Val Glu Ile Thr Glu Gly Val Leu Ala Glu
             20                  25                  30

Glu Cys Ser Ala Met Leu Ser Asp Phe Phe Arg His Arg Arg Gln Gln
         35                  40                  45

Gln Lys Ala Leu Arg Gln Ala Glu Lys Gly
     50                  55

<210> SEQ ID NO 101
<211> LENGTH: 58
<212> TYPE: PRT
<213> ORGANISM: Klebsiella sp. RIT-PI-d

<400> SEQUENCE: 101

Asp Ala Lys Thr Gly Ala Ala Gly Ser Leu Ile Asp Ile Leu His His
1               5                   10                  15
```

-continued

Pro Gly Met Asn His Arg Val Glu Phe Thr Glu Gly Val Leu Lys Asp
            20                  25                  30

Thr Cys Ala Thr Leu Leu Ser Glu Phe Phe Arg His Arg Arg Gln Val
        35                  40                  45

Lys Lys Ala Leu Arg Gln Ala Glu Lys Asp
    50                  55

<210> SEQ ID NO 102
<211> LENGTH: 59
<212> TYPE: PRT
<213> ORGANISM: Pseudocitrobacter faecalis

<400> SEQUENCE: 102

Asp Ala Lys Thr Gly Ala Ala Gly Ser Leu Met Asp Val Leu His His
1               5                   10                  15

Pro Gly Met Asn His Arg Val Glu Val Thr Glu Gly Ile Leu Arg Asp
            20                  25                  30

Gln Cys Ala Ser Met Leu Ser Asp Phe Phe Arg Glu Arg Arg Glu Gln
        35                  40                  45

Ile Lys Ala Leu Arg Lys Ala Gln Lys Ala Gly
    50                  55

<210> SEQ ID NO 103
<211> LENGTH: 59
<212> TYPE: PRT
<213> ORGANISM: Enterobacter cloacae (15)

<400> SEQUENCE: 103

Asp Glu Lys Thr Gly Ala Ala Gly Ser Leu Met Asp Val Leu Gly His
1               5                   10                  15

Pro Gly Met Asn His Gln Val Lys Thr Ile Gly Gly Val Leu Ala Pro
            20                  25                  30

Glu Cys Ser Gly Leu Leu Ser Asp Phe Phe Arg Met Arg Arg Gln Gln
        35                  40                  45

Lys Lys Gln Gln Lys Ala Glu Leu Lys Leu Leu
    50                  55

<210> SEQ ID NO 104
<211> LENGTH: 57
<212> TYPE: PRT
<213> ORGANISM: Citrobacter youngae

<400> SEQUENCE: 104

Asp Ala Lys Thr Gly Ala Ala Gly Ser Leu Met Asp Val Leu His His
1               5                   10                  15

Pro Gly Met Asn His Arg Val Asp Val Thr Glu Gly Val Leu Arg Asp
            20                  25                  30

Glu Cys Ala Thr Leu Leu Ser Asp Phe Phe Arg Met Arg Arg Gln Glu
        35                  40                  45

Ile Lys Ala Leu Lys Lys Ser Ala Asn
    50                  55

<210> SEQ ID NO 105
<211> LENGTH: 60
<212> TYPE: PRT
<213> ORGANISM: Kosakonia pseudosacchari

<400> SEQUENCE: 105

Asp Ala Lys Thr Gly Ala Ala Gly Ser Leu Ile Asp Val Leu His His
1               5                   10                  15

Pro Gly Met Asn His Arg Val Glu Ile Thr Glu Gly Val Leu Arg Asp
            20                  25                  30

Glu Cys Ala Ala Met Leu Ser Asp Phe Phe Arg Gln Arg Arg Leu Glu
        35                  40                  45

Lys Lys Ala Leu Lys Lys Pro Thr Gly Asp Pro Thr
    50                  55                  60

<210> SEQ ID NO 106
<211> LENGTH: 56
<212> TYPE: PRT
<213> ORGANISM: Pluralibacter gergoviae

<400> SEQUENCE: 106

Asp Ala Lys Thr Gly Ala Ala Gly Ser Leu Met Asp Val Leu His His
1               5                   10                  15

Pro Gly Met Asn His Arg Val Glu Ile Thr Glu Gly Val Leu Gly Ala
            20                  25                  30

Glu Cys Ala Ser Leu Leu Ser Asp Phe Phe Arg Gln Arg Glu Gln
        35                  40                  45

Lys Lys Ala Leu Lys Arg Gly Cys
    50                  55

<210> SEQ ID NO 107
<211> LENGTH: 58
<212> TYPE: PRT
<213> ORGANISM: Superficieibacter electus

<400> SEQUENCE: 107

Asp Ala Lys Thr Gly Ala Ala Gly Ser Leu Ile Asp Val Leu His His
1               5                   10                  15

Pro Gly Met Asn His Arg Val Glu Phe Thr Glu Gly Val Leu Gly Glu
            20                  25                  30

Glu Cys Ala Ala Leu Leu Ser Asp Phe Phe Arg His Arg Arg Gln Val
        35                  40                  45

Lys Lys Ala Leu Arg Gln Ala Glu Lys Ser
    50                  55

<210> SEQ ID NO 108
<211> LENGTH: 60
<212> TYPE: PRT
<213> ORGANISM: Cronobacter malonaticus

<400> SEQUENCE: 108

Asp Ala Lys Thr Gly Ala Val Gly Ser Leu Met Asp Ile Thr Gly His
1               5                   10                  15

Pro Gly Met Asn His Gln Val Gln Val Ile Glu Gly Ile Leu Ala Thr
            20                  25                  30

Glu Cys Ser Ala Met Leu Ser Ala Phe Phe Arg Gln Arg Arg Leu Glu
        35                  40                  45

Lys Lys Ala Leu Lys Glu Ala Thr Lys Arg Ala Thr
    50                  55                  60

<210> SEQ ID NO 109
<211> LENGTH: 26
<212> TYPE: PRT

```
<213> ORGANISM: Artificial Sequence
<220> FEATURE:
<223> OTHER INFORMATION: Consensus motif
<220> FEATURE:
<221> NAME/KEY: MISC_FEATURE
<222> LOCATION: (22)..(22)
<223> OTHER INFORMATION: X is L or Q
<220> FEATURE:
<221> NAME/KEY: MISC_FEATURE
<222> LOCATION: (23)..(23)
<223> OTHER INFORMATION: X is K or R

<400> SEQUENCE: 109

Ala Glu Ser Cys Ser Ala Met Leu Ser Asp Phe Phe Arg Trp Arg Arg
1               5                   10                  15

Glu Glu Lys Lys Ala Xaa Xaa Lys Ala Arg
            20                  25

<210> SEQ ID NO 110
<211> LENGTH: 23
<212> TYPE: DNA
<213> ORGANISM: Zea mays

<400> SEQUENCE: 110
atatatattc aatcaggatc agg                                             23
```